United States Patent
Barnicki

(10) Patent No.: US 10,329,230 B2
(45) Date of Patent: Jun. 25, 2019

(54) PROCESS FOR THE SEPARATION AND PURIFICATION OF A MIXED DIOL STREAM

(71) Applicant: Eastman Chemical Company, Kingsport, TN (US)

(72) Inventor: Scott Donald Barnicki, Kingsport, TN (US)

(73) Assignee: Eastman Chemical Company, Kingsport, TN (US)

( * ) Notice: Subject to any disclaimer, the term of this patent is extended or adjusted under 35 U.S.C. 154(b) by 579 days.

(21) Appl. No.: 14/950,503

(22) Filed: Nov. 24, 2015

(65) Prior Publication Data

US 2016/0075622 A1    Mar. 17, 2016
US 2017/0036976 A9    Feb. 9, 2017

Related U.S. Application Data

(60) Division of application No. 13/431,308, filed on Mar. 27, 2012, now Pat. No. 9,227,896, which is a
(Continued)

(51) Int. Cl.
*C07C 29/86* (2006.01)
*C07C 29/149* (2006.01)
(Continued)

(52) U.S. Cl.
CPC ........... *C07C 29/86* (2013.01); *B01J 31/2409* (2013.01); *C07C 29/149* (2013.01);
(Continued)

(58) Field of Classification Search
CPC ....... C07C 29/80; C07C 29/86; C07C 29/149; B01J 31/2409
See application file for complete search history.

(56) References Cited

U.S. PATENT DOCUMENTS 2,152,852 A    4/1939  Loder
2,153,064 A    4/1939  Larson
(Continued)

FOREIGN PATENT DOCUMENTS

CN    1084503 A    3/1994
CN    1335295 A    2/2002
(Continued)

OTHER PUBLICATIONS

Notification of Transmittal of the International Search Report and the Written Opinion of the International Search Authority dated Mar. 15, 2012 for International Application No. PCT/US2011/051490.
(Continued)

*Primary Examiner* — Yate' K Cutliff
(74) *Attorney, Agent, or Firm* — Polly C. Owen

(57) ABSTRACT

Disclosed is a process for the purification of a mixed diol stream. The mixed diol stream comprising two-, three-, and four-carbon diols is separated into component diols by extraction with a hydrophobic solvent mixture. The diols recovered in the extractant may be removed from the extractant stream by back extraction with water or by distillation with an azeotrope-forming agent present, preferably an azeotroping agent already present in the extractant mixture.

9 Claims, 2 Drawing Sheets

Related U.S. Application Data continuation-in-part of application No. 12/889,065, filed on Sep. 23, 2010, now Pat. No. 8,466,328.

(60) Provisional application No. 61/374,850, filed on Aug. 18, 2010.

(51) Int. Cl.
  *B01J 31/24* (2006.01)
  *C07C 29/80* (2006.01)

(52) U.S. Cl.
  CPC .. *B01J 2531/0258* (2013.01); *B01J 2531/821* (2013.01); *C07C 29/80* (2013.01); *Y02P 20/52* (2015.11)

(56) References Cited

U.S. PATENT DOCUMENTS

| | | | |
|---|---|---|---|
| 2,211,624 A | 8/1940 | Loder et al. | |
| 2,211,625 A | 8/1940 | Loder | |
| 2,298,138 A | 10/1942 | Loder | |
| 2,436,209 A | 2/1948 | Elgin | |
| 2,443,482 A | 6/1948 | Shattuck | |
| 3,333,924 A | 8/1967 | Hazen et al. | |
| 3,751,453 A | 8/1973 | Kurkov et al. | |
| 3,754,028 A | 8/1973 | Lapporte et al. | |
| 3,801,627 A | 4/1974 | Kurkov et al. | |
| 3,859,349 A | 1/1975 | Cody | |
| 3,911,003 A | 10/1975 | Suzuki | |
| 3,927,078 A | 12/1975 | Lapporte et al. | |
| 3,948,977 A | 4/1976 | Suzuki | |
| 3,948,986 A | 4/1976 | Suzuki | |
| 4,016,208 A | 4/1977 | Suzuki | |
| 4,052,452 A | 10/1977 | Scardigno et al. | |
| 4,087,470 A | 5/1978 | Suzuki | |
| 4,112,245 A | 9/1978 | Zehner et al. | |
| 4,128,575 A | 12/1978 | Leupold et al. | |
| 4,136,112 A | 1/1979 | Bakshi | |
| 4,140,866 A | 2/1979 | Nielsen | |
| 4,153,809 A | 5/1979 | Suzuki | |
| 4,228,305 A | 10/1980 | Suzuki | |
| 4,275,234 A | 6/1981 | Baniel et al. | |
| 4,291,007 A | 9/1981 | Baniel | |
| 4,308,397 A | 12/1981 | Suzuki | |
| 4,366,333 A | 12/1982 | Wilkes | |
| 4,409,395 A | 10/1983 | Miyazaki et al. | |
| 4,431,486 A | 2/1984 | Balmat | |
| 4,440,734 A | 4/1984 | Kougioumoutzakis | |
| 4,501,917 A | 2/1985 | Schmidt et al. | |
| 4,691,048 A | 9/1987 | Hughes et al. | |
| 4,824,997 A | 4/1989 | Macfarlane et al. | |
| 4,935,102 A | 6/1990 | Berg | |
| 4,966,658 A | 10/1990 | Berg | |
| 4,990,629 A | 2/1991 | Souma | |
| 5,026,927 A | 6/1991 | Andrews et al. | |
| 5,210,335 A | 5/1993 | Schuster et al. | |
| 5,214,219 A | 5/1993 | Casale et al. | |
| 5,276,181 A | 1/1994 | Casale et al. | |
| 5,423,955 A | 6/1995 | Berg | |
| 5,455,372 A | 10/1995 | Hirai et al. | |
| 5,580,991 A | 12/1996 | Sugiyama et al. | |
| 5,723,662 A | 3/1998 | Ebmeyer et al. | |
| 5,932,772 A | 8/1999 | Argyropoulos et al. | |
| 5,952,530 A | 9/1999 | Argyropoulos et al. | |
| 6,252,121 B1 | 6/2001 | Argyropoulos et al. | |
| 6,291,725 B1 | 9/2001 | Chopade et al. | |
| 6,294,700 B1 | 9/2001 | Kanel et al. | |
| 6,303,829 B1 | 10/2001 | Kanel et al. | |
| 6,307,108 B1 | 10/2001 | Argyropoulos et al. | |
| 6,307,109 B1 | 10/2001 | Kanel et al. | |
| 6,307,110 B1 | 10/2001 | Argyropoulos et al. | |
| 6,310,260 B1 | 10/2001 | Argyropoulos et al. | |
| 6,376,723 B2 | 4/2002 | Drent et al. | |
| 6,603,048 B1 * | 8/2003 | Corbin | B01D 15/00 568/868 |
| 7,122,698 B2 | 10/2006 | Yoshida et al. | |
| 7,164,040 B2 | 1/2007 | Kuroda et al. | |
| 7,223,885 B2 | 5/2007 | Van Krieken | |
| 7,439,391 B2 | 10/2008 | Gallagher et al. | |
| 7,615,671 B2 | 11/2009 | Puckette et al. | |
| 7,709,689 B2 | 5/2010 | Kilner et al. | |
| 7,772,423 B2 | 8/2010 | Celik et al. | |
| 8,466,328 B2 | 6/2013 | Barnicki et al. | |
| 8,829,248 B2 * | 9/2014 | Barnicki | B01J 31/24 568/864 |
| 2004/0222153 A1 | 11/2004 | Baniel et al. | |
| 2006/0160197 A1 | 7/2006 | Li et al. | |
| 2007/0123739 A1 | 5/2007 | Crabtree et al. | |
| 2008/0275277 A1 | 11/2008 | Kalagias | |
| 2009/0143612 A1 | 6/2009 | Puckette et al. | |
| 2011/0144388 A1 | 6/2011 | Sun et al. | |
| 2011/0166383 A1 | 7/2011 | Sun et al. | |
| 2012/0046481 A1 | 2/2012 | Barnicki et al. | |
| 2012/0046500 A1 | 2/2012 | Barnicki et al. | |
| 2012/0078010 A1 | 3/2012 | Barnicki et al. | |
| 2012/0184783 A1 | 7/2012 | Barnicki et al. | |

FOREIGN PATENT DOCUMENTS

| | | |
|---|---|---|
| CN | 101264394 A | 9/2008 |
| DE | 3133353 C2 | 3/1983 |
| EP | 0 114 657 B1 | 3/1987 |
| EP | 1 679 331 A1 | 7/2006 |
| GB | 508383 A | 6/1939 |
| GB | 1499245 A | 1/1978 |
| GB | 2179337 A | 7/1986 |
| IL | 89044 A | 3/1993 |
| JP | S5673042 A | 6/1981 |
| JP | 56100741 A | 8/1981 |
| JP | 56131546 A | 10/1981 |
| JP | 56133237 A | 10/1981 |
| JP | 5746934 A | 3/1982 |
| JP | 57040442 A | 3/1982 |
| JP | 57102837 A | 6/1982 |
| JP | 6228045 A | 8/1994 |
| JP | H09 215934 | 8/1997 |
| JP | 1999147042 A | 6/1999 |
| JP | 2004131411 A | 4/2004 |
| RU | 1436453 A1 | 9/1996 |
| WO | WO 97/15543 A1 | 5/1997 |
| WO | WO 2006/069127 A1 | 6/2006 |
| WO | WO 2009/140850 A1 | 11/2009 |
| WO | WO 2012/040007 A2 | 3/2012 |
| WO | WO 2012/0130316 A1 | 10/2012 |

OTHER PUBLICATIONS

Notification of Transmittal of the International Search Report and the Written Opinion of the International Search Authority dated Nov. 28, 2011 for International Application No. PCT/US2011/047842.

Notification of Transmittal of the International Search Report and the Written Opinion of the International Search Authority dated Aug. 13, 2013 for International Application No. PCT/US2013/033458.

Notification of Transmittal of the International Search Report and the Written Opinion of the International Search Authority dated Jun. 25, 2013 for International Application No. PCT/US2013/033501.

Notification of Transmittal of the International Search Report and the Written Opinion of the International Search Authority dated Aug. 16, 2013 for International Application No. PCT/US2013/033410.

Notification of Transmittal of the International Search Report and the Written Opinion of the International Search Authority dated Jun. 21, 2013 for International Application No. PCT/US2013/033520.

Notification of Transmittal of the International Search Report and the Written Opinion of the International Search Authority dated Jun. 21, 2013 for International Application No. PCT/US2013/033411.

Notification of Transmittal of the International Search Report and the Written Opinion of the International Search Authority dated Jul. 8, 2013 for International Application No. PCT/US2013/033494.

(56) References Cited

OTHER PUBLICATIONS

Notification of Transmittal of the International Search Report and the Written Opinion of the International Search Authority dated Jul. 12, 2013 for International Application No. PCT/US2013/033446.
Celik et al., "Synthesis of precursors to ethylene glycol from formaldehyde and methyl formate catalyzed by heteropoly acids", Journal of Molecular Catalysis A: Chemical 288, (2008), pp. 87-96.
Celik et al., "Vapor-phase carbonylation of dimethoxymethane of H-Faujasite", Angewandte. Chemie Int. Ed. 2009, 48, pp. 4813-4815.
Hou-Yong, Sun, et al. "Reactive extraction of glycolic acid in high content solution with tri-n-octylamine" Journal of Chemical Engineering of Chinese Universities, Feb. 2007, vol. 21 pp. 26-30.
Asci, Yavuz Selim et al. "Extraction of Glycolic Acid from Aqueous Solutions by Amberlite LA-2 in Difference Diluent Solvents" J. Chem Eng. Data 2009, 54, 2791-2794.
Bizek, Vladislav et al. "Amine Extraction of Hydroxycarboxylic Acids. 1. Extraction of Citric Acid with 1-Octanol/n-Heptane Solutions of Trialkylamine" Ind. Eng. Chem. Res. 1992, 31, 1554-1562.
Tamada, Janet A. et al. "Extraction of Carboxylic Acids with Amine Extractants. 1. Equilibria and Law of Mass Action Modeling" Ind. Eng. Chem. Res. 1990, 29, 1319-1326.
Smith, E. Lester, et al., "The Acid-Binding Properties of Long-Chain Aliphatic Amines", J.S.C.I., 67, Feb. 1948 pp. 48-51.
Walker, "Formaldehyde", ACS Monograph, Washington, DC., (1964), p. 95.
Eyal, A., et al. "Recovery and Concentration of Strong Mineral Acids from Dilute Solutions Through LLX III. A "Temperature Swing" Based Process", Solvent Extraction and Ion Exchange, 9 (2), pp. 223-236 (1991).
Eyal, A.M., et al. "Recovery and Concentration of Strong Mineral Acids from Dilute Soltions Through LLX. I: Review of Parameters for Adjusting Extractant Properties and Analysis of Process Options", Solvent Extraction and Ion Exchange, 9 (2), pp. 195-210 (1991).
Eyal, A.M., et al. "Recovery and Concentration of Strong Mineral Acids from Dilute Solutions Through LLX. II. Reversible Extraction with Branched-Chain Amines", Solvent Extraction and Ion Exchange, 9(2), pp. 211-222 (1991).
Eyal, Aharon, et al. "Extraction of Strong Mineral Acids by Organic Acid-Base Couples", Ind. Eng. Chem. Process Des. Dev., (1982), vol. 21, No. 2, pp. 334-337.
Handbook of Solvent Extraction, Krieger Publishing Company, Malabar, FL, 1991, pp. 275-501.
Treybal, Robert E. "Methods of Calculation II. Stagewise Contact, Multicomponent Systems", Liquid Extraction, $2^{nd}$ Edition, McGraw-Hill Book Company, New York. 1963, pp. 275-276.
Treybal, Robert E., Liquid Extraction, $2^{nd}$ Ed., McGraw-Hill Book Company, New York, NY, 1963, pp. 349-366.
Gerberich, H. Robert, et al., "Formaldehyde", Kirk-Othmer Encyclopedia of Chemical Technology, vol. 11, $4^{th}$ Edition, 1994, pp. 929-951.
Treybal, Robert E., Liquid Extraction, $2^{nd}$ Ed., McGraw Hill Book Company, 1963, pp. 248-252.
Lynch, Kathleen M., et al., "Improved Preparations of 3-Chloro-2(chloromethyl)-1-propene and 1,1-Dibromo-2,2-bis(chloromethyl)-cyclopropane: Intermediates in the Synthesis of [1.1.1]Propellane", J. Org. Chem, 60, (1995), pp. 4666-4668.
"Tray Design and Operation", Distillation Design, McGraw-Hill, New York (1992), Chapter 6, pp. 259-363.
"Packing Design and Operation", Distillation Design, McGraw-Hill, New York, (1992), Chapter 8, pp. 421-521.
Seader, J.D., Ph.D, et al., "Distillation", Perry's Handbook of Chemical Engineering, Section 13, $7^{th}$ Ed., McGraw-Hill Book Co. 1999.
Lee, Sang Young, et al., "Carbonylation of Formaldehyde over Ion Exchange Resin Catalysts. 1. Batch Reactor Studies", Ind. Eng. Chem. Res., 32, (1993), pp. 253-259.
Xu, Qiang, et al., "Preparation and Catalytic Application of Cationic Metal Carbonyls", Science and Technology in Catalysis, (2002), pp. 215-218.
Xu, Qiang, "Metal carbonyl cations: generation, characterization and catalytic application", Coordination Chemistry Reviews, 231, (2002), pp. 83-108.
Suzuki, S., et al., " Ethylene Glycol from Methanol and Synthesis Gas via Glycolic Acid", Catalytic Conversions of Synthesis Gas and Alcohols to Chemicals, (1984). pp. 221-247.
Wang, Zheng Bao, et al., Carbonylation of Formaldehyde with Carbon Monoxide over Cation-Exchange Resin Catalysts, Bull. Chem. Soc. Jpn., 72, (1999), pp. 1935-1940.
Sano, Tsunejo, et al., "Synthesis of 1,3-dioxolan-4-one from trioxane and carbon monoxide on HZSM-5 zeolite", Chem. Community, (1997), pp. 1827-1828.
Souma, Yoshie, "Carbonylation at Ambient Pressure in Strong Acids", Journal of Synthetic Organic Chemistry, vol. 41, No. 6, (1983), pp. 561-569.
Soma, Yoshie, et al., "Normal-Pressure CO Addition Reaction of Formaldehyde and Related Compounds on Copper Carbonyl Catalyst", Catalyst 23, (1981), pp. 48-50.
Li, Tao, et al., "Carbonylation of formaldehyde catalyzed by p-toluenesulfonic acid", Catalysis Today, 111, (2006), pp. 288-291.
Souma, Yoshie, et al., "Synthesis of tert.-Alkanoic acid catalyzed by $Cu(CO)^+_n$ and $Ag(CO)^+_2$ under atmospheric pressure", Catalysis Today, 36, (1997), pp. 91-97.
Hendriksen, Dan E., "Intermediates to Ethylene Glycol: Carbonylation of Formaldehyde Catalyzed by NAFION Solid Perfluorosulfonic Acid Resin", Prep. A.C.S. Div. Fuel Chem., 28, (1983), pp. 176-190.
Bhattacharyya, S.K., et al., "High-Pressure Synthesis of Glycolic Acid from Formaldehyde, Carbon Monoxide, and Water in Presence of Nickel, Cobalt, and Iron Catalysts", Advanced Catalysts, 9, (1957), pp. 625-635.
Baniel, A., et al., "Acid-Base Couple Solvents in Recovery of Mineral Acids From Waste Streams", Proceedings of $2^{nd}$ International Conference on Separations Science and Technology, Oct. 1-4, 1989, pp. 667-674.
Wegescheider, Rud., et al., "Addition of Acid Anhydrides to Aldehydes and Ketones", Royal and Imperial University of Vienna, presented at the meeting of Nov. 4, 1909, pp. 1-47.
King, Walter D., et al. "The Acid-Catalyzed Reaction of Acetic Anhydride with Some Oxocanes", Journal of Applied Polymer Science, vol. 18, (1974) pp. 547-554.
He, Dehua, et al., "Condensation of formaldehyde and methyl formate to methyl glycolate and methyl methoxy acetate using heteropolyacids and their salts", Catalysis Today, 51, (1999), pp. 127-134.
U. S. Appl. No. 12/889,045, filed Sep. 23, 2010, Scott Donald Barnicki, et al., now U.S. Pat. No. 8,709,376.
U.S. Appl. No. 12/889,065, filed Sep. 23, 2010 Scott Donald Barnicki, et al., now U.S. Pat. No. 8,466,328.
U.S. Appl. No. 13/208,399, filed Aug. 12, 2011, Scott Donald Barnicki, et al., now U.S. Pat. No. 8,829,248.
U.S. Appl. No. 13/896,706, filed May 17, 2013, Scott Donald Barnicki, et al., now U.S. Pat. No. 8,779,214.
U.S. Appl. No. 13/431,335, filed Mar. 27, 2012, Scott Donald Barnicki, et al., now U.S. Pat. No. 8,785,688.
U.S. Appl. No. 13/431,358, filed Mar. 27, 2012, Scott Donald Barnicki, et al., now U.S. Pat. No. 8,829,234.
U.S. Appl. No. 13/431,369, filed Mar. 27, 2012, Scott Donald Barnicki, et al., now U.S. Pat. No. 8,765,999.
U.S. Appl. No. 13/431,402, filed Mar. 27, 2012, Scott Donald Barnicki, et al., now U.S. Pat. No. 8,926,766.
U.S. Appl. No. 13/431,386, filed Mar. 27, 2012, Scott Donald Barnicki, et al., now U.S. Pat. No. 8,703,999.
U.S. Appl. No. 13/491,954, filed Jun. 8, 2012 Mesfin Ejerssa Janka, now U.S. Pat. No. 9,040,748.
USPTO Notice of Allowance for U.S. Appl. No. 12/889,045 dated Jul. 18, 2012.
USPTO Notice of Allowance for U.S. Appl. No. 12/889,065 dated Oct. 15, 2012.
Malinowski, J. J. "Evaluation of Liquid Extraction Potentials for Downstream Separation of 1,3-Propanediol", Biotechnology Techniques, vol. 18, No. 2 (Jan. 1, 1999), pp. 127-130.
Cox et al. "Mechanistic Studies in Strong Acids . . .", Journal of Organic Chemistry, vol. 51, No. 19 (Sep. 1, 1986), pp. 3619-3624.

(56) References Cited

OTHER PUBLICATIONS

Li et al. "Aqueous Two-phase Extraction of 1,3-propanediol from Glycerol-based Fermentation Broths", Separation and Purification Technology Separation and Purification Technology, vol. 66, No. 3 (May 7, 2009), pp. 472-478.
USPTO Office Action dated Jul. 18, 2013 for U.S. Appl. No. 13/431,386.
USPTO Notice of Allowance for U.S. Appl. No. 13/431,358 dated Aug. 2, 2013.
USPTO Notice of Allowance for U.S. Appl. No. 12/889,045 dated Sep. 19, 2013.
USPTO Notice of Allowance for U.S. Appl. No. 13/896,706 dated Oct. 4, 2013.
USPTO Office Action for U.S. Appl. No. 13/431,358 dated Nov. 12, 2013.
USPTO Notice of Allowance for U.S. Appl. No. 13/896,706 dated Nov. 19, 2013.
USPTO Notice of Allowance for U.S. Appl. No. 13/431,386 dated Dec. 3, 2013.
USPTO Notice of Allowance for U.S. Appl. No. 12/889,045 dated Dec. 13, 2013.
USPTO Office Action for U.S. Appl. No. 13/431,369 dated Jan. 13, 2014.
USPTO Office Action for U.S. Appl. No. 13/208,399 dated Jan. 17, 2014.
USPTO Office Action for U.S. Appl. No. 13/431,402 dated Jan. 31, 2014.
USPTO Notice of Allowance for U.S. Appl. No. 13/896,706 dated Mar. 10, 2014.
USPTO Notice of Allowance for U.S. Appl. No. 13/431,335 dated Mar. 12, 2014.
Bonrath, et al.; "Sustainability, Methantrisulfonic Acid: A Highly Efficient Strongly Acidic Catalyst for Wagner-Meerwein Rearrangement, Friedel-Crafts Alkylation and Acylation Reactions"; Examples from Vitamin E Synthesis, 2009, 1, pp. 161-168.
USPTO Notice of Allowance for U.S. Appl. No. 13/431,358 dated May 16, 2014.
USPTO Notice of Allowance for U.S. Appl. No. 13/208,399 dated May 30, 2014.
USPTO Notice of Allowance for U.S. Appl. No. 13/431,402 dated Sep. 16, 2014.
USPTO Notice of Allowance for U.S. Appl. No. 12/367,190 dated Jan. 12, 2015.

* cited by examiner

PROCESS FOR THE SEPARATION AND PURIFICATION OF A MIXED DIOL STREAM

CROSS REFERENCES TO RELATED APPLICATIONS

This application is a Divisional of U.S. application Ser. No. 13/431,308 filed Mar. 27, 2012 now United States Publication Number 2012-0184783 which is a Continuation-In-Part of U.S. application Ser. No. 12/889,065, filed Sep. 23, 2010 now U.S. Pat. No. 8,466,328, which claims the benefit of U.S. Provisional Application No. 61/374,850, filed Aug. 18, 2010, all of which are incorporated herein by reference in their entireties.

FIELD OF THE INVENTION

This invention relates to a process for the purification of a mixed diol stream. More specifically, this invention relates to the separation of two-, three-, and four-carbon diols. One aspect of this invention relates to a process for the purification of ethylene glycol by the separation of propylene and butylene glycols. Another aspect of this invention relates to the separation of mixtures of propylene glycols from butylene glycols. Further, this invention relates to a process wherein a mixed diol stream may be separated by extraction or extraction and distillation processes.

BACKGROUND OF THE INVENTION

Two-, three-, and four-carbon diols, as exemplified by ethylene glycol, 1,2-propanediol, 1,3-propanediol, 1,2-butanediol, 2,3-butanediol, 1,3-butanediol, and 1,4-butanediol, find use in a myriad of industrially important polymers and formulations. Many processes have been disclosed for the production of these diols. For example, ethylene glycol can be produced by the hydrogenation of glycolic acid, glycolic acid esters, methyl glycolate, oligomers of glycolic acid, oligomers of glycolic acid ester, or mixtures thereof with a ruthenium compound such as, for example, a ruthenium-organophophorus coordination compound, that is soluble or partly soluble in the reaction mixture. Such a glycolic acid-based route has been described in the art as disclosed in U.S. Pat. No. 7,615,671. The hydrogenation of glycolic acid species may also produce by-product higher diols, primarily 1,2-propanediol and 1,2-butanediol, in small quantities, e.g., typically less than 1 weight percent of each compared to ethylene glycol.

Carbohydrate feedstocks also may be used to produce mixed diol streams with varying amounts and particular species of two-carbon diols, three-carbon diols, four-carbon-diols, and higher diols.

It is desirable to separate the mixed diol stream into its component diols in a most economic manner. Distillation, a common method of separation, can prove difficult when components have close boiling points. The normal boiling points of ethylene glycol, 1,2-propanediol, and 1,2-butanediol are 197.1° C., 187.7° C., and 196.5° C. respectively, and ethylene glycol and 1,2-butanediol are known to form a minimum boiling azeotrope, precluding complete separation by single-feed ordinary fractional distillation. Separation of such mixed diol streams into pure fractions by ordinary single-feed fractional distillation is extremely difficult, if not impossible due to numerous azeotropes and close boiling points.

There is a need for a process whereby a diol mixture can be separated into pure fractions in an efficient and cost-effective manner.

SUMMARY OF INVENTION

We have discovered that a mixed diol stream can be efficiently separated into component fractions by extraction. One embodiment of our invention, therefore, is a process for recovering purified ethylene glycol from a mixed diol stream, comprising
(A) extracting the mixed diol stream, comprising
  (i) 1 weight percent to 99.5 weight percent, ethylene glycol;
  (ii) 20 ppm by weight to 99 weight percent of one or more three-carbon diols and four-carbon diols selected from 1,2-propanediol, 1,3-propanediol, 1,2-butanediol, 1,3-butanediol, 1,4-butanediol, and 2,3-butanediol; each based on the total weight of diols, and
  (iii) 0 weight percent to 50 weight percent water, based on the total weight of diols and water, with an extractant, comprising
    (i) a hydrophobic solvent selected from alkanols having from 6 to 20 carbon atoms, ketones having from 5 to 20 carbon atoms, esters having from 5 to 20 carbon atoms, ethers having from 5 to 20 carbon atoms, carboxylic acids having from 5 to 20 carbon atoms, trialkylphosphine oxides having from 18 to 48 carbon atoms, and mixtures thereof; and
    (ii) optionally, a second modifying hydrophobic solvent selected from hydrocarbons having from 5 to 20 carbon atoms; to form a raffinate phase comprising a major amount of the ethylene glycol and a minor amount of the three-carbon diols and/or four-carbon diols contained in the mixed diol stream and an extract phase comprising a major amount of the three-carbon diols and/or four-carbon diols and a minor amount of the ethylene glycol contained in the mixed diol stream; and
(B) separating the raffinate phase and the extract phase.

A second embodiment of our invention is a process for recovering purified ethylene glycol from a mixed diol stream, comprising
(A) extracting the mixed diol stream, comprising
  (i) 20 weight percent to 99.5 weight percent, ethylene glycol;
  (ii) 20 ppm by weight to 40 weight percent of one or more three-carbon diols selected from 1,2-propanediol and 1,3-propanediol, and 20 ppm by weight to 30 weight percent of one or more four-carbon diols selected from 1,2-butanediol, 1,3-butanediol, 1,4-butanediol, and 2,3-butanediol; each based on the total weight of diols, and
  (iii) 5 weight percent to 35 weight percent water, based on the total weight of diols and water, with an extractant, comprising
    (i) a hydrophobic solvent selected from 2-ethylhexanol, cyclohexanol, n-hexanol, methyl isobutyl ketone, methyl isopropyl ketone, methyl propyl ketone, diisobutyl ketone, trioctylphosphine oxide, trihexylphosphine oxide, and mixtures thereof; and
    (ii) optionally, a second modifying hydrophobic solvent selected from hexane, heptane, octane, decane, benzene, toluene, xylenes, isoparaffinic mixed hydrocarbons having a boiling range between 90 and 325° C., methyl napththalenes, and mixtures thereof; to form a raffinate phase comprising a major amount of the ethylene glycol and a minor amount of the three-carbon diols and/or four-carbon diols contained in the mixed diol stream and an extract phase comprising a major amount of the three-carbon diols and/or four-carbon diols and a minor amount of the ethylene glycol contained in the mixed diol stream; and
(B) separating the raffinate phase and the extract phase.

A third embodiment of our invention, is a process for recovering purified ethylene glycol from a mixed diol stream comprising ethylene glycol and four-carbon diols, comprising
(A) extracting the mixed diol stream, comprising
  (i) 50 weight percent to 99.99 weight percent, ethylene glycol;
  (ii) 0.01 weight percent to 50 weight percent of one or more four-carbon diols selected from 1,2-butanediol, 1,3-butanediol, 1,4-butanediol, and 2,3-butanediol; each based on the total weight of diols, and
  (iii) 0 weight percent to 50 weight percent water, based on the total weight of diols and water, with an extractant, comprising
    (i) a hydrophobic solvent selected from alkanols having from 6 to 20 carbon atoms, ketones having from 5 to 20 carbon atoms, esters having from 5 to 20 carbon atoms, ethers having from 5 to 20 carbon atoms, carboxylic acids having from 5 to 20 carbon atoms, trialkylphosphine oxides having from 18 to 48 carbon atoms, and mixtures thereof; and
    (ii) optionally, a second modifying hydrophobic solvent selected from hydrocarbons having from 5 to 20 carbon atoms; to form a raffinate phase comprising a major amount of the ethylene glycol and a minor amount of the four-carbon diols contained in the mixed diol stream and an extract phase comprising a major amount of the four-carbon diols and a minor amount of the ethylene glycol contained in the mixed diol stream; and
(B) separating the raffinate phase and the extract phase.

Our process can also be used, for example, to separate glycols from the hydrogenolysis of glycerol. A fourth embodiment of our invention, is a process for recovering diols from a mixed diol stream, comprising
(A) extracting the mixed diol stream, comprising
  (i) 0.1 weight percent to 50 weight percent of one or more diols selected from ethylene glycol, 1,2-propanediol, 1,3-propanediol 1,2-butanediol, 1,3-butanediol, 1,4-butanediol, and 2,3-butanediol;
  (ii) 5 weight percent to 90 weight percent glycerol; and
  (iii) 5 weight percent to 90 weight percent water; each based on the total weight of the mixed diol stream with an extractant, comprising
    (i) a hydrophobic solvent selected from alkanols having from 6 to 20 carbon atoms, ketones having from 5 to 20 carbon atoms, esters having from 5 to 20 carbon atoms, ethers having from 5 to 20 carbon atoms, carboxylic acids having from 5 to 20 carbon atoms, trialkylphosphine oxides having from 18 to 48 carbon atoms, and mixtures thereof; and
    (ii) optionally, a second modifying hydrophobic solvent selected from hydrocarbons having from 5 to 20 carbon atoms; to form a raffinate phase comprising a major amount of the glycerol and a minor amount of the diols contained in the mixed diol stream and an extract phase comprising a major amount of the diols and a minor amount of the glycerol contained in the mixed diol stream; and
(B) separating the raffinate phase and the extract phase.

Our process can also be used, for example, to separate glycols from a fermentation broth. A fifth embodiment of our invention, is a process for recovering diols from a mixed diol stream, comprising
(A) extracting the mixed diol stream, comprising
  (i) 0.1 weight percent to 30 weight percent of ethylene glycol, 1,2-propanediol and 1,3-propanediol, 1,2-butanediol, 1,3-butanediol, 1,4-butanediol, and 2,3-butanediol;
  (ii) 5 to 50 weight percent glucose; and
  (iii) 50 weight percent to 90 weight percent water; each based on the total weight of the mixed diol stream, with an extractant, comprising
    (i) a hydrophobic solvent selected from alkanols having from 6 to 20 carbon atoms, ketones having from 5 to 20 carbon atoms, esters having from 5 to 20 carbon atoms, ethers having from 5 to 20 carbon atoms, carboxylic acids having from 5 to 20 carbon atoms, trialkylphosphine oxides having from 18 to 48 carbon atoms, and mixtures thereof; and
    (ii) optionally, a second modifying hydrophobic solvent selected from hydrocarbons having from 5 to 20 carbon atoms; to form a raffinate phase comprising a major amount of the glucose and a minor amount of the diols contained in the mixed diol stream and an extract phase comprising a major amount of the diols and a minor amount of the glucose contained in the mixed diol stream; and
(B) separating the raffinate phase and the extract phase.

A sixth embodiment of our invention, is a process for recovering purified three-carbon diols from a mixed diol stream, comprising
(A) extracting the mixed diol stream, comprising
  (i) 1 weight percent to 99.5 weight percent of one or more three-carbon diols selected from 1,2-propanediol and 1,3-propanediol;
  (ii) 20 ppm by weight to 99 weight percent of one or more four-carbon diols selected from 1,2-butanediol, 1,3-butanediol, 1,4-butanediol, and 2,3-butanediol; each based on the total weight of diols, and
  (iii) 0 weight percent to 50 weight percent water, based on the total weight of diols and water, with an extractant, comprising
    (i) a hydrophobic solvent selected from alkanols having from 6 to 20 carbon atoms, ketones having from 5 to 20 carbon atoms, esters having from 5 to 20 carbon atoms, ethers having from 5 to 20 carbon atoms, carboxylic acids having from 5 to 20 carbon atoms, trialkylphosphine oxides having from 18 to 48 carbon atoms, and mixtures thereof; and
    (ii) optionally, a second modifying hydrophobic solvent selected from hydrocarbons having from 5 to 20 carbon atoms; to form a raffinate phase comprising a major amount of the three-carbon diols and a minor amount of the four-carbon diols contained in the mixed diol stream and an extract phase comprising a major amount of the four-carbon diols and a minor amount of the three-carbon diols contained in the mixed diol stream; and
(B) separating the raffinate phase and the extract phase.

DETAILED DESCRIPTION

Figure 1:
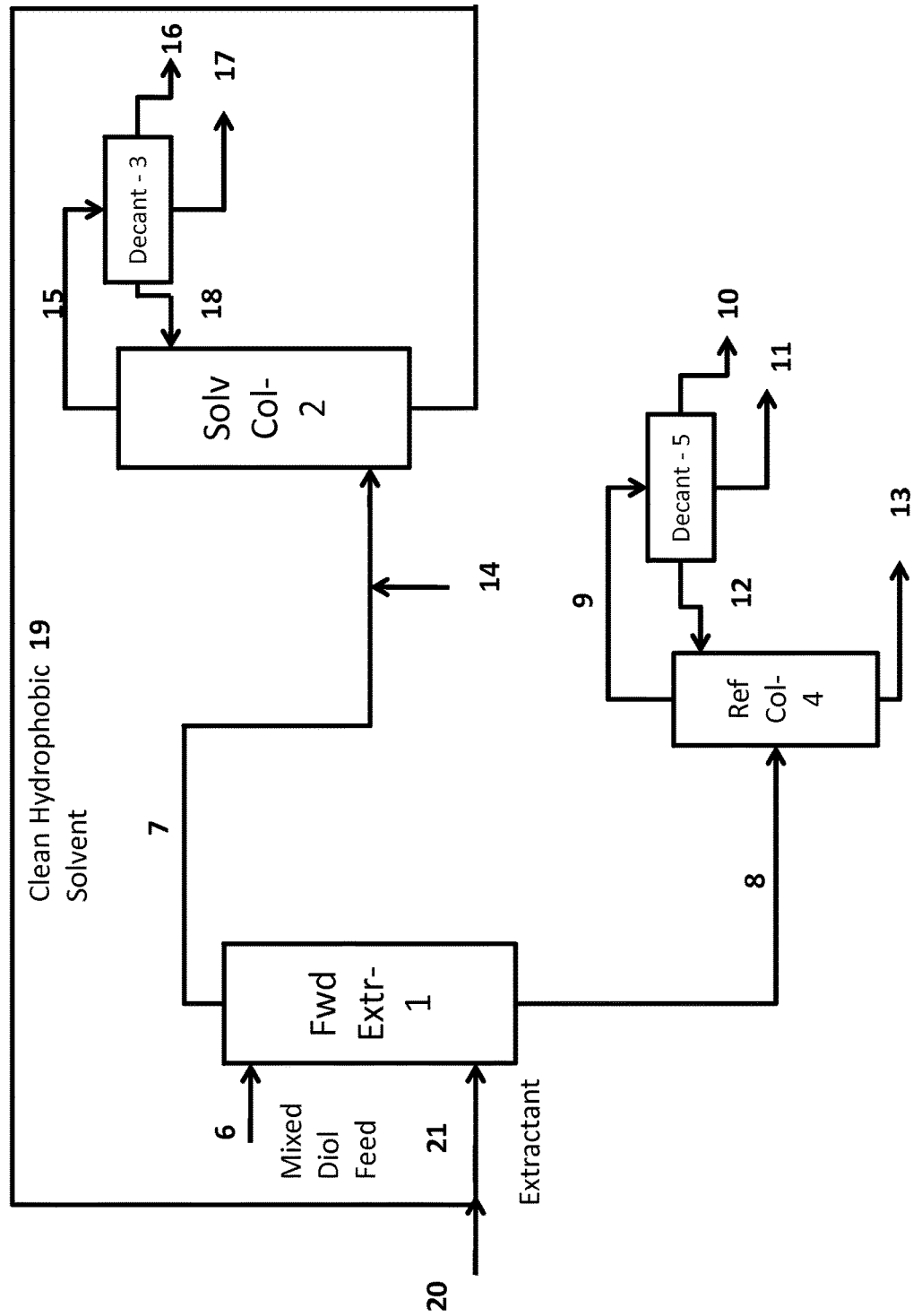
FIG. 1 is a schematic flow diagram of one embodiment of the invention in which a mixed diol stream is subjected to forward extraction with a hydrophobic solvent to produce a raffinate containing ethylene glycol which is subject to purification via distillation and an extract which is purified via distillation and recycled to the forward extraction step.

The present invention provides a method to separate two-, three-, and four-carbon diols from a mixed diol stream, comprising
(A) extracting the mixed diol stream, comprising
 (i) 1 weight percent to 99.5 weight percent, ethylene glycol;
 (ii) 20 ppm by weight to 99 weight percent of one or more three-carbon diols and four-carbon diols selected from 1,2-propanediol, 1,3-propanediol, 1,2-butanediol, 1,3-butanediol, 1,4-butanediol, and 2,3-butanediol; each based on the total weight of diols, and
 (iii) 0 weight percent to 50 weight percent water, based on the total weight of diols and water, with an extractant, comprising
 (i) a hydrophobic solvent selected from alkanols having from 6 to 20 carbon atoms, ketones having from 5 to 20 carbon atoms, esters having from 5 to 20 carbon atoms, ethers having from 5 to 20 carbon atoms, carboxylic acids having from 5 to 20 carbon atoms, trialkylphosphine oxides having from 18 to 48 carbon atoms, and mixtures thereof; and
 (ii) optionally, a second modifying hydrophobic solvent selected from hydrocarbons having from 5 to 20 carbon atoms; to form a raffinate phase comprising a major amount of the ethylene glycol and a minor amount of the three-carbon diols and/or four-carbon diols contained in the mixed diol stream and an extract phase comprising a major amount of the three-carbon diols and/or four-carbon diols and a minor amount of the ethylene glycol contained in the mixed diol stream; and
(B) separating the raffinate phase and the extract phase.

Unless otherwise indicated, all numbers expressing quantities of ingredients, properties such as molecular weight, reaction conditions, and so forth used in the specification and claims are to be understood as being modified in all instances by the term "about." Accordingly, unless indicated to the contrary, the numerical parameters set forth in the following specification and attached claims are approximations that may vary depending upon the desired properties sought to be obtained by the present invention. At the very least, each numerical parameter should at least be construed in light of the number of reported significant digits and by applying ordinary rounding techniques. Further, the ranges stated in this disclosure and the claims are intended to include the entire range specifically and not just the endpoint(s). For example, a range stated to be 0 to 10 is intended to disclose all whole numbers between 0 and 10 such as, for example 1, 2, 3, 4, etc., all fractional numbers between 0 and 10, for example 1.5, 2.3, 4.57, 6.1113, etc., and the endpoints 0 and 10. Also, a range associated with chemical substituent groups such as, for example, "$C_1$ to $C_5$ hydrocarbons", is intended to specifically include and disclose $C_1$ and $C_5$ hydrocarbons as well as $C_2$, $C_3$, and $C_4$ hydrocarbons.

Also, it is to be understood that the mention of one or more process steps does not preclude the presence of additional process steps before or after the combined recited steps or intervening process steps between those steps expressly identified. Moreover, the lettering of process steps or ingredients is a convenient means for identifying discrete activities or ingredients and the recited lettering can be arranged in any sequence, unless otherwise indicated.

As used herein, the term "and/or," when used in a list of two or more items, means that any one of the listed items can be employed by itself, or any combination of two or more of the listed items can be employed. For example, if a composition is described as containing components A, B, and/or C, the composition can contain A alone; B alone; C alone; A and B in combination; A and C in combination; B and C in combination; or A, B, and C in combination.

As used herein, the term "feed" is intended to have its commonly understood meaning in the liquid-liquid extraction art, which is the solution that contains the materials to be extracted or separated. In the present invention, one example of a "feed" is a mixture comprised of two or more of ethylene glycol, 1,2-propanediol, 1,3-propanediol, 1,2-butanediol, 2,3-butanediol, 1,3-butandediol, and 1,4-butanediol. In the present invention the term feed is synonymous with "mixed diol stream". The term "extraction solvent," as used herein, is intended to be synonymous with the term "extractant" or "solvent" and is intended to mean the immiscible liquid that is used in the extraction process to extract materials or solutes from the feed. The term "extract" is the immiscible liquid left from the extraction solvent after it has been contacted with the feed. The term "raffinate" is intended to mean the liquid phase left from the feed after it has been contacted with the extraction solvent. The term "wash solvent" is understood to mean a liquid used to wash or enhance the purity of the raffinate or extract phase.

In the present invention, one example of an extraction solvent is an alkanol containing 6 to 20 carbon atoms such as, for example, 2-ethylhexanol. The term "alkanol", as used herein, refers to an alkyl containing 6 to 20 carbon atoms and at least one OH moiety. Other examples of extraction solvents are "ketones", "esters", "ethers", "carboxylic acids", and "hydrocarbons" which are terms well known to those skilled in the art. The extraction solvent can also contain trialkylphosphine oxides. The term "trialkylphosphine oxides", as used herein, refers to phosphine oxides containing three alkyl moieties with a total of 18 to 48 carbon atoms including, but not limited to, trioctylphosphine oxide, isomeric 24-carbon phosphine oxides, trihexylphosphine oxide, and isomeric 18-carbon phosphine oxides. The term "hydrophobic solvent", as used herein, refers to a solvent that will phase separate when mixed with the mixed diol stream and/or water. The term a "major amount", as used herein, for example "a major amount of ethylene glycol contained in the mixed diol stream" refers to at least 50 weight percent of the ethylene glycol contained in the mixed diol stream. In a further example, when a raffinate phase comprises a major amount of the ethylene glycol in the mixed diol stream, the weight of the ethylene glycol in the raffinate phase divide by the weight of the ethylene glycol in the mixed diol stream, on a weight percent basis, is greater than 50 weight percent. The term a "minor amount", as used herein, for example "a minor amount of ethylene glycol contained in the mixed diol stream" refers to less than 50 weight percent of the ethylene glycol contained in the mixed diol stream.

The process of the invention provides for the separation of a mixed diol stream. The term "mixed diol stream", as used herein, is understood to mean a mixture comprising two or more of ethylene glycol, 1,2-propanediol, 1,3-propanediol, 1,2-butanediol, 2,3-butanediol, 1,3-butandediol, and 1,4-butanediol. The terms "propanediols" and "three-carbon diols", as used herein, are understood to mean a mixture comprising one or more of 1,2-propanediol and 1,3-propanediol. The terms "butanediols" and "four-carbon diols", as used herein, are understood to mean a mixture comprising one or more of 1,2-butanediol, 2,3-butanediol, 1,3-butandediol, and 1,4-butanediol. The term "based on the total weight of diols", as used herein, is understood to mean based on the summation of the amount of ethylene glycol, three-carbon diols, and four-carbon diols.

The mixed diol stream of the present invention can be produced by a variety of reaction methods including, but not limited to hydrogenation of glycolic acid, glycolate esters, oligomers of glycolic acid, esters of glycolic acid oligomers, or mixtures thereof, for example, as disclosed in U.S. Pat. No. 7,615,671; hydrogenolysis of carbohydrates, such as sucrose, glucose, fructose, cellulose, sorbitol, or mixtures thereof, as disclosed, for example in U.S. Pat. Nos. 5,210,335, 5,026,927, 6,291,725, and U.S. Pat. Appl. No. 2007123739; hydrogenolysis of glycerol, as exemplified by U.S. Pat. Nos. 5,276,181, 5,214,219, and U.S. Pat. Pub. No. 2007123739.

The mixed diol stream of the present invention may be derived from the reaction methods described above, but also may have undergone prior separation methods to prepurify the mixed diol stream. For example a reactor effluent from the hydrogenation of glycolate species may undergo distillation to remove low boilers, such as methanol, or high boilers, such as unreacted glycolic acid oligomers. Alternatively, at times it may be advantageous to remove the lowest boiling, non-azeotrope forming propanediols from a reactor effluent by single-feed fractional distillation, prior to the extraction steps of the present invention.

Our process comprises extracting a mixed diol stream that comprises about 1 to about 99.5 weight percent ethylene glycol and about 20 ppm to 99 weight percent of one or more three-carbon and four-carbon diols selected from 1,2-propanediol, 1,3-propanediol, 1,2-butanediol, 2,3-butanediol, 1,3-butandediol, and 1,4-butanediol, each based on the total weight of diols; and 0 weight percent to 50 weight percent water, based on the total weight of diols and water. In another example, the mixed diol stream, derived by the hydrogenolysis of sorbitol, comprises about 9 to about 23 weight percent butanediols (1,2-/1,3-/1,4-/2,3-butanediols), 32 to about 67 weight percent 1,2-propanediol, and about 24 to about 59 weight percent ethylene glycol. In another example, the mixed diol stream, derived by the hydrogenolysis of sorbitol glycerol, comprises about 40 to 90 weight percent 1,2-propanediol, about 10 to about 60 weight percent ethylene glycol, and about 0.1 to about 10 weight percent 1,2-butanediol. In a further example, the mixed diol stream, derived from the hydrogenolysis of sucrose, comprises about 50 to about 65 weight percent 1,2-propanediol, about 28 to about 45 weight percent ethylene glycol, and about 5 to about 7 weight percent 1,2-butanediol. In yet another example, the mixed diol stream, derived from a prepurification step in which the 1,2-propanediol has been removed by ordinary single-feed distillation, comprises about 50 to about 99.99 weight percent ethylene glycol, and about 0.01 to about 50 weight percent butanediols.

In an aspect of the invention, the mixed diol stream comprises 1 weight percent to 99.5 weight percent ethylene glycol, 1 weight percent to 90 weight percent ethylene glycol; 1 weight percent to 80 weight percent ethylene glycol, 1 weight percent to 70 weight percent ethylene glycol, 10 weight percent to 99.5 weight percent ethylene glycol, 10 weight percent to 90 weight percent ethylene glycol, 10 weight percent to 80 weight percent ethylene glycol, 10 weight percent to 70 weight percent ethylene glycol, 20 weight percent to 99.5 weight percent ethylene glycol, 20 weight percent to 90 weight percent ethylene glycol, 20 weight percent to 80 weight percent ethylene glycol, 20 weight percent to 70 weight percent ethylene glycol, or 20 weight percent to 60 weight percent ethylene glycol; 20 ppm to 99.5 weight percent three-carbon diols and four-carbon diols, 20 ppm to 90 weight percent three-carbon diols and four-carbon diols, 20 ppm to 80 weight percent three-carbon diols and four-carbon diols, 20 ppm to 60 weight percent three-carbon diols and four-carbon diols, 20 ppm to 40 weight percent three-carbon diols and four-carbon diols, 20 ppm to 30 weight percent three-carbon diols and four-carbon diols, 20 ppm to 5 weight percent three-carbon diols and four-carbon diols, 20 ppm to 2 weight percent three-carbon diols and four-carbon diols, 0.1 weight percent to 99.5 weight percent three-carbon diols and four-carbon diols, 0.1 weight percent to 90 weight percent three-carbon diols and four-carbon diols, 0.1 weight percent to 80 weight percent three-carbon diols and four-carbon diols, 0.1 weight percent to 60 weight percent three-carbon diols and four-carbon diols, 0.1 weight percent to 40 weight percent three-carbon diols and four-carbon diols, 0.1 weight percent to 30 weight percent three-carbon diols and four-carbon diols, 0.1 weight percent to 5 weight percent three-carbon diols and four-carbon diols, or 0.1 weight percent to 2 weight percent three-carbon diols and four-carbon diols, each based on the total weight of diols.

In another aspect of the invention, the mixed diol stream comprises 1 weight percent to 99.5 weight percent ethylene glycol, 1 weight percent to 90 weight percent ethylene glycol, 1 weight percent to 80 weight percent ethylene glycol, 1 weight percent to 70 weight percent ethylene glycol, 10 weight percent to 99.5 weight percent ethylene glycol, 10 weight percent to 90 weight percent ethylene glycol, 10 weight percent to 80 weight percent ethylene glycol, 10 weight percent to 70 weight percent ethylene glycol, 20 weight percent to 99.5 weight percent ethylene glycol, 20 weight percent to 90 weight percent ethylene glycol, 20 weight percent to 80 weight percent ethylene glycol, 20 weight percent to 70 weight percent ethylene glycol, or 20 weight percent to 60 weight percent ethylene glycol; 20 ppm to 60 weight percent three-carbon diols, 20 ppm to 40 weight percent three-carbon diols, 20 ppm to 30 weight percent three-carbon diols, 20 ppm to 5 weight percent three-carbon diols, 20 ppm to 2 weight percent three-carbon diols, 0.1 weight percent to 60 weight percent three-carbon diols, 0.1 weight percent to 40 weight percent three-carbon diols, 0.1 weight percent to 30 weight percent three-carbon diols, 0.1 weight percent to 20 weight percent three-carbon diols, 0.1 weight percent to 5 weight percent three-carbon diols, 0.1 weight percent to 2 weight percent three-carbon diols; and 20 ppm to 60 weight percent four-carbon diols, 20 ppm to 40 weight percent four-carbon diols, 20 ppm to 30 weight percent four-carbon diols, 20 ppm to 20 weight percent four-carbon diols, 20 ppm to 5 weight percent four-carbon diols, 20 ppm to 2 weight percent four-carbon diols, 0.1 weight percent to 60 weight percent four-carbon diols, 0.1 weight percent to 40 weight percent four-carbon diols, 0.1 weight percent to 30 weight percent four-carbon diols, 0.1 weight percent to 20 weight percent four-carbon diols, 0.1 weight percent to 5 weight percent four-carbon diols, or 0.1 weight percent to 2 weight percent four-carbon diols, each based on the total weight of diols.

In another aspect of the invention, the mixed diol stream comprises 5 to 75 weight percent ethylene glycol, 30 weight percent to 95 weight percent three-carbon diols, and 20 ppm to 10 weight percent four-carbon diols; or 10 weight percent to 60 weight percent ethylene glycol, 40 weight percent to 90 weight percent 1,2-propanediol, and 0.1 weight percent to 10 weight percent 1,2-butanediol, each based on the total weight of diols.

In another aspect of the invention, the mixed diol stream comprises 20 weight percent to 50 weight percent ethylene glycol, 45 weight percent to 70 weight percent three-carbon diols, and 1 weight percent to 10 weight percent four-carbon diols; or 28 weight percent to 45 weight percent ethylene glycol, 50 weight percent to 65 weight percent 1,2-propanediol, and 5 weight percent to 7 weight percent 1,2-butanediol, each based on the total weight of diols.

In another aspect of the invention, the mixed diol stream comprises 10 weight percent to 60 weight percent ethylene glycol, 25 weight percent to 75 weight percent three-carbon diols, and 5 weight percent to 25 weight percent four-carbon diols; or 20 weight percent to 50 weight percent ethylene glycol, 30 weight percent to 70 weight percent 1,2-propanediol, and 5 weight percent to 25 weight percent four-carbon diols, each based on the total weight of diols.

In another aspect of the invention, the mixed diol stream comprises 40 weight percent to 99.99 weight percent ethylene glycol, 40 weight percent to 99 weight percent ethylene glycol, 40 weight percent to 90 weight percent ethylene glycol, 40 weight percent to 80 weight percent ethylene glycol, 50 weight percent to 99.99 weight percent ethylene glycol, 50 weight percent to 99 weight percent ethylene glycol, 50 weight percent to 90 weight percent ethylene glycol, or 50 weight percent to 80 weight percent ethylene glycol; and 0.001 weight percent to 60 weight percent four-carbon diols, 0.001 weight percent to 50 weight percent four-carbon diols, 0.001 weight percent to 40 weight percent four-carbon diols, 0.001 weight percent to 30 weight percent four-carbon diols, 0.001 weight percent to 20 weight percent four-carbon diols, 0.01 weight percent to 60 weight percent four-carbon diols, 0.01 weight percent to 50 weight percent four-carbon diols, 0.01 weight percent to 40 weight percent four-carbon diols, 0.01 weight percent to 30 weight percent four-carbon diols, 0.01 weight percent to 20 weight percent four-carbon diols, 1 weight percent to 60 weight percent four-carbon diols, 1 weight percent to 50 weight percent four-carbon diols, 1 weight percent to 40 weight percent four-carbon diols, 1 weight percent to 30 weight percent four-carbon diols, or 1 weight percent to 20 weight percent four-carbon diols, each based on the total weight of diols.

In another aspect of the invention, the mixed diol stream comprises 1 weight percent to 99.99 weight percent three-carbon diols, 1 weight percent to 99 weight percent three-carbon diols, 1 weight percent to 90 weight percent three-carbon diols, 1 weight percent to 80 weight percent three-carbon diols, 10 weight percent to 99.99 weight percent three-carbon diols, 10 weight percent to 99 weight percent three-carbon diols, 10 weight percent to 90 weight percent three-carbon diols, 10 weight percent to 80 weight percent three-carbon diols; and 20 ppm to 99.99 weight percent four-carbon diols, 20 ppm to 99 weight percent four-carbon diols, 20 ppm to 90 weight percent four-carbon diols, 20 ppm to 80 weight percent four-carbon diols, 0.001 weight percent to 99.99 weight percent four-carbon diols, 0.001 weight percent to 99 weight percent four-carbon diols, 0.001 weight percent to 90 weight percent four-carbon diols, 0.001 weight percent to 80 weight percent four-carbon diols, 0.01 weight percent to 99 weight percent four-carbon diols, 0.01 weight percent to 90 weight percent four-carbon diols, 0.01 weight percent to 80 weight percent four-carbon diols, 0.01 weight percent to 70 weight percent four-carbon diols, 1 weight percent to 99 weight percent four-carbon diols, 1 weight percent to 90 weight percent four-carbon diols, 1 weight percent to 80 weight percent four-carbon diols, or 1 weight percent to 70 weight percent four-carbon diols, each based on the total weight of diols.

In another aspect of the invention, any of the mixed diol streams above can further comprise water. The water can be present in the mixed diol stream as received or may be added to the mixed diol stream. The amount of water, based on the total amount of diols and water, for example, can range from 0.5 weight percent to 80 weight percent water, 0.5 weight percent to 50 weight percent water, 0.5 weight percent to 40 weight percent water, 0.5 weight percent to 25 weight percent water, 1 weight percent to 80 weight percent water, 1 weight percent to 50 weight percent water, 1 weight percent to 40 weight percent water, 1 weight percent to 25 weight percent water, 5 weight percent to 80 weight percent water, 5 weight percent to 60 weight percent water, 5 weight percent to 50 weight percent water, 5 weight percent to 40 weight percent water, 5 weight percent to 35 weight percent water, 5 weight percent to 25 weight percent water, 5 weight percent to 15 weight percent water, 10 weight percent to 50 weight percent water, or 10 weight percent to 25 weight percent water.

The mixed diol stream is contacted with an extractant that comprises at least one hydrophobic solvent selected from alkanols having from 6 to 20 carbon atoms, ketones having from 5 to 20 carbon atoms, esters having from 5 to 20 carbon atoms, ethers having from 5 to 20 carbon atoms, alkyl carbonate esters having from 3 to 20 carbon atoms, trialkylphosphine oxides having from 18 to 48 carbon atoms, and mixtures thereof. Some representative examples of hydrophobic solvents include, but are not limited to, 2-ethylhexanol, n-heptanol, n-hexanol, cyclohexanol, 4-methyl-2-pentanol, n-octanol, n-nonanol, n-decanol, tetradecanol isomers, 3-methyl-2-butanone, methyl isobutyl ketone (also known as 4-methyl-2-pentanone), methyl isopropyl ketone, methyl propyl ketone, diisobutyl ketone, isobutylisobutyrate, ethyl acetate, n-butyl acetate, isobutylacetate, isopropylacetate, n-propyl acetate, diisopropylether, dibutylether, tertiary-amyl methyl ether, tertiary-butyl methyl ether, trioctylphosphine oxide and isomeric 24-carbon phosphine oxides, trihexylphosphine oxide and isomeric 18-carbon phosphine oxides, and mixtures thereof. For example, in one aspect of our inventive process, the hydrophobic extraction solvent comprises 2-ethylhexanol. In another aspect of our inventive process, the hydrophobic extraction solvent comprises trioctylphosphine oxide, trihexylphosphine oxide, and/or isomeric 24-carbon and 18-carbon phosphine oxides, as exemplified by the CYANEX® solvents, such as CYANEX® 923 and CYANEX®921 (available from Cytec Industries, Inc., 5 Garret Mountain Plaza, Woodland Park, N.J.). In one aspect of the invention, the hydrophobic solvent may be selected from 2-ethylhexanol, cyclohexanol, n-hexanol, methyl isobutyl ketone, methyl isopropyl ketone, methyl propyl ketone, diisobutyl ketone, propylene carbonate, trioctylphosphine oxide, trihexylphosphine oxide, and mixtures thereof. The hydrophobic solvent may be selected from 2-ethylhexanol, cyclohexanol, n-hexanol, methyl isobutyl ketone, methyl isopropyl ketone, methyl propyl ketone, diisobutyl ketone, trioctylphosphine oxide, trihexylphosphine oxide, and mixtures thereof. The hydrophobic solvent may be selected from 2-ethylhexanol, cyclohexanol, trioctylphosphine oxide, trihexylphosphine oxide and mixtures thereof.

Mixtures of one or more different hydrophobic solvents may be employed if desired. The amount of hydrophobic extraction solvent employed is not critical to the subject invention and need only be that amount sufficient to extract the one or more diols from the mixed diol stream for any given process and to ensure the formation of two immiscible liquid phases throughout the extraction zones. In general, the amount of hydrophobic extraction solvent employed may range from about 10 percent by weight up to about 500 percent by weight or more based on the total weight of the mixed diol stream. The use of the high percentage of hydrophobic extraction solvent may be necessary, for example, when there are only a limited number of stages in a counter-current extraction process.

The hydrophobic solvent of the extractant may further comprise a second modifying hydrophobic solvent to modify the physical and transport properties of the extractant. The second modifying hydrophobic solvent can be selected from hydrocarbons having from 5 to 20 carbon atoms. Some representative examples of hydrocarbons include hexane, heptane, octane, decane, benzene, toluene, xylenes, methyl napththalenes, and mixtures thereof. For example, the hydrocarbon may comprise isoparaffinic mixed hydrocarbons having boiling ranges between about 90 and about 325° C., as exemplified by the ISOPAR™ solvents (available from Exxon Chemical Co., Houston, Tex.), such as ISOPAR C (boiling point range of 98 to 104° C.), ISOPAR E (boiling point range of 118 to 137° C.), ISOPAR G (boiling point range of 160 to 176° C.), ISOPAR H (boiling point range of 178 to 188° C.), ISOPAR K (boiling point range of 178 to 197° C.), ISOPAR L (boiling point range of 189 to 207° C.), ISOPAR M (boiling point range of 223 to 254° C.), and ISOPAR V (boiling point range of 273 to 312° C.).

In some aspects of the invention, the hydrocarbon can be lower boiling than the other hydrophobic solvent components and, thus, can be readily separated from the other components by distillation. If more than one hydrophobic solvent is used as the extractant, these solvents may or may not form azeotropic mixtures under distillation conditions employed.

The relative amounts of the hydrophobic solvent and the second modifying hydrophobic solvent can be varied to optimize the extraction. In an aspect of the invention, the extractant comprises 50 weight percent to 100 weight percent of the hydrophobic solvent and 0 weight percent to 50 weight percent of the second, modifying hydrophobic solvent; 50 weight percent to 95 weight percent of the hydrophobic solvent and 5 weight percent to 50 weight percent of the second, modifying hydrophobic solvent; 60 weight percent to 95 weight percent of the hydrophobic solvent and 5 weight percent to 40 weight percent of the second, modifying hydrophobic solvent, or 70 weight percent to 90 weight percent of the hydrophobic solvent and 10 weight percent to 30 weight percent of the second, modifying hydrophobic solvent.

An example, hydrophobic solvent mixture comprises an alcohol selected from cyclohexanol, n-hexanol, n-octanol, 4-methyl-2-pentanol, 2-ethylhexanol; and a hydrocarbon selected from one or more of C9 to C11 alkanes such as n-nonane, n-decane, n-undecane, ISOPAR G (boiling point range of 160 to 176° C.), ISOPAR H (boiling point range of 178 to 188° C.), ISOPAR K (boiling point range of 178 to 197° C.), ISOPAR L (boiling point range of 189 to 207° C.), or mixtures thereof. Another example hydrophobic solvent mixture comprises isomeric trioctylphosphine oxide, isomeric trihexylphosphine oxide, and mixtures thereof, and a hydrocarbon selected from one or more of C9 to C11 alkanes such as n-nonane, n-decane, n-undecane, ISOPAR G (boiling point range of 160 to 176° C.), ISOPAR H (boiling point range of 178 to 188° C.), ISOPAR K (boiling point range of 178 to 197° C.), ISOPAR L (boiling point range of 189 to 207° C.), or mixtures thereof.

If an alcohol is used as the hydrophobic solvent of the extractant, then at least 5 weight percent water, based on total weight of mixed diol stream and water, must be introduced into the first extraction zone to ensure two phases form in the extractor. In another aspect, wherein an alcohol is used as the hydrophobic solvent, the amount of water introduced is 5 to 60 weight percent, based on total weight of mixed diol stream and water. In yet another aspect, wherein an alcohol is used as the hydrophobic solvent, the amount of water introduced is 10 to 50 weight percent based on total weight of mixed diol stream and water.

As noted above, the optional water introduced into the first extraction can be present in the mixed diol stream as received. The optional water can be introduced to the extraction process at one or more different locations. In one aspect for example, the optional water can be added to the mixed diol stream. In another aspect, the water can be introduced into the extractor as a separate feed. In yet another aspect, the extractor may be operated as a fractional extractor with one or more water feed points.

The process of the present invention forms a raffinate phase comprising a major amount of ethylene glycol and a minor amount of three-carbon diols and/or four-carbon diols contained in the mixed diol stream. In an aspect of the invention, greater than 95 weight percent of the ethylene glycol in the mixed diol stream is recovered in the raffinate phase. In another aspect, greater than 98 weight percent, greater than 99 weight percent, greater than 99.5 weight percent, or greater than 99.99 weight percent of the ethylene glycol in the mixed diol stream is recovered in the raffinate phase.

The process of the present invention forms an extract phase comprising a major amount of the three-carbon diols and/or the four-carbon diols and a minor amount of the ethylene glycol. In an aspect of the invention greater than 60 weight percent of the four-carbon diols in the mixed diol stream is recovered in the extract phase. In another aspect, greater than 70 weight percent, greater than 80 weight percent, greater than 90 weight percent, greater than 95 weight percent, greater than 98 weight percent, or greater than 99 weight percent of the four-carbon diols in the mixed diol stream is recovered in the extract phase.

The raffinate phase can be concentrated in ethylene glycol. The concentration of ethylene glycol, based on the total weight of diols in the raffinate phase can be greater than 95 weight percent, or greater than 98 weight percent, or greater than 99 weight percent, or greater than 99.9 weight percent, or greater than 99.99 weight percent. The concentration of three-carbon diols and four-carbon diols, based on the total weight of diols in the raffinate phase, can be less than 5 weight percent, less than 1 weight percent, less than 0.5 weight percent, less than 1000 ppm on a weight basis, less than 500 ppm on a weight basis, less than 100 ppm on a weight basis, or less than 50 ppm on a weight basis.

The extraction of the mixed diol stream can be carried out by any means known in the art to intimately contact two immiscible liquid phases and to separate the resulting phases after the extraction procedure. For example, the extraction can be carried out using columns, centrifuges, mixer-settlers, and miscellaneous devices. Some representative examples of extractors include unagitated columns (e.g., spray, baffle tray and packed, perforated plate), agitated columns (e.g., pulsed, rotary agitated, and reciprocating plate), mixer-settlers (e.g., pump-settler, static mixer-settler, and agitated mixer-settler), centrifugal extractors (e.g., those produced by Robatel, Luwesta, deLaval, Dorr Oliver, Bird, CINC, and Podbielniak), and other miscellaneous extractors (e.g., emulsion phase contactor, electrically enhanced extractors, and membrane extractors). A description of these devices can be found in the "Handbook of Solvent Extraction", Krieger Publishing Company, Malabar, Fla., 1991, pp. 275-501. The various types of extractors may be used alone or in any combination.

The extraction may be conducted in one or more stages. The number of extraction stages can be selected in consideration of capital costs, achieving high extraction efficiency, ease of operability, and the stability of the starting materials and mixed diol stream to the extraction conditions. The extraction also can be conducted in a batch or continuous mode of operation. In a continuous mode, the extraction may be carried out in a co-current, a counter-current manner, or as a fractional extraction in which multiple solvents and/or solvent feed points are used to help facilitate the separation. The extraction process also can be conducted in a plurality of separation zones that can be in series or in parallel.

The extraction typically can be carried out at a temperature of about 10 to about 120° C. For example, the extraction can be conducted at a temperature of about 30 to about 80° C. The desired temperature range may be constrained further by the boiling point of the extractant components or water. Generally, it is undesirable to operate the extraction under conditions where the extractant boils. In one aspect, the extractor can be operated to establish a temperature gradient across the extractor in order to improve the mass transfer kinetics or decantation rates. In another aspect, the extractor may be operated under sufficient pressure to prevent boiling.

In an aspect of the invention, the mixed diol stream is extracted in a continuous counter-current extractor. The extractant is fed to the extractor at a location lower than the feed location of the mixed diol stream. The extractant moves up the counter-current extractor to form an extract phase exiting the top of the extractor and comprising a major amount of the three-carbon diols and/or the four-carbon diols and a minor amount of the ethylene glycol contained in the mixed diol stream. The mixed diol stream moves down the counter-current extractor to form the raffinate phase exiting the bottom of the extractor and comprising a major amount of the ethylene glycol and a minor amount of the three-carbon diols and/or the four-carbon diols contained in the mixed diol stream. In an aspect of the invention the feed ratio of the extractant to the mixed diol stream ranges from 0.5:1 to 20:1, or 1:1 to 10:1, or 1:1 to 5:1.

The mixed diol stream and extractant can be contacted by fractional extraction methods such as, for example, by fractional counter-current extraction. As used herein, the term "fractional counter-current extraction" is intended to include, but is not limited to, a method for separating a feed stream, e.g., reaction product fluid, containing two or more substances by charging the feed stream to a counter-current extraction process between the points where two immiscible solvents are charged to the extraction process. The two immiscible solvents should be immiscible over the entire temperature range of the extraction process. This method is sometimes referred to as "double solvent extraction." Fractional counter-current extraction can involve the use of a cascade of stages, extracting solvents and solution to be extracted entering at opposite ends of the cascade with the feed phase and hydrophobic extractant phase flowing counter-currently. Some example fractional counter-current extraction configurations may be found in Treybal, *Liquid Extraction,* 2nd Edition, McGraw-Hill Book Company, New York. 1963, pp. 275-276.

In an aspect of the invention, the mixed diol stream is extracted in a continuous fractional counter-current extractor. The extractant is fed to the extractor at a location lower than the feed location of the mixed diol stream. A hydrophilic solvent is fed to the extractor at a location higher than the mixed diol stream. In an aspect of the invention the feed ratio of the extractant to the mixed diol stream ranges from 0.5:1 to 20:1, or 1:1 to 10:1, or 1:1 to 5:1 and the feed ratio of the hydrophilic solvent to the mixed diol stream ranges from 0.05:1 to 2:1, or 0.1:1 to 1.5:1, or 0.1:1 to 0.8:1. The hydrophilic solvent may comprise water.

The extraction of the mixed diol stream produces a raffinate phase comprising a major amount of the lowest-carbon-number diols and a minor amount of the highest-carbon-number diols contained in the mixed diol stream and an extract phase comprising a major amount of the highest-carbon-number diols and a minor amount of the lowest-carbon-number diols contained in the mixed diol stream. The raffinate phase and the extract phase may be separated by any phase separation technology known in the art. The phase separation techniques can be accomplished in the extractor or in a separate liquid-liquid separation device. Suitable liquid-liquid separation devices include, but are not limited to, coalescers, cyclones and centrifuges. Typical equipment that can be used for liquid-liquid phase separation devices are described in the *Handbook of Separation process Technology*, ISBN 0-471-89558-X, John Wiley & Sons, Inc., 1987.

Removal of the extracted diols and recycle of the hydrophobic extractant is another aspect of the instant invention. A majority of the three-carbon diols and four-carbon diols can be removed from the extract phase to form a lean hydrophobic solvent. The lean hydrophobic solvent can be recycled whereby the extractant of step (B) comprises at least a portion of the lean hydrophobic solvent. The removal and recycle process may entail extraction, distillation or a combination of these unit operations. When extraction is chosen to produce the lean solvent, the step of extracting the mixed diol stream is called a forward extraction and the step of extracting the hydrophobic solvent extract exiting the forward extraction is called a back extraction. When distillation is chosen as the diol recovery method, the hydrophobic extractant is preferentially selected such that at least one component of the extractant forms a minimum boiling azeotrope with the diol components contained in the extract phase. Most preferably, the minimum-boiling azeotrope formed with the diol components is heterogeneous in nature, i.e., forms two liquid phases upon condensation.

In one aspect of the invention, diols contained in the extract phase are recovered by distillation wherein the diol-laden extract phase is fed to a distillation column, and the diols are removed overhead as the minimum-boiling azeotropes between at least one hydrophobic extractant component and the diol components to form a distillate product; and the bottoms product comprises a majority of the hydrophobic extractant components.

Examples of hydrophobic extractant components that form azeotropes with two-, three-, and four-carbon diols are hydrocarbons containing seven to fourteen carbon atoms such as toluene, p-xylene, o-xylene, m-xylene, ethylbenzene, 1,3,5-trimethylbenzene, 1,2,4-trimethylbenzene, isopropylbenzene, heptane, n-octane, 2,2-4-trimethyl-pentane, n-nonane, n-decane, n-undecane, and mixtures thereof.

Additional exemplary hydrophobic extractant components that form heterogeneous minimum-boiling azeotropes with ethylene glycol, butanediols, and propanediols are normal- and iso-paraffinic hydrocarbons containing six to fourteen carbon atoms and mixtures thereof, most preferably normal- and iso-paraffinic hydrocarbons containing nine to eleven carbon atoms and mixtures thereof. For example, preferable paraffinic hydrocarbons are n-octane, 2,2-4-trimethyl-pentane, n-nonane, n-decane, n-undecane, and mixtures thereof. The azeotrope-forming component also may comprise isoparaffinic mixed hydrocarbons having boiling ranges between about 100 and about 225° C., as exemplified by the ISOPAR™ solvents, such as Isopar E (boiling point range of 118 to 137° C.), ISOPAR G (boiling point range of 160 to 176° C.), ISOPAR H (boiling point range of 178 to 188° C.), ISOPAR K (boiling point range of 178 to 197° C.), ISOPAR L (boiling point range of 189 to 207° C.).

Optionally, one or more hydrocarbons may be added to the distillation feed stream or provided as reflux to the distillation column to enhance the azeotropic separation of the diols. It is advantageous that the minimum boiling azeotropes formed between the diols and the hydrophobic extractant component have a high diol content. Examples of high diol content azeotropes include those with greater than 5 weight percent diol or greater than 15 weight percent diol. Examples of hydrophobic solvent and diol azeotropes are given in the table below where pure component boiling points (NBP), azeotrope boiling points (Azeo BP), and weight percent of alkane in the azeotrope are given for ethylene glycol (EG), butanediol (DBO) and propanediol (PDO) with nonane, decane, undecane, and 2-ethylhexanol (2-EH) as the solvent:

|  | NBP, C | EG | BDO | PDO |
|---|---|---|---|---|
| NBP, C |  | 197.1 | 196.5 | 187.7 |
| Azeo BP, C |  |  |  |  |
| nonane | 150.8 | 144.3 | 145.3 | 143.2 |
| Decane | 174.3 | 160.8 | 162.2 | 158.7 |
| undecane | 195.9 | 172.7 | 174.2 | 169.3 |
| 2-EH | 184.6 | 177.1 | 183.2 | 178.4 |
| wt % alkane in azeo |  |  |  |  |
| nonane |  | 91.7% | 89.3% | 91.2% |
| Decane |  | 84.2% | 80.0% | 77.6% |
| undecane |  | 75.1% | 68.6% | 60.8% |
| 2-EH |  | 75.0% | 82.5% | 67.8% |

If the diol and the azeotroping agent do not form two liquid phases, i.e., do not form a heterogeneous azeotrope, then water may optionally be added to the distillate product to assist in the generation of two liquid phases. Water may be added in an amount equal to 10 to 100 percent by weight of the distillate product. When water is added, the diols will partition preferentially into a water-rich phase. The organic phase, largely free of diols may be returned to the distillation column as reflux. The water-rich phase may be further treated to remove hydrophobic solvent components by steam distillation wherein live steam is added to the column, or by distillation of water-hydrophobic solvent azeotropes as an overhead product.

As noted above, when extraction is chosen to produce the lean solvent, the step of extracting the mixed diol stream is called a forward extraction and the step of extracting the hydrophobic solvent extract phase which exits the forward extraction is called a back extraction. Thus, in another aspect of the invention, diol components can be removed from the extract phase into water and a lean solvent recovered via a back extraction process. Our process also comprises extracting the extract phase from step (B) with a second extractant comprising water to form a second extract phase comprising a major amount of the diol components contained in the extract phase from step (B) and a second raffinate phase (i.e., lean solvent) comprising a minor amount of the diol composition contained in the extract phase from step (B). Typically, the concentration of diol in the second extract phase can be about 1 to about 50 percent by weight or, in another example, about 5 to about 20 percent by weight.

The second extract phase can be passed to a process for recovery of hydrophobic solvent components, for example by distillation or steam stripping. The second raffinate phase can be recycled to the first extraction by combining the second raffinate phase with the first extractant. The second raffinate phase can be distilled prior to recycle to produce a hydrophobic solvent distillate that is subsequently combined with the extractant of step (A).

The weight ratio of the second extractant to the first extract phase from step (B) of our inventive process is about 0.05:1 to about 5:1. Further examples of weight ratios of the second extractant to the first extract phase are about 0.1:1 to 3:1 and about 0.1:1 to about 2:1.

The back extraction process can be conducted at a temperature of about 10 to about 120° C. For example, in one aspect of the invention, the back extraction step of the invention is carried out at a temperature of about 30 to about 80° C.

The back extraction process can be carried out by any extraction means known in the art to intimately contact two immiscible liquid phases and to separate the resulting phases after the extraction procedure. For example, the back extraction can be carried out using columns, centrifuges, mixer-settlers, and miscellaneous devices. The various types of extractors may be used alone or in any combination.

The back extraction may be conducted in one or more stages. The back extraction also can be conducted in a batch or continuous fashion. In a continuous mode, the back extraction may be carried out in a co-current, a counter-current manner, or as a fractional extraction in which multiple solvents and/or solvent feed points are used to help facilitate the separation. Further, the back extraction process of this invention can be conducted in a plurality of separation zones in series or in parallel.

Optionally, an additional hydrophobic solvent may be employed to modify the physical and transport properties of the hydrophobic extract phase prior to introduction into the back extraction process. This additional hydrophobic solvent can be the same as the optional, second hydrophobic solvent employed in the forward extraction zone. The optional addition of the second hydrophobic extraction solvent can be used to remove any unwanted relatively hydrophobic components from the hydrophilic extract phase of the back extractor zone. In one embodiment, the second hydrophobic extraction solvent is not required, and the back extractor is operated as a traditional extractor instead of as a fractional extractor.

Alternatively, the back extraction process may be operated in a fractional extraction mode with the additional second hydrophobic solvent added at a feed point closer to the end of the extractor where the back extraction raffinate stream exits than the feed point of the hydrophobic extract phase from the forward extraction zone. The mass feed ratio of the additional second hydrophobic solvent to the hydrophobic extract phase from the forward extraction zone can be between 0:1 and 1.5:1 or between 0.05:1 and 0.45:1.

The forward extraction of the mixed diol stream also produces a raffinate phase which, in addition to ethylene glycol, can comprise three-carbon diols, four-carbon diols, water, and hydrophobic solvent. The raffinate phase can be further processed to recover a high-purity ethylene glycol product. For example, the raffinate phase can be fed to a distillation column where water and hydrophobic solvent can be separated from the diols. The hydrophobic solvent can be further processed and/or recycled to the extractor.

A further embodiment of our invention is a process for recovering purified ethylene glycol from a mixed diol stream, comprising
(A) extracting the mixed diol stream, comprising
  (i) 20 weight percent to 99.5 weight percent, ethylene glycol;
  (ii) 20 ppm by weight to 40 weight percent of one or more three-carbon diols selected from 1,2-propanediol and 1,3-propanediol, and 20 ppm by weight to 30 weight percent of one or more four-carbon diols selected from 1,2-butanediol, 1,3-butanediol, 1,4-butanediol, and 2,3-butanediol; each based on the total weight of diols, and
  (iii) 5 weight percent to 35 weight percent water, based on the total weight of diols and water, with an extractant, comprising
    (i) a hydrophobic solvent selected from 2-ethylhexanol, cyclohexanol, n-hexanol, methyl isobutyl ketone, methyl isopropyl ketone, methyl propyl ketone, diisobutyl ketone, trioctylphosphine oxide, trihexylphosphine oxide, and mixtures thereof; and
    (ii) optionally, a second modifying hydrophobic solvent selected from hexane, heptane, octane, decane, benzene, toluene, xylenes, isoparaffinic mixed hydrocarbons having a boiling range between 90 and 325° C., methyl napthtalenes, and mixtures thereof; to form a raffinate phase comprising a major amount of the ethylene glycol and a minor amount of the three-carbon diols and/or four-carbon diols contained in the mixed diol stream and an extract phase comprising a major amount of the three-carbon diols and/or four-carbon diols and a minor amount of the ethylene glycol contained in the mixed diol stream; and
(B) separating the raffinate phase and the extract phase.

The various aspects of mixed diol stream composition, water content, hydrophobic solvent, second modifying hydrophobic solvent, weight percent of hydrophobic solvent and second modifying hydrophobic solvent in the extractant, recovery of ethylene glycol, three-carbon and/or four-carbon diols in the mixed diol stream to the raffinate phase, extraction process, extract phase clean-up and lean solvent recycle, and recovery of high-purity ethylene glycol from the raffinate phase discussed above apply to the present embodiment. For example, the mixed diol stream can comprise 20 weight percent to 99.5 weight percent ethylene glycol, 20 weight percent to 90 weight percent ethylene glycol, 20 weight percent to 80 weight percent ethylene glycol, 20 weight percent to 70 weight percent ethylene glycol, or 20 weight percent to 60 weight percent ethylene glycol; 20 ppm to 40 weight percent three-carbon diols, 20 ppm to 30 weight percent three-carbon diols, 0.1 weight percent to 40 weight percent three-carbon diols, 0.1 weight percent to 30 weight percent three-carbon diols, or 0.1 weight percent to 20 weight percent three-carbon diols; and 20 ppm to 40 weight percent four-carbon diols, 20 ppm to 30 weight percent four-carbon diols, 20 ppm to 20 weight percent four-carbon diols, 0.1 weight percent to 40 weight percent four-carbon diols, 0.1 weight percent to 30 weight percent four-carbon diols, or 0.1 weight percent to 20 weight percent four-carbon diols, each based on the total weight of diols. The amount of water in the mixed diol stream, based on the total weight of diols and water, can range from 5 weight percent to 35 weight percent water, 5 weight percent to 25 weight percent water, 5 weight percent to 15 weight percent water, 10 weight percent to 35 weight percent water, or 10 weight percent to 25 weight percent water.

The extractant can comprises at least one hydrophobic solvent selected from 2-ethylhexanol, cyclohexanol, n-hexanol, methyl isobutyl ketone, methyl isopropyl ketone, methyl propyl ketone, and diisobutyl ketone, trioctylphosphine oxide, trihexylphosphine oxide, and mixtures thereof. In another aspect, the hydrophobic solvent can be selected from 2-ethylhexanol, cyclohexanol, trioctylphosphine oxide, trihexylphosphine oxide, and mixtures thereof. The optional, second modifying hydrophobic solvent can be selected from hydrocarbons having from 5 to 20 atoms. The second, modifying hydrophobic solvent can be selected from hexane, heptane, octane, decane, benzene, toluene, xylenes, methyl napththalenes, isoparaffinic mixed hydrocarbons having boiling ranges between about 90 and about 325° C., and mixtures thereof.

A third embodiment of our invention, is a process for recovering purified ethylene glycol from a mixed diol stream comprising ethylene glycol and four-carbon diols, comprising
(A) extracting the mixed diol stream, comprising
  (i) 50 weight percent to 99.99 weight percent, ethylene glycol;
  (ii) 0.01 weight percent to 50 weight percent of one or more four-carbon diols selected from 1,2-butanediol, 1,3-butanediol, 1,4 butanediol, and 2,3-butanediol; each based on the total weight of diols, and
  (iii) 0 weight percent to 50 weight percent water, based on the total weight of diols and water, with an extractant, comprising
    (i) a hydrophobic solvent selected from alkanols having from 6 to 20 carbon atoms, ketones having from 5 to 20 carbon atoms, esters having from 5 to 20 carbon atoms, ethers having from 5 to 20 carbon atoms, carboxylic acids having from 5 to 20 carbon atoms, trialkylphosphine oxides having from 18 to 48 carbon atoms, and mixtures thereof; and
    (ii) optionally, a second modifying hydrophobic solvent selected from hydrocarbons having from 5 to 20 carbon atoms; to form a raffinate phase comprising a major amount of the ethylene glycol and a minor amount of the four-carbon diols contained in the mixed diol stream and an extract phase comprising a major amount of the four-carbon diols and a minor amount of the ethylene glycol contained in the mixed diol stream; and
(B) separating the raffinate phase and the extract phase.

The various aspects of mixed diol stream composition, water content, hydrophobic solvent, second modifying hydrophobic solvent, weight percent of hydrophobic solvent and second modifying hydrophobic solvent in the extractant, recovery of ethylene glycol and/or four-carbon diols in the mixed diol stream to the raffinate phase, extraction process, extract phase clean-up and lean solvent recycle, and recovery of high-purity ethylene glycol from the raffinate phase discussed above apply to the present embodiment. For example, the mixed diol stream can comprise 50 weight percent to 99.99 weight percent ethylene glycol, 50 weight percent to 99 weight percent ethylene glycol, 50 weight percent to 95 weight percent ethylene glycol, 50 weight percent to 90 weight percent ethylene glycol, 50 weight percent to 80 weight percent ethylene glycol, 60 weight percent to 99.99 weight percent ethylene glycol, 60 weight percent to 99 weight percent ethylene glycol, 60 weight percent to 95 weight percent ethylene glycol, 60 weight percent to 90 weight percent ethylene glycol, 60 weight percent to 80 weight percent ethylene glycol, 70 weight percent to 99.99 weight percent ethylene glycol, 70 weight percent to 99 weight percent ethylene glycol, 70 weight percent to 95 weight percent ethylene glycol, 70 weight percent to 90 weight percent ethylene glycol, or 70 weight percent to 80 weight percent ethylene glycol; and 0.01 weight percent to 50 weight percent four-carbon diols, 0.01 weight percent to 40 weight percent four-carbon diols, 0.01 weight percent to 30 weight percent four-carbon diols, 0.01 weight percent to 20 weight percent four-carbon diols, 0.01 weight percent to 5 weight percent four-carbon diols, 0.01 weight percent to 2 weight percent four-carbon diols, 1 weight percent to 50 weight percent four-carbon diols, 1 weight percent to 40 weight percent four-carbon diols, 1 weight percent to 30 weight percent four-carbon diols, 1 weight percent to 20 weight percent four-carbon diols, 1 weight percent to 5 weight percent four-carbon diols, 1 weight percent to 2 weight percent four-carbon diols, 5 weight percent to 50 weight percent four-carbon diols, 5 weight percent to 40 weight percent four-carbon diols, 5 weight percent to 30 weight percent four-carbon diols, or 5 weight percent to 20 weight percent four-carbon diols.

Our process can also be used, for example, to separate glycols from the hydrogenolysis of glycerol. A fourth embodiment of our invention, is a process for recovering diols from a mixed diol stream, comprising (A) extracting the mixed diol stream, comprising
  (i) 0.1 weight percent to 50 weight percent of one or more diols selected from ethylene glycol, 1,2-propanediol, 1,3-propanediol 1,2-butanediol, 1,3-butanediol, 1,4-butanediol, and 2,3-butanediol;
  (ii) 5 weight percent to 90 weight percent glycerol; and
  (iii) 5 weight percent to 90 weight percent water; each based on the total weight of the mixed diol stream with an extractant, comprising
  (i) a hydrophobic solvent selected from alkanols having from 6 to 20 carbon atoms, ketones having from 5 to 20 carbon atoms, esters having from 5 to 20 carbon atoms, ethers having from 5 to 20 carbon atoms, carboxylic acids having from 5 to 20 carbon atoms, trialkylphosphine oxides having from 18 to 48 carbon atoms, and mixtures thereof; and
  (ii) optionally, a second modifying hydrophobic solvent selected from hydrocarbons having from 5 to 20 carbon atoms; to form a raffinate phase comprising a major amount of the glycerol and a minor amount of the diols contained in the mixed diol stream and an extract phase comprising a major amount of the diols and a minor amount of the glycerol contained in the mixed diol stream; and
(B) separating the raffinate phase and the extract phase.

The various aspects of hydrophobic solvent, second modifying hydrophobic solvent, weight percent of hydrophobic solvent and second modifying hydrophobic solvent in the extractant apply to the present embodiment.

For example, the mixed diol stream can comprise 0.1 weight percent to 50 weight percent ethylene glycol, 5 weight percent to 50 weight percent ethylene glycol, 10 weight percent to 40 weight percent ethylene glycol, 10 weight percent to 30 weight percent ethylene glycol, or 20 weight percent to 40 weight percent ethylene glycol; 0.1 weight percent to 40 weight percent three-carbon diols, 0.1 weight percent to 30 weight percent three-carbon diols, 1 weight percent to 40 weight percent three-carbon diols, 1 weight percent to 30 weight percent three-carbon diols, or 1 weight percent to 20 weight percent three-carbon diols; and 0.1 weight percent to 40 weight percent four-carbon diols, 0.1 weight percent to 30 weight percent four-carbon diols, 0.1 weight percent to 20 weight percent four-carbon diols, 1 weight percent to 40 weight percent four-carbon diols, 1 weight percent to 30 weight percent four-carbon diols, or 1 weight percent to 20 weight percent four-carbon diols, each based on the total weight of the mixed diol stream.

The amount of glycerol in the mixed diol stream, based on the total weight of the mixed diol stream, can range from 5 weight percent to 90 weight percent, 5 weight percent to 70 weight percent, 5 weight percent to 50 weight percent, 5 weight percent to 25 weight percent, 5 weight percent to 10 weight percent, 10 weight percent to 90 weight percent, 10 weight percent to 70 weight percent, 10 weight percent to 50 weight percent, 10 weight percent to 25 weight percent, 25 weight percent to 90 weight percent, 25 weight percent to 70 weight percent, or 25 weight percent to 50 weight percent.

The amount of water in the mixed diol stream, based on the total weight of the mixed diol stream, can range from 5 weight percent to 90 weight percent, 5 weight percent to 70 weight percent, 5 weight percent to 50 weight percent, 5 weight percent to 25 weight percent, 5 weight percent to 10 weight percent, 10 weight percent to 90 weight percent, 10 weight percent to 70 weight percent, 10 weight percent to 50 weight percent, 10 weight percent to 25 weight percent, or 25 weight percent to 90 weight percent, 25 weight percent to 70 weight percent, 25 weight percent to 50 weight percent.

The process of the present invention forms a raffinate phase comprising a major amount of the glycerol and a minor amount of the diols contained in the mixed diol stream. In an aspect of the present invention, greater than 90 weight percent of the glycerol is recovered in the raffinate phase. In another aspect, greater than 95 weight percent, greater than 98 weight percent, greater than 99 weight percent, or greater than 99.9 weight percent of the glycerol is recovered in the raffinate phase.

The process of the present invention forms an extract phase comprising a major amount of the diols and a minor amount of the glycerol contained in the mixed diol stream. In an aspect of the invention, greater than 60 percent of the diols in the mixed diol stream is recovered in the extract phase. In another aspect, greater than 70 weight percent, greater than 80 weight percent, greater than 90 weight percent, greater than 98 weight percent, or greater than 99 weight percent of the diols in the mixed diol stream is recovered in the extract phase.

The extract phase can be back extracted with water to form a second, aqueous extract phase containing a major amount of diols in the second, aqueous extract phase and a minor amount of diols in the second, hydrophobic solvent raffinate phase. The hydrophobic solvent may be recycled to the first extractor to separate glycerol and the diols. The aqueous, extract phase can become a new mixed diol feed to produce purified ethylene glycol and/or three carbon glycols by the processes described above and below, respectively.

Our process can also be used, for example, to separate glycols from a fermentation broth. A fifth embodiment of our invention, is a process for recovering diols from a mixed diol stream, comprising
(A) extracting the mixed diol stream, comprising
  (i) 0.1 weight percent to 30 weight percent of ethylene glycol, 1,2-propanediol and 1,3-propanediol, 1,2-butanediol, 1,3-butanediol, 1,4-butanediol, and 2,3-butanediol;
  (ii) 5 to 50 weight percent glucose; and
  (iii) 50 weight percent to 90 weight percent water; each based on the total weight of the mixed diol stream, with an extractant, comprising
  (i) a hydrophobic solvent selected from alkanols having from 6 to 20 carbon atoms, ketones having from 5 to 20 carbon atoms, esters having from 5 to 20 carbon atoms, ethers having from 5 to 20 carbon atoms, carboxylic acids having from 5 to 20 carbon atoms, trialkylphosphine oxides having from 18 to 48 carbon atoms, and mixtures thereof; and
  (ii) optionally, a second modifying hydrophobic solvent selected from hydrocarbons having from 5 to 20 carbon atoms; to form a raffinate phase comprising a major amount of the glucose and a minor amount of the diols contained in the mixed diol stream and an extract phase comprising a major amount of the diols and a minor amount of the glucose contained in the mixed diol stream; and
(B) separating the raffinate phase and the extract phase.

The various aspects of hydrophobic solvent, second modifying hydrophobic solvent, weight percent of hydrophobic solvent and second modifying hydrophobic solvent in the extractant apply to the present embodiment.

For example, the mixed diol stream can comprise 0.1 weight percent to 30 weight percent ethylene glycol, 1 weight percent to 30 weight percent ethylene glycol, 1 weight percent to 20 weight percent ethylene glycol, 5 weight percent to 30 weight percent ethylene glycol, or 5 weight percent to 20 weight percent ethylene glycol; 0.1 weight percent to 30 weight percent three-carbon diols, 1 weight percent to 30 weight percent three-carbon diols, 1 weight percent to 20 weight percent three-carbon diols, 5 weight percent to 30 weight percent three-carbon diols, or 5 weight percent to 20 weight percent three-carbon diols; and 0.1 weight percent to 30 weight percent four-carbon diols, 1 weight percent to 30 weight percent four-carbon diols, 1 weight percent to 20 weight percent four-carbon diols, 5 weight percent to 30 weight percent four-carbon diols, 5 weight percent to 20 weight percent four-carbon diols, or 10 weight percent to 20 weight percent four-carbon diols, each based on the total weight of the mixed diol stream.

The amount of glucose in the mixed diol stream, based on the total weight of the mixed diol stream, can range from 5 weight percent to 50 weight percent, 5 weight percent to 40 weight percent, 5 weight percent to 30 weight percent, 5 weight percent to 20 weight percent, 5 weight percent to 10 weight percent, 10 weight percent to 50 weight percent, 10 weight percent to 40 weight percent, 10 weight percent to 30 weight percent, 10 weight percent to 20 weight percent, 25 weight percent to 50 weight percent, 25 weight percent to 40 weight percent, or 25 weight percent to 30 weight percent.

The amount of water in the mixed diol stream, based on the total weight of the mixed diol stream, can range from 50 weight percent to 90 weight percent, 50 weight percent to 80 weight percent, 50 weight percent to 70 weight percent, 50 weight percent to 60 weight percent, 60 weight percent to 90 weight percent, 60 weight percent to 80 weight percent, 60 weight percent to 70 weight percent, 70 weight percent to 90 weight percent, 70 weight percent to 80 weight percent, or 80 weight percent to 90 weight percent.

The process of the present invention forms a raffinate phase comprising a major amount of the glucose and a minor amount of the diols contained in the mixed diol stream. In an aspect of the present invention, greater than 90 weight percent of the glucose is recovered in the raffinate phase. In another aspect, greater than 95 weight percent, greater than 98 weight percent, greater than 99 weight percent, or greater than 99.5 weight percent of the glucose is recovered in the raffinate phase.

The process of the present invention forms an extract phase comprising a major amount of the diols and a minor amount of the glucose contained in the mixed diol stream. In an aspect of the invention, greater than 60 percent of the diols in the mixed diol stream is recovered in the extract phase. In another aspect, greater than 70 weight percent, greater than 80 weight percent, greater than 90 weight percent, greater than 98 weight percent, or greater than 99 weight percent of the diols in the mixed diol stream is recovered in the extract phase.

The extract phase can be back extracted with water to form a second, aqueous extract phase containing a major amount of diols in the second, aqueous extract phase and a minor amount of diols in the second, hydrophobic solvent raffinate phase. The hydrophobic solvent may be recycled to the first extractor to separate glucose and the diols. The aqueous, extract phase can become a new mixed diol feed to produce purified ethylene glycol and/or three carbon glycols by the processes described above and below, respectively.

A sixth embodiment of our invention, is a process for recovering purified propanediol, from a mixed diol stream comprising propanediols and butanediols, comprising
(A) extracting the mixed diol stream, comprising
  (i) 1 weight percent to 99.5 weight percent of one or more three-carbon diols selected from 1,2-propanediol and 1,3-propanediol;
  (ii) 20 ppm by weight to 99 weight percent of one or more four-carbon diols selected from 1,2-butanediol, 1,3-butanediol, 1,4-butanediol, and 2,3-butanediol; each based on the total weight of diols, and
  (iii) 0 weight percent to 50 weight percent water, based on the total weight of diols and water, with an extractant, comprising
  (i) a hydrophobic solvent selected from alkanols having from 6 to 20 carbon atoms, ketones having from 5 to 20 carbon atoms, esters having from 5 to 20 carbon atoms, ethers having from 5 to 20 carbon atoms, carboxylic acids having from 5 to 20 carbon atoms, trialkylphosphine oxides having from 18 to 48 carbon atoms, and mixtures thereof; and
  (ii) optionally, a second modifying hydrophobic solvent selected from hydrocarbons having from 5 to 20 carbon atoms; to form a raffinate phase comprising a major amount of the three-carbon diols and a minor amount of the four-carbon diols contained in the mixed diol stream and an extract phase comprising a major amount of the four-carbon diols and a minor amount of the three-carbon diols contained in the mixed diol stream; and
(B) separating the raffinate phase and the extract phase.

The various aspects of water content in the mixed diol stream, hydrophobic solvent, second modifying hydrophobic solvent, weight percent of hydrophobic solvent and second modifying hydrophobic solvent in the extractant, extraction process, and extract phase clean-up and lean solvent recycle discussed above apply to the present embodiment. The mixed diol stream may comprise 1 weight percent to 99.5 weight percent three-carbon diols, 1 weight percent to 95 weight percent three-carbon diols, 1 weight percent to 90 weight percent three-carbon diols, 1 weight percent to 80 weight percent three-carbon diols, 1 weight percent to 70 weight percent three-carbon diols, 10 weight percent to 99.5 weight percent three-carbon diols, 10 weight percent to 95 weight percent three-carbon diols, 10 weight percent to 90 weight percent three-carbon diols, 10 weight percent to 80 weight percent three-carbon diols, 10 weight percent to 70 weight percent three-carbon diols, 30 weight percent to 99.5 weight percent three-carbon diols, 30 weight percent to 95 weight percent three-carbon diols, 30 weight percent to 90 weight percent three-carbon diols, 30 weight percent to 80 weight percent three-carbon diols, or 30 weight percent to 70 weight percent three-carbon diols; and 20 ppm to 99.5 weight percent four-carbon diols, 20 ppm to 95 weight percent four-carbon diols, 20 ppm to 90 weight percent four-carbon diols, 20 ppm to 80 weight percent four-carbon diols, 20 ppm to 70 weight percent four-carbon diols, 1 weight percent to 99.5 weight percent four-carbon diols, 1 weight percent to 95 weight percent four-carbon diols, 1 weight percent to 90 weight percent four-carbon diols, 1 weight percent to 80 weight percent four-carbon diols, 1 weight percent to 70 weight percent four-carbon diols, 10 weight percent to 99.5 weight percent four-carbon diols, 10 weight percent to 95 weight percent four-carbon diols, 10 weight percent to 90 weight percent four-carbon diols, 10 weight percent to 80 weight percent four-carbon diols, 10 weight percent to 70 weight percent four-carbon diols, 30 weight percent to 99.5 weight percent four-carbon diols, 30 weight percent to 95 weight percent four-carbon diols, 30 weight percent to 90 weight percent four-carbon diols, 30 weight percent to 80 weight percent four-carbon diols, or 30 weight percent to 70 weight percent four-carbon diols, each based on the total weight of diols.

The process of the present invention forms a raffinate phase comprising a major amount of the three-carbon diols and a minor amount of the four-carbon diols contained in the mixed diol stream. In an aspect of the present invention, greater than 95 weight percent of the three-carbon diols in the mixed diol stream is recovered in the raffinate phase. In another aspect, greater than 98 weight percent, greater than 99 weight percent, greater than 99.5 weight percent, or greater than 99.99 weight percent of the three-carbon diols in the mixed diol stream is recovered in the raffinate phase.

The process of the present invention forms an extract phase comprising a major amount of the four-carbon diols and a minor amount of the three-carbon diols contained in the mixed diol stream. In an aspect of the invention, greater than 60 weight percent of the four-carbon diols in the mixed diol stream is recovered in the extract phase. In another aspect, greater than 70 weight percent, greater than 80 weight percent, greater than 90 weight percent, greater than 95 weight percent, greater than 98 weight percent, or greater than 99 weight percent of the four-carbon diols in the mixed diol stream is recovered in the extract phase.

The raffinate phase can be concentrated in three-carbon diols. The concentration of the three-carbon diols, based on the total weight of diols in the raffinate phase, can be greater than 95 weight percent, greater than 98 weight percent, greater than 99 weight percent, greater than 99.9 weight percent, or greater than 99.99 weight percent. The concentration of the four-carbon diols, based on the total weight of diols in the raffinate phase can be less than 5 weight percent, less than 1 weight percent, less than 0.5 weight percent, less than 1000 ppm on a weight basis, less than 500 ppm on a weight basis, or less than 100 ppm on a weight basis.

The forward extraction of the mixed diol stream also produces a raffinate phase which, in addition to three-carbon diols, can comprise four-carbon diols, water, and hydrophobic solvent. The raffinate phase can be further processed to recover a high-purity three-carbon diol product. For example, the raffinate phase can be fed to a distillation column where water and hydrophobic solvent can be separated from the three-carbon diols. The hydrophobic solvent can be further processed and/or recycled to the extractor.

Figure 2:
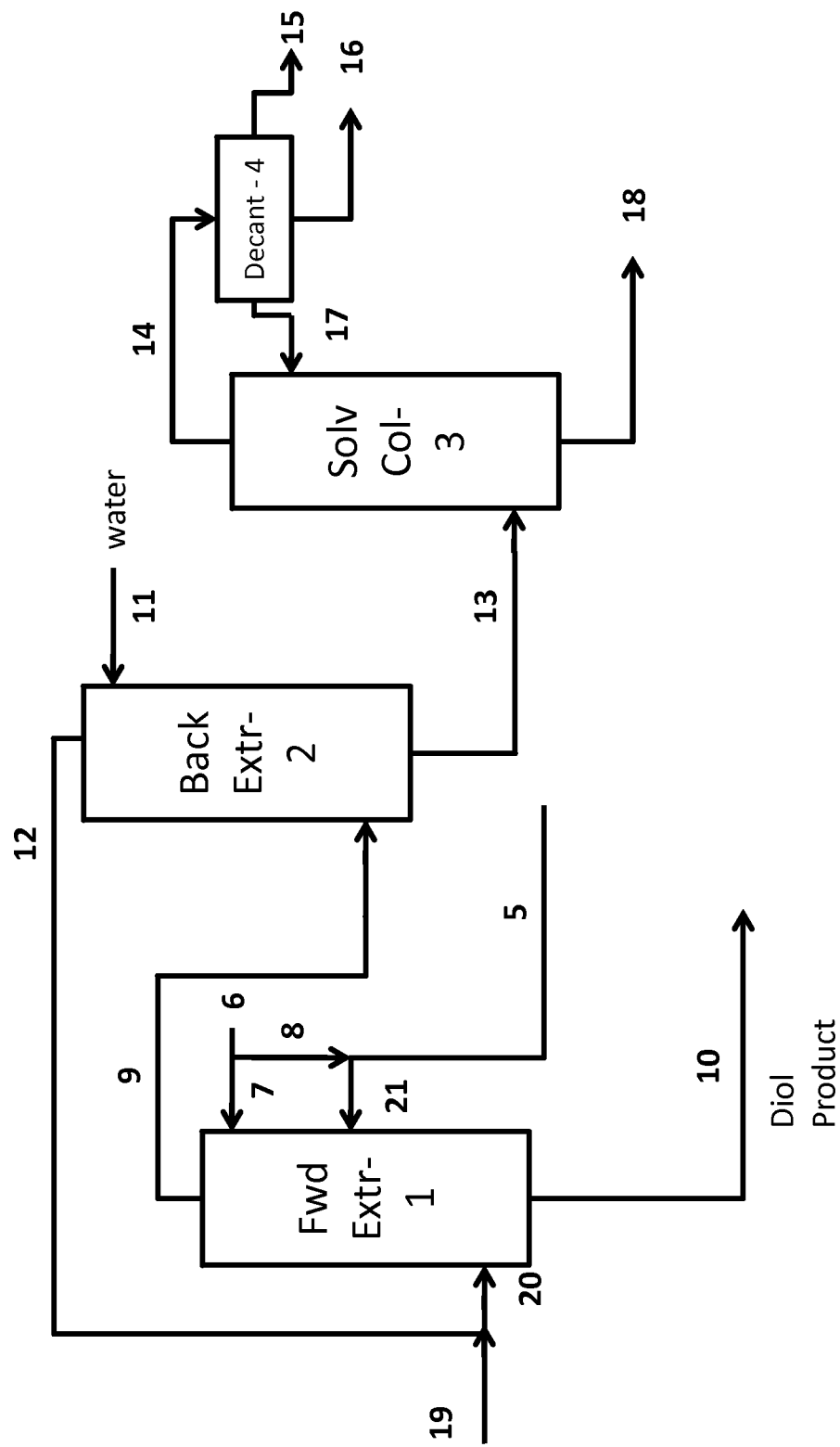
FIG. 2 is a schematic flow diagram of another embodiment of the invention in which the forward extraction zone is operated as a fractional counter-current extraction, the hydrocarbon solvent in the extract is recovered via back extraction and recycled to the forward extraction zone, and the three-carbon diols and four-carbon diols are recovered in a distillation zone.

FIGS. 1 and 2 present two, non-limiting embodiments of the instant invention, described herein in detail. In a first embodiment of the invention as laid out in FIG. 1, Mixed Diol Feed Stream 6 is fed counter-currently to Forward Extractor 1, wherein the stream is immediately contacted with Extractant Stream 21. Two products exit Forward Extractor 1, the Hydrophilic Raffinate Product Stream 8, depleted of higher-number-carbon diols, and Hydrophobic Extract Product Stream 7. An additional hydrophobic solvent Stream 14, preferably one that forms an azeotrope with the higher-carbon-number diols, can be mixed with Stream 7 before Stream 7 is fed to a distillation column, Solvent Column 2. A Lean Hydrophobic Solvent Stream 19, reduced in the amount of diols, exits as the bottoms product of Solvent Column 2. Lean Hydrophobic Solvent Stream 19 is recycled back to Forward Extractor 1: Stream 19 is combined with Solvent Make-up Stream 20 to produce Extractant Stream 21 which is fed to Forward Extractor 1. An azeotropic composition comprising diols, hydrophobic solvent, and/or water exits the top of Solvent Column 2 as Stream 15. Stream 15 is condensed and phases are allowed to separate in Decanter 3. Part of the hydrophobic phase is refluxed back to Solvent Column 2 as Stream 18 and part can be purged or sent for further processing as Stream 16. The hydrophilic phase, containing the majority of the diols, can be sent for further processing as Stream 17.

Raffinate Hydrophilic Product Stream 8 from Forward Extractor 1 is rich in ethylene glycol. Stream 8 can be sent to a distillation column, Refining Column 4, to produce a purified ethylene glycol bottoms Stream 13. Stream 9, exiting the top of Refining Column 4 can comprise water, hydrophobic solvent, higher-carbon-number diols, and/or ethylene glycol. Stream 9 is condensed and allowed to phase separate in Decanter 5. Part of the hydrophobic phase is refluxed back to Refining Column 4 as Stream 12 and part can be purged or sent for further processing as Stream 10. The hydrophilic phase can be sent for further processing as Stream 11.

In the previously described first embodiment of the instant invention, conventional extraction, i.e., extraction involving a single solvent feed point is utilized for the forward extraction zone. It may be advantageous, however, to operate the forward extraction zone as a fractional counter-current extraction in which additional hydrophobic solvent components or hydrophilic solvent components are introduced as separate feeds. In a second embodiment of the invention as set forth in FIG. 2, Hydrophilic Solvent Stream 6 is optionally split into Stream 7 and Stream 8 wherein Stream 8 is combined with Mixed Diol Feed Stream 5 to produce Stream 21. Stream 21 is fed counter-currently to Forward Extractor 1, wherein the stream is intimately contacted with Hydrophobic Solvent Stream 20. When operated as a fractional extractor, Stream 7 is introduced into Forward Extractor 1 above feed Stream 21. Two products exit Forward Extractor 1, the Hydrophilic Raffinate Diol Product Stream 10 rich in ethylene glycol and the Hydrophobic Solvent Extract Stream 9 rich in higher-carbon-number diols. The purpose of feed Stream 7 is to further reduce losses of lower-carbon-number diols (e.g., ethylene glycol) into Stream 9. Stream 9 is fed counter-currently to a second extraction zone, Back Extractor 2, wherein the stream is intimately contacted with Water Stream 11. Two products are withdrawn from Back Extractor 2, the Hydrophobic Raffinate Stream 12 comprising the lean hydrophobic solvent which is recycled to Forward Extractor 1, and the Hydrophilic Extract Stream 13 comprising higher-carbon-number diols. Stream 13 is refined via distillation in Solvent Column 3. Bottoms product, Stream 18, comprises water and diols. Stream 14 exiting the top of Solvent Column 3 is condensed and the phases are allowed to separate in Decanter 4. Part of the hydrophobic phase is refluxed to Solvent Column 3 in Stream 17 and part of the hydrophobic phase is purged or sent for further processing in Stream 15. A hydrophilic phase is purged or sent for further processing in Stream 16.

The efficiency of the extraction process of the invention can be measured by a partition coefficient, abbreviated herein as "P(A)" of a diol component "A" which is defined as the concentration of diol component "A" in the hydrophobic phase divided by the concentration of diol component "A" in the hydrophilic phase. The partition coefficient may be determined by analysis of diol component "A" by known methods such as, for example, gas chromatography.

When the one or more higher-carbon-number diols ("H") are partitioned between the hydrophilic phase and the hydrophobic phase by the extraction processes of the invention, the P(H) value of diol component "H" can be maintained at a level greater than about 0.4, greater than about 0.5, or greater than about 0.7, depending on the efficiency of the extraction process. If the P(H) value is high, diol component "H" will preferentially distribute into the hydrophobic phase. Similarly, the efficiency of the extraction process can be measured by a partition coefficient of one or more lower-carbon-number diols ("L"). The partition coefficient P(L) value of diol component "L" can be less than about 0.5, less than about 0.4, or less than about 0.25, depending on the efficiency of the extraction process. For example, if a mixture of ethylene glycol, 1,2-propanediol, 1,2-butane diol, and water are vigorously mixed with a hydrophobic solvent and allowed to phase separate, the 1,2-butanediol can desirably have a partition coefficient P(1,2-BDO) greater than about 0.4, greater than about 0.5, or greater than 0.7 and ethylene glycol can desirably have a partition coefficient P(EG) less than 0.5, less than 0.4, or less than 0.25.

In an aspect, the extraction process of this invention can be conducted in a manner such that a separation criterion is satisfied. The criterion referred to herein as selectivity between diol components "H" and "L", is based on ratio of the partition coefficients defined above. For example, the selectivity ("S") between "H" and "L" is a partition coefficient ratio, $S=P(H)/P(L)$. The S value for this ratio can be maintained at a level greater than about 1.5. Other values of S include greater than about 2.2 and greater than about 3.0. If the S value is high, the extraction will effectively and efficiently separate the key higher-carbon-number diol components and lower-carbon-number diol components, "H" and "L", into the extract and raffinate phases respectively.

The invention also includes the following non-limiting embodiments that are set forth below.

A First Embodiment is a process for recovering purified ethylene glycol from a mixed diol stream, comprising
(A) extracting the mixed diol stream, comprising
   (i) 1 weight percent to 99.5 weight percent, ethylene glycol;
   (ii) 20 ppm by weight to 99 weight percent of one or more three-carbon diols and four-carbon diols selected from 1,2-propanediol, 1,3-propanediol, 1,2-butanediol, 1,3-butanediol, 1,4-butanediol, and 2,3-butanediol; each based on the total weight of diols, and
   (iii) 0 weight percent to 50 weight percent water, based on the total weight of diols and water, with an extractant, comprising
   (i) a hydrophobic solvent selected from alkanols having from 6 to 20 carbon atoms, ketones having from 5 to 20 carbon atoms, esters having from 5 to 20 carbon atoms, ethers having from 5 to 20 carbon atoms, carboxylic acids having from 5 to 20 carbon atoms, trialkylphosphine oxides having from 18 to 48 carbon atoms, and mixtures thereof; and
   (ii) optionally, a second modifying hydrophobic solvent selected from hydrocarbons having from 5 to 20 carbon atoms;
   to form a raffinate phase comprising a major amount of the ethylene glycol and a minor amount of the three-carbon diols and/or four-carbon diols contained in the mixed diol stream and an extract phase comprising a major amount of the three-carbon diols and/or four-carbon diols and a minor amount of the ethylene glycol contained in the mixed diol stream; and
(B) separating the raffinate phase and the extract phase.

The process of the First Embodiment wherein the mixed diol stream comprises 20 weight percent to 99.5 weight percent ethylene glycol, 20 ppm by weight to 40 weight percent of three-carbon diols, and 20 ppm by weight to 30 weight percent four-carbon diols.

The process of the First Embodiment wherein the mixed diol stream comprises 10 weight percent to 60 weight percent ethylene glycol, 40 weight percent to 90 weight percent three-carbon diols, and 0.1 weight percent to 10 weight percent four-carbon diols.

The process of the First Embodiment wherein the mixed diol stream comprises 20 weight percent to 45 weight percent ethylene glycol, 50 weight percent to 65 weight percent three-carbon diols, and 3 weight percent to 9 weight percent four-carbon diols.

The process of the First Embodiment wherein the mixed diol stream comprises 20 weight percent to 60 weight percent ethylene glycol, 30 weight percent to 70 weight percent three-carbon diols, and 5 weight percent to 25 weight percent four-carbon diols.

The process of the First Embodiment or the First Embodiment with any one or more of the intervening features, wherein said mixed diol stream comprises from 0.5 weight percent to 25 weight percent water, 5 weight percent to 50 weight percent water, 5 weight percent to 35 weight percent water, 10 weight percent to 40 weight percent water, or 15 weight percent to 35 weight percent water.

The process of the First Embodiment or the First Embodiment with any one or more of the intervening features, wherein said hydrophobic solvent is selected from 2-ethylhexanol, cyclohexanol, n-hexanol, methyl isobutyl ketone, methyl isopropyl ketone, methyl propyl ketone, diisobutyl ketone, trioctylphosphine oxide, trihexylphosphine oxide, and mixtures thereof.

The process of the First Embodiment or the First Embodiment with any one or more of the intervening features, wherein said hydrophobic solvent is selected from 2-ethylhexanol, cyclohexanol, trioctylphosphine oxide, trihexylphosphine oxide, and mixtures thereof.

The process of the First Embodiment or the First Embodiment with any one or more of the intervening features, wherein said hydrophobic solvent is selected from 2-ethylhexanol, trioctylphosphine oxide, trihexylphosphine oxide, and mixtures thereof.

The process of the First Embodiment or the First Embodiment with any one or more of the intervening features, wherein said second modifying hydrophobic solvent is selected from hexane, heptane, octane, decane, benzene, toluene, xylenes, isoparaffinic mixed hydrocarbons having a boiling range between 90 and 325° C., methyl napththalenes, and mixtures thereof.

The process of the First Embodiment or the First Embodiment with any one or more of the intervening features, wherein said second modifying hydrophobic solvent is selected from heptane, decane, isoparaffinic mixed hydrocarbons having a boiling range between 90 and 325° C., and mixtures thereof.

The process of the First Embodiment or the First Embodiment with any one or more of the intervening features, wherein said extractant comprises 50 weight percent to 100 weight percent of said hydrophobic solvent and 0 weight percent to 50 weight percent of said second modifying hydrophobic solvent, or 60 weight percent to 95 weight percent of said hydrophobic solvent and 5 weight percent to 40 weight percent of said second modifying hydrophobic solvent, or 70 weight percent to 90 weight percent of said hydrophobic solvent and 10 weight percent to 30 weight percent of said second modifying hydrophobic solvent.

The process of the First Embodiment or the First Embodiment with any one or more of the intervening features, wherein greater than 95 weight percent, or greater than 98 weight percent, or greater than 99 weight percent, or greater than 99.5 weight percent, or greater than 99.9 weight percent of said ethylene glycol in said mixed diol stream is recovered in said raffinate phase.

The process of the First Embodiment or the First Embodiment with any one or more of the intervening features, wherein greater than 80 weight percent, or greater than 85 weight percent, or greater than 90 weight percent, or greater than 95 weight percent, or greater than 98 weight percent, or greater than 99 weight percent, or greater than 99.9 weight percent of said four-carbon diols are recovered in said extract phase.

The process of the First Embodiment or the First Embodiment with any one or more of the intervening features, wherein the purity of said ethylene glycol in said raffinate phase is greater than 95 weight percent, or greater than 98 weight percent, or greater than 99 weight percent, or greater than 99.9 weight percent, or greater than 99.99 weight percent, based the total weight of said diols.

The process of the First Embodiment or the First Embodiment with any one or more of the intervening features, wherein the total amount of said three-carbon diols and said four-carbon diols in said raffinate phase is less than 5 weight percent, less than 1 weight percent, less than 0.5 weight percent, less than 1000 ppm by weight, less than 500 ppm by weight, or less than 100 ppm by weight, based on the total weight of said diols.

The process of the First Embodiment or the First Embodiment with any one or more of the intervening features, wherein said extraction occurs in a continuous counter-current extractor, wherein said extractant is fed lower to said extractor than said mixed diol stream, and wherein the feed ratio of said extractant to said mixed diol stream ranges from 0.5:1 to 20:1, or 1:1 to 10:1, or 1:1 to 5:1.

The process of the First Embodiment or the First Embodiment with any one or more of the intervening features, wherein said extraction occurs in a continuous counter-current extractor, wherein said extractant is fed lower to said extractor than said mixed diol stream, and wherein the feed ratio of said extractant to said mixed diol stream ranges from 0.5:1 to 20:1, or 1:1 to 10:1, or 1:1 to 5:1, further comprising feeding a hydrophilic stream to said extractor at a higher level than said mixed diol stream and wherein the feed ratio of said hydrophilic stream to said mixed diol stream ranges from 0.05:1 to 2:1, or 0.1:1 to 1.5:1, or 0.1:1 to 0.8:1.

The process of the First Embodiment or the First Embodiment with any one or more of the intervening features, wherein said extraction occurs in a continuous counter-current extractor, wherein said extractant is fed lower to said extractor than said mixed diol stream, and wherein the feed ratio of said extractant to said mixed diol stream ranges from 0.5:1 to 20:1, or 1:1 to 10:1, or 1:1 to 5:1, further comprising feeding a hydrophilic stream to said extractor at a higher level than said mixed diol stream and wherein the feed ratio of said hydrophilic stream to said mixed diol stream ranges from 0.05:1 to 2:1, or 0.1:1 to 1.5:1, or 0.1:1 to 0.8:1, and wherein the hydrophilic stream comprises water.

The process of the First Embodiment or the First Embodiment with any one or more of the intervening features, wherein said extraction occurs in a continuous counter-current extractor, wherein said extractant is fed lower to said extractor than said mixed diol stream, and wherein the feed ratio of said extractant to said mixed diol stream ranges from 0.5:1 to 20:1, or 1:1 to 10:1, or 1:1 to 5:1, wherein said hydrophilic solvent comprises water, and wherein said extraction occurs in said extractor over 4 to 20 theoretical stages, or over 6 to 18 theoretical stages, or over 10 to 15 theoretical stages.

The process of the First Embodiment or the First Embodiment with any one or more of the intervening features, further comprising removing a majority of said three-carbon diols and said four-carbon diols from said extract phase to form a lean solvent and recycling said lean solvent, whereby said extractant comprises at least a portion of said lean solvent.

The process of the First Embodiment or the First Embodiment with any one or more of the intervening features, further comprising removing a majority of said three-carbon diols and said four-carbon diols from said extract phase to form a lean solvent and recycling said lean solvent whereby said extractant comprises at least a portion of said lean solvent, wherein the removing occurs through back extraction or through distillation.

A Second Embodiment is a process for recovering purified ethylene glycol from a mixed diol stream, comprising
(A) extracting the mixed diol stream, comprising
  (i) 20 weight percent to 99.5 weight percent, ethylene glycol;
  (ii) 20 ppm by weight to 40 weight percent of one or more three-carbon diols selected from 1,2-propanediol and 1,3-propanediol, and 20 ppm by weight to 30 weight percent of one or more four-carbon diols selected from 1,2-butanediol, 1,3-butanediol, 1,4-butanediol, and 2,3-butanediol; each based on the total weight of diols, and
  (iii) 5 weight percent to 35 weight percent water, based on the total weight of diols and water, with an extractant, comprising
  (i) a hydrophobic solvent selected from 2-ethylhexanol, cyclohexanol, n-hexanol, methyl isobutyl ketone, methyl isopropyl ketone, methyl propyl ketone, diisobutyl ketone, trioctylphosphine oxide, trihexylphosphine oxide, and mixtures thereof; and (ii) optionally, a second modifying hydrophobic solvent selected from hexane, heptane, octane, decane, benzene, toluene, xylenes, isoparaffinic mixed hydrocarbons having a boiling range between 90 and 325° C., methyl napththalenes, and mixtures thereof;

to form a raffinate phase comprising a major amount of the ethylene glycol and a minor amount of the three-carbon diols and/or four-carbon diols contained in the mixed diol stream and an extract phase comprising a major amount of the three-carbon diols and/or four-carbon diols and a minor amount of the ethylene glycol contained in the mixed diol stream; and (B) separating the raffinate phase and the extract phase.

The process of the Second Embodiment wherein greater than 95 weight percent, or greater than 99 weight percent, or greater than 99.5 weight percent of said ethylene glycol in said mixed diol stream is recovered in said raffinate phase, and wherein greater than 60 weight percent, or greater than 80 weight percent, or greater than 90 weight percent of said four-carbon diols is recovered in said extract phase, and wherein the concentration of said ethylene glycol in said raffinate phase is greater than 95 weight percent, or greater than 99 weight percent, or greater than 99.5 weight percent and the concentration of said three-carbon diols and said four-carbon diols combined in said raffinate is less than 1 weight percent, or less than 1000 ppm, or less than 500 ppm, each based on the total weight of said diols.

The process of the Second Embodiment or the Second Embodiment with any one or more of the intervening features wherein said extraction occurs in a continuous counter-current extractor, wherein said extractant is fed lower to said extractor than said mixed diol stream, wherein the feed ratio of said extractant to said mixed diol stream ranges from 0.5:1 to 20:1, or 1:1 to 10:1, or 1:1 to 5:1; further comprising feeding a hydrophilic stream to said extractor at a higher level than said mixed diol stream, wherein the feed ratio of said hydrophilic stream to said mixed diol stream ranges from 0.05:1 to 2:1, or 0.1:1 to 1.5:1, or 0.1:1 to 0.8:1; and wherein said hydrophilic stream comprises water.

A Third embodiment is a process for recovering purified ethylene glycol from a mixed diol stream comprising ethylene glycol and four-carbon diols, comprising (A) extracting the mixed diol stream, comprising
(i) 50 weight percent to 99.99 weight percent ethylene glycol;
(ii) 0.01 weight percent to 50 weight percent of one or more four-carbon diols selected from 1,2-butanediol, 1,3-butanediol, 1,4-butanediol, and 2,3-butanediol; each based on the total weight of diols, and
(iii) 0 weight percent to 50 weight percent water, based on the total weight of diols and water, with an extractant, comprising
(i) a hydrophobic solvent selected from alkanols having from 6 to 20 carbon atoms, ketones having from 5 to 20 carbon atoms, esters having from 5 to 20 carbon atoms, ethers having from 5 to 20 carbon atoms, carboxylic acids having from 5 to 20 carbon atoms, trialkylphosphine oxides having from 18 to 48 carbon atoms, and mixtures thereof; and
(ii) optionally, a second modifying hydrophobic solvent selected from hydrocarbons having from 5 to 20 carbon atoms; to form a raffinate phase comprising a major amount of the ethylene glycol and a minor amount of the four-carbon diols contained in the mixed diol stream and an extract phase comprising a major amount of the four-carbon diols and a minor amount of the ethylene glycol contained in the mixed diol stream; and (B) separating the raffinate phase and the extract phase.

The process of the Third Embodiment wherein said hydrophobic solvent is selected from 2-ethylhexanol, cyclohexanol, n-hexanol, methyl isobutyl ketone, methyl isopropyl ketone, methyl propyl ketone, diisobutyl ketone, trioctylphosphine oxide, trihexylphosphine oxide, and mixtures thereof.

The process of the Third Embodiment or the Third Embodiment with any one or more of the intervening features wherein greater than 95 weight percent, greater than 99 weight percent, or greater than 99.5 weight percent of said ethylene glycol in said mixed diol stream is recovered in said raffinate phase, and wherein greater than 60 weight percent, or greater than 80 weight percent, or greater than 90 weight percent of said four-carbon diols is recovered in said extract phase, and wherein the concentration of said ethylene glycol in said raffinate phase is greater than 95 weight percent, or greater than 99 weight percent, or greater than 99.5 weight percent and the concentration of said four-carbon diols in said raffinate is less than 1 weight percent, or less than 1000 ppm, or less than 500 ppm, each based on the total weight of said diols.

The process of the Third Embodiment or the Third Embodiment with any one or more of the intervening features wherein said extraction occurs in a continuous counter-current extractor, wherein said extractant is fed lower to said extractor than said mixed diol stream, wherein the feed ratio of said extractant to said mixed diol stream ranges from 0.5:1 to 20:1, or 1:1 to 10:1, or 1:1 to 5:1; further comprising feeding a hydrophilic stream to said extractor at a higher level than said mixed diol stream, wherein the feed ratio of said hydrophilic stream to said mixed diol stream ranges from 0.05:1 to 2:1, or 0.1:1 to 1.5:1, or 0.1:1 to 0.8:1; and wherein said hydrophilic stream comprises water.

A Fourth Embodiment of our invention, is a process for recovering diols from a mixed diol stream, comprising (A) extracting the mixed diol stream, comprising
(i) 0.1 weight percent to 50 weight percent of one or more diols selected from ethylene glycol, 1,2-propanediol, 1,3-propanediol 1,2-butanediol, 1,3-butanediol, 1,4-butanediol, and 2,3-butanediol;
(ii) 5 weight percent to 90 weight percent glycerol; and
(iii) 5 weight percent to 90 weight percent water; each based on the total weight of the mixed diol stream with an extractant, comprising
(i) a hydrophobic solvent selected from alkanols having from 6 to 20 carbon atoms, ketones having from 5 to 20 carbon atoms, esters having from 5 to 20 carbon atoms, ethers having from 5 to 20 carbon atoms, carboxylic acids having from 5 to 20 carbon atoms, trialkylphosphine oxides having from 18 to 48 carbon atoms, and mixtures thereof; and
(ii) optionally, a second modifying hydrophobic solvent selected from hydrocarbons having from 5 to 20 carbon atoms; to form a raffinate phase comprising a major amount of the glycerol and a minor amount of the diols contained in the mixed diol stream and an extract phase comprising a major amount of the diols and a minor amount of the glycerol contained in the mixed diol stream; and (B) separating the raffinate phase and the extract phase.

The process of the Fourth Embodiment wherein said hydrophobic solvent is selected from 2-ethylhexanol, cyclohexanol, n-hexanol, methyl isobutyl ketone, methyl isopropyl ketone, methyl propyl ketone, diisobutyl ketone, trioctylphosphine oxide, trihexylphosphine oxide, and mixtures thereof.

The process of the Fourth Embodiment or the Fourth Embodiment with any one or more intervening features wherein greater than 90 weight percent, greater than 95 weight percent, greater than 98 weight percent, greater than 99 weight percent, or greater than 99.5 weight percent of said glycerol is recovered in said raffinate phase and wherein greater than 60 weight percent, greater than 70 weight percent, greater than 80 weight percent, greater than 90 weight percent, greater than 98 weight percent, or greater than 99 weight percent of said diols is recovered in said extract phase.

The process of the Fourth Embodiment or the Fourth Embodiment with any one or more of the intervening features wherein said extraction occurs in a continuous counter-current extractor, wherein said extractant is fed lower to said extractor than said mixed diol stream, wherein the feed ratio of said extractant to said mixed diol stream ranges from 0.5:1 to 20:1, or 1:1 to 10:1, or 1:1 to 5:1; further comprising feeding a hydrophilic stream to said extractor at a higher level than said mixed diol stream, wherein the feed ratio of said hydrophilic stream to said mixed diol stream ranges from 0.05:1 to 2:1, or 0.1:1 to 1.5:1, or 0.1:1 to 0.8:1, and wherein said hydrophilic stream comprises water.

A Fifth Embodiment of our invention, is a process for recovering diols from a mixed diol stream, comprising
(A) extracting the mixed diol stream, comprising
  (i) 0.1 weight percent to 30 weight percent of ethylene glycol, 1,2-propanediol and 1,3-propanediol, 1,2-butanediol, 1,3-butanediol, 1,4-butanediol, and 2,3-butanediol;
  (ii) 5 to 50 weight percent glucose; and
  (iii) 50 weight percent to 90 weight percent water; each based on the total weight of the mixed diol stream, with an extractant, comprising
  (i) a hydrophobic solvent selected from alkanols having from 6 to 20 carbon atoms, ketones having from 5 to 20 carbon atoms, esters having from 5 to 20 carbon atoms, ethers having from 5 to 20 carbon atoms, carboxylic acids having from 5 to 20 carbon atoms, trialkylphosphine oxides having from 18 to 48 carbon atoms, and mixtures thereof; and
  (ii) optionally, a second modifying hydrophobic solvent selected from hydrocarbons having from 5 to 20 carbon atoms; to form a raffinate phase comprising a major amount of the glucose and a minor amount of the diols contained in the mixed diol stream and an extract phase comprising a major amount of the diols and a minor amount of the glucose contained in the mixed diol stream; and
(B) separating the raffinate phase and the extract phase.

The process of the Fifth Embodiment wherein said hydrophobic solvent is selected from 2-ethylhexanol, cyclohexanol, n-hexanol, methyl isobutyl ketone, methyl isopropyl ketone, methyl propyl ketone, diisobutyl ketone, trioctylphosphine oxide, trihexylphosphine oxide, and mixtures thereof.

The process of the Fifth Embodiment or the Fifth Embodiment with any one or more of the intervening features wherein greater than 90 weight percent, greater than 95 weight percent, greater than 98 weight percent, greater than 99 weight percent, or greater than 99.5 weight percent of said glucose is recovered in said raffinate phase and wherein greater than 60 weight percent, greater than 70 weight percent, greater than 80 weight percent, greater than 90 weight percent, greater than 98 weight percent, or greater than 99 weight percent of diols is recovered in said extract phase.

The process of the Fifth Embodiment or the Fifth Embodiment with any one or more of the intervening features wherein said extraction occurs in a continuous counter-current extractor, wherein said extractant is fed lower to said extractor than said mixed diol stream, wherein the feed ratio of said extractant to said mixed diol stream ranges from 0.5:1 to 20:1, or 1:1 to 10:1, or 1:1 to 5:1; further comprising feeding a hydrophilic stream to said extractor at a higher level than said mixed diol stream, wherein the feed ratio of said hydrophilic stream to said mixed diol stream ranges from 0.05:1 to 2:1, or 0.1:1 to 1.5:1, or 0.1:1 to 0.8:1, and wherein said hydrophilic stream comprises water.

A Sixth Embodiment is a process for recovering purified three-carbon diols from a mixed diol stream comprising propanediols and butanediols, comprising
(A) extracting the mixed diol stream, comprising
  (i) 1 weight percent to 99.5 weight percent of one or more three-carbon diols selected from 1,2-propanediol and 1,3-propanediol;
  (ii) 20 ppm by weight to 99 weight percent of one or more four-carbon diols selected from 1,2-butanediol, 1,3-butanediol, 1,4-butanediol, and 2,3-butanediol; each based on the total weight of diols, and
  (iii) 0 weight percent to 50 weight percent water, based on the total weight of diols and water, with an extractant, comprising
  (i) a hydrophobic solvent selected from alkanols having from 6 to 20 carbon atoms, ketones having from 5 to 20 carbon atoms, esters having from 5 to 20 carbon atoms, ethers having from 5 to 20 carbon atoms, carboxylic acids having from 5 to 20 carbon atoms, trialkylphosphine oxides having from 18 to 48 carbon atoms, and mixtures thereof; and
  (ii) optionally, a second modifying hydrophobic solvent selected from hydrocarbons having from 5 to 20 carbon atoms; to form a raffinate phase comprising a major amount of the three-carbon diols and a minor amount of the four-carbon diols contained in the mixed diol stream and an extract phase comprising a major amount of four four-carbon diols and a minor amount of the three-carbon diols contained in the mixed diol stream; and
(B) separating the raffinate phase and the extract phase.

The process of the Sixth Embodiment wherein said hydrophobic solvent is selected from 2-ethylhexanol, cyclohexanol, n-hexanol, methyl isobutyl ketone, methyl isopropyl ketone, methyl propyl ketone, diisobutyl ketone, trioctylphosphine oxide, trihexylphosphine oxide, and mixtures thereof.

The process of the Sixth Embodiment or the Sixth Embodiment with any one or more of the intervening features wherein greater than 95 weight percent, greater than 99 weight percent, or greater than 99.5 weight percent of said three-carbon diols in said mixed diol stream is recovered in said raffinate phase, and wherein greater than 60 weight percent, or greater than 80 weight percent, or greater than 90 weight percent of said four-carbon diols is recovered in said extract phase, and wherein the concentration of said three-carbon diols in said raffinate phase is greater than 95 weight percent, or greater than 99 weight percent, or greater than 99.5 weight percent and the concentration of said four-carbon diols in said raffinate is less than 1 weight percent, or less than 1000 ppm, or less than 500 ppm, each based on the total weight of said diols.

The process of the Sixth Embodiment or the Sixth Embodiment with any one or more of the intervening features wherein said extraction occurs in a continuous counter-current extractor, wherein said extractant is fed lower to said extractor than said mixed diol stream, wherein the feed ratio of said extractant to said mixed diol stream ranges from 0.5:1 to 20:1, or 1:1 to 10:1, or 1:1 to 5:1; further comprising feeding a hydrophilic stream to said extractor at a higher level than said mixed diol stream, wherein the feed ratio of said hydrophilic stream to said mixed diol stream ranges from 0.05:1 to 2:1, or 0.1:1 to 1.5:1, or 0.1:1 to 0.8:1; and wherein said hydrophilic stream comprises water.

The invention is further illustrated by the following, non-limiting examples.

EXAMPLES

General

Analyses of mixed diol products and various extraction phases were carried out by gas chromatography ("GC") using the following procedure. The components from the glycolic acid hydrogenation reaction were first reacted with BSTFA [N,O-bis(trimethylsilyl)trifluoroacetamide] in the presence of pyridine to the corresponding TMS-derivatives including water, which were then separated and quantified by an internal standard (decane) wt % calibrated GC method. The sample to derivatization reagent (BSTFA and pyridine) ratio was 0.1 g:1 ml:0.2 ml in a GC vial, which was heated at 80° C. for 30 minutes to ensure complete derivatization. The GC method used a DB-1301 capillary column or equivalent (6% cyanopropylphenyl/94% dimethylpolysiloxane stationary phase, 60 meters×0.32 mm ID×1.0 um film thickness), a split injector (280° C.), a flame ionization detector (300° C.), helium carrier gas at a constant linear velocity of 27 cm/sec (a Shimadzu GC 2010 or equivalent) or at an initial column head pressure of 17 psi, an oven temperature program of 80° C. initial temp for 6 min, 4° C./min temp ramp rate to 150° C. for 0 min and 10° C./min temp ramp rate to 290° C. for 17.5 min final hold time. 1-ul of the prepared sample solution was injected with a split ratio of 40:1. The method provided quantification range of 0.01-100 wt % for each analyte within its separation capability.

For all extraction examples the partition coefficient for component A is defined as follows:

$$P(A) = \frac{\text{Weight Percent } A \text{ in Hydrophobic phase}}{\text{Weight Percent } A \text{ in Hydrophilic phase}}$$

Selectivity between components A and B is defined as:

$S(AB)=P(A)/P(B)$

Throughout the examples, the following abbreviations are used in the Tables:

| Compound | Abbreviation |
|---|---|
| (2-(butoxymethyl)-2-((diphenylphosphino)methyl)propane-1,3-diyl)-bis(diphenylphosphine) | BuO-triphos |
| Ethylene glycol | EG |
| 1,3-Butanediol | 1,3-BDO |
| 1,2-Butanediol | 1,2-BDO |
| 1,4-Butanediol | 1,4-BDO |
| 2,3-Butanediol | 2,3-BDO |
| 1,2-Propanediol | 1,2-PDO |
| 1,3-Propanediol | 1,3-PDO |
| Cyanex 923 | C923 |
| 2-Ethylhexanol | 2-EH |
| Isobutyl isobutyrate | IBIB |
| Methyl isobutyl ketone | MIBK |
| Diisopropyl ether | DIPE |
| Ethyl acetate | EA |
| n-butyl acetate | NBA |
| Isobutyl acetate | IBA |
| Isopropyl acetate | IPA |
| n-propyl acetate | NPA |
| Ethylhexyl acetate | EHA |
| Ethyl propionate | EP |
| Methyl valerate | MV |
| n-propylpropionate | NPP |
| Methyl propionate | MP |
| Methyl butyrate | MB |
| 5-ethyl-2-nonanone | 5E2N |
| 2-heptanone | MAK |
| Diisobutyl ketone | DIBK |
| 3-methyl-2-butanone | MIPK |
| 6-methyl-2-hexanone | MIAK |
| TXIB | TXIB |
| Tert-butyl methyl ether | MTBE |
| Dibutyl ether | DBE |
| Diethyleneglycol dibutyl ether | DEGDBE |
| Toluene | TOL |
| 2-pentanone | MPK |
| Propylene carbonate | PC |
| N-Hexanol | NH |
| Cyclohexanol | CH |
| Isophorone | IPH |
| n-Decanol | ND |
| n-Heptane | HEP |

Glycolic Acid/Ester Feed and Extractant Mixture

A mixture glycolic acid and glycolate esters was prepared by heating a mixture of 4000 g of glycolic acid and 1795 grams of ethylene glycol at a temperature of about 100 to about 150° C. under atmospheric pressure while removing the water with a Dean-Stark trap. After approximately 860 g of water were removed, the reaction pressure was lowered to 25 torr and the reaction was continued until a total 947 g of water were collected. Mixtures of glycolic acid and glycolate esters prepared according to this procedure typically contained about 2 wt % ethylene glycol, 4 wt % glycolic acid, 2 wt % glycolic acid dimer, 32 wt % glycolic acid monoesters of ethylene glycol (23 wt % glycolic acid monomer ester of EG, 8 wt % glycolic acid dimer monoester of EG, 2 wt % glycolic acid trimer monoester of EG), and 60 wt % bis-glycolate esters of EG (19 wt % glycolic acid monomer diester of EG, 11 wt % glycolic acid dimer/glycolic acid monomer diester of EG, 4 wt % glycolic acid trimer/glycolic acid monomer diester of EG, 30 wt % higher glycolic acid oligomer diesters of EG). The above weight percentages are shown for the components that were detected by GC and do not represent all of the components present in the glycolic acid/ester mixture because of the presence of higher molecular weight oligomers of glycolic acid that do not elute leanly by gas chromatography. These mixtures were used as the feed for glycolic acid hydrogenation reaction as described in Example 2 below.

Example 1

Synthesis of Pentaerythrityl Trichlorohydrin (IX)

A five liter three neck round-bottom flask equipped with an overheard stirrer, a condenser (with a nitrogen purge and a Vigreux column to scrub off any sulfur dioxide), a "Y" connector, with a thermocouple in one side and an addition funnel in the other, was charged with 417 g (3.00 mol) of pentaerythritol and 730 g (9.24 mol) of pyridine. With vigorous stirring, 1134 g (9.24 mol) of thionyl chloride was charged drop wise over a period of 3 hours and 45 minutes and the mixture was heated to 125° C. and held at 125° C. overnight. The brown-yellow solution was cooled to room temperature and 2 L of cold, deionized water was charged with stirring. The precipitate was filtered and washed with 2.5 L of cold, deionized water. The vacuum-dried crude product, (459.7 g), a 1:3.1 mixture of pentaerythrityl trichlorohydrin (VIII) and pentaerythriltetrachloride (IX) as determined by NMR, was separated using fractional distillation under reduced pressure and recrystallized from cyclohexane to yield 253.5 g of (8). $^1$H NMR of 8 (CDCl$^3$): δ 3.74 (s, 3H); 3.66 (s, 6H); 1.72 (br, 1H). $^{13}$C{1H} NMR of 8 (CDCl$^3$): δ 61.2, 46.7, 44.0 ppm.

Synthesis of 1-(3-Chloro-2,2-bis(chloromethyl)propoxy)butane (X)

A 300 mL four neck round-bottom flask equipped with an overheard stirrer, a condenser (with a nitrogen purge) and a thermocouple was charged with 10 g (0.050 mol) of (VIII), 21.68 g (0.16 mol) of 1-bromobutane and 52.50 mL of anhydrous DMSO. The flask was cooled in an ice/water bath and 12.72 g (0.21 mol) of finely ground KOH was charged with vigorous stirring. When no further exotherm was observed, the reaction mixture was heated to 60° C. for 3 hours with stirring. After cooling to room temperature, 225 mL of deionized water was charged slowly. The aqueous phase was extracted with dichloromethane (50 mL) four times. The combined organic layers were washed with 250 mL of 2M HCl, 2×150 mL of deionized water and then dried over Na$_2$SO$_4$. After filtration, the solvent was removed using a rotary evaporator. Product (X) was obtained as a faint yellow liquid. Yield: 11.20 g (0.042 mol, 80%). $^1$H NMR (CDCl$_3$): δ 3.65 (s, 6H); 3.46 (s, 2H); 3.44 (t, 2H); 1.56 (m, 2H); 1.36 (m, 2H); 0.92 (m, 3H). $^{13}$C{1H} NMR (CDCl$_3$): δ 71.4, 68.0, 46.2, 44.5, 31.6, 19.3, 13.8 ppm.

Synthesis of (2-(butoxymethyl)-2-((diphenylphosphino)methyl)propane-1,3-diyl)bis(diphenylphosphine) (IV)

A 500 mL three neck round-bottom flask containing 283 g (0.30 mol) of a diethoxymethane (DEM) solution of lithium diphenylphosphide was cooled to −78° C. using a dry ice/acetone bath. To this solution, 23.75 g (0.10 mol) of compound (X) was charged over a period of 30 minutes with an Argon purge. After all of compound (X) was charged, the acetone/dry ice bath was removed, the mixture was allowed to warm to room temperature, and stirred overnight. All volatiles were removed under vacuum, and the residue was extracted with 50 mL of toluene two times. The extract was washed with 50 mL of deionized water three times. The organic phase was dried over Na$_2$SO$_4$, filtered, and the volatiles were removed under vacuum. 49.5 g (about 74% crude yield and 92% purity) of sticky solid was obtained after drying overnight under vaccum. $^{31}$P{1H} NMR (CDCl$_3$): δ −26.3 ppm (s). $^1$H NMR (CDCl$_3$): δ 7.50-7.34 (m, 30H); 3.29 (s, 2H); 2.85 (t, 2H); 2.71 (s, 6H); 1.24 m (5H); 0.90 (t, 3H). $^{13}$C{1H} NMR (CDCl$_3$): δ 139.9 (d), 132.9 (d), 128.0 (s), 76.1 (q), 70.3 (s), 42.5 (q), 38.2 (m), 31.4 (s), 19.2 (s), 14.0 (s) ppm.

Example 2

Hydrogenation of Glycolic Acid and Glycolate Esters

A mixture comprising 70 ml ethylene glycol, and 6 mL of the glycolic acid/ester feed mixture described above, containing 5 weight percent water, and (2-(butoxymethyl)-2-((diphenylphosphino)methyl)propane-1,3-diyl)bis(diphenylphosphine) ruthenium diacetate (referred to herein as "(BuO-triphos)Ru(OAc)$_2$") at a concentration of 100 ppm Ru metal was loaded into a high pressure Hastelloy C autoclave. The autoclave, nominally 100 mL volume, was fitted with a Rushton turbine impeller, baffles, thermowell, and gas inlet tube. The reactor vessel was heated electrically to 190° C. by a band heater, with temperature control provided by feedback via a K-type thermocouple in the autoclave thermowell. Pure hydrogen gas (>99.9 volume %) was fed to the autoclave via a Brooks flow controller, with pressure maintained at 124.1 bars gauge (1800 psig). After the initial charge, a stock solution of the glycolic acid/ester feed mixture described above containing 5 weight percent water and (butoxy-triphos)Ru(OAc)$_2$, at a concentration of 100 ppm Ru metal was fed for five hours at a rate of 0.4 mL/min. After five hours, the feed rate was cut to 0.197 mL/min (feed substrate rate of 0.192 ml/min, and the catalyst rate of 0.005 mL/min). Aliquots of reactor material were taken off every five minutes to maintain the liquid level at approximately 71-72.5 mL. The cumulative reactor effluent was found by GC analysis to comprise 85.23 weight percent ethylene glycol, 3.39 weight percent glycolate mono esters of ethylene glycol, 4.5 weight percent water, 0.3 weight percent glycolic acid, and 0.5 weight percent glycolate diesters of ethylene glycol. X-ray analysis showed the reactor effluent to comprise 27.9 ppm Ru metal and 23.5 ppm phosphorus content.

Example 3

This example illustrates the effect of water content in the glycolic acid hydrogenation effluent feed mix and the effect of hydrocarbon content of the extractant on extraction of ethylene glycol, 1,2-butanediol (BDO), and 1,2-propanediol (PDO). In Experiments 3-1 to 3-20, water was added to the reactor effluent generated in Example 2 to give the water content specified in Table 1. In addition, 1 weight percent (on an undiluted reactor effluent basis) each of BDO and PDO was added to the reaction effluent of Example 2. The resulting mixtures were contacted (i.e., mixed vigorously) with a solvent mixture comprising 2-ethylhexanol and heptane in the composition and solvent to feed (S/F) ratio specified in Table 1. Each mixture was held at 60° C., allowed to separate into two clear phases and analyzed by GC to determine EG, 1,2-PDO, 1,2-BDO weight percentages which were used to calculate partition coefficients (P) of ethylene glycol, 1,2-BDO, and 1,2-PDO and selectivities between EG and the two other diols. The ethylene glycol, 1,2-propanediol, and 1,2-butanediol partition coefficients (abbreviated as P(EG), P(1,2-PDO), and P(1,2-BDO)) and selectivities (abbreviated as S(1,2-PDO/EG), and S(1,2-BDO/EG)) are summarized in Table 1.

TABLE 1

| Ex. | S/F Ratio | Wt % Water in Feed Mix | Wt % Heptane in Solvent Mix | P(EG) | P(1,2-PDO) | P(1,2-BDO) | S(1,2-PDO/EG) | S(1,2-BDO/EG) |
|---|---|---|---|---|---|---|---|---|
| 3-1 | 0.99 | 9.89% | 0.0% | 0.46 | 0.63 | 0.87 | 1.37 | 1.89 |
| 3-2 | 1.00 | 14.00% | 0.0% | 0.31 | 0.50 | 0.79 | 1.61 | 2.55 |
| 3-3 | 0.99 | 23.71% | 0.0% | 0.21 | 0.37 | 0.68 | 1.76 | 3.24 |
| 3-4 | 1.00 | 33.25% | 0.0% | 0.16 | 0.31 | 0.63 | 1.94 | 3.94 |
| 3-5 | 1.00 | 9.89% | 10.0% | 0.32 | 0.48 | 0.72 | 1.50 | 2.25 |
| 3-6 | 0.99 | 14.00% | 10.0% | 0.23 | 0.39 | 0.65 | 1.70 | 2.83 |
| 3-7 | 1.01 | 23.71% | 10.0% | 0.16 | 0.31 | 0.58 | 1.94 | 3.63 |
| 3-8 | 1.00 | 33.25% | 10.0% | 0.12 | 0.25 | 0.53 | 2.08 | 4.42 |
| 3-9 | 1.00 | 9.89% | 15.1% | 0.26 | 0.41 | 0.64 | 1.58 | 2.46 |
| 3-10 | 1.01 | 14.00% | 15.1% | 0.20 | 0.35 | 0.58 | 1.75 | 2.90 |
| 3-11 | 1.00 | 23.71% | 15.1% | 0.14 | 0.27 | 0.53 | 1.93 | 3.79 |
| 3-12 | 1.00 | 33.25% | 15.1% | 0.11 | 0.23 | 0.48 | 2.09 | 4.36 |
| 3-13 | 1.00 | 9.89% | 20.0% | 0.22 | 0.36 | 0.58 | 1.64 | 2.64 |
| 3-14 | 0.99 | 14.00% | 20.0% | 0.18 | 0.31 | 0.54 | 1.72 | 3.00 |
| 3-15 | 1.01 | 23.71% | 20.0% | 0.13 | 0.25 | 0.49 | 1.92 | 3.77 |
| 3-16 | 0.99 | 33.25% | 20.0% | 0.10 | 0.21 | 0.45 | 2.10 | 4.50 |
| 3-17 | 0.99 | 9.89% | 30.0% | 0.16 | 0.27 | 0.45 | 1.69 | 2.81 |
| 3-18 | 1.00 | 14.00% | 30.0% | 0.14 | 0.25 | 0.45 | 1.79 | 3.21 |
| 3-19 | 1.00 | 23.71% | 30.0% | 0.10 | 0.20 | 0.39 | 2.00 | 3.90 |
| 3-20 | 1.00 | 33.25% | 30.0% | 0.08 | 0.17 | 0.37 | 2.13 | 4.63 |

Example 4

A standard ethylene-glycol rich solution was prepared comprising 90 weight percent ethylene glycol (EG), and five weight percent each of 1,2-propanediol (1,2-PDO) and 1,2-butanediol (1,2-BDO). Five grams of this standard solution was added to a separate glass vial along with five grams of each of the nonpolar solvents listed in Table 2. The contents were mixed vigorously and allowed to settle and separate into two clear phases. The phases were analyzed by gas chromatography to determine EG, 1,2-PDO, 1,2-BDO weight percentages. These analytical results were used to calculate partition coefficients and selectivities. All experiments were conducted at room temperature. Results are summarized in Table 2.

TABLE 2

| Ex | Solvent | P(EG) | P(1,2-PDO) | P(1,2-BDO) | S(1,2-PDO/EG) | S(1,2-BDO/EG) |
|---|---|---|---|---|---|---|
| 4-1 | EA | 0.16 | 0.22 | 0.30 | 1.33 | 1.86 |
| 4-2 | NBA | 0.04 | 0.06 | 0.11 | 1.71 | 3.01 |
| 4-3 | IBA | 0.03 | 0.06 | 0.10 | 1.75 | 3.10 |
| 4-4 | IPA | 0.06 | 0.10 | 0.16 | 1.54 | 2.47 |
| 4-5 | IBIB | 0.01 | 0.02 | 0.05 | 2.13 | 4.23 |
| 4-6 | EHA | 0.01 | 0.02 | 0.04 | 2.10 | 4.58 |
| 4-7 | EP | 0.05 | 0.08 | 0.13 | 1.62 | 2.72 |
| 4-8 | MV | 0.03 | 0.05 | 0.09 | 1.70 | 2.96 |
| 4-9 | NPP | 0.03 | 0.05 | 0.09 | 1.83 | 3.28 |
| 4-10 | MP | 0.10 | 0.14 | 0.22 | 1.44 | 2.16 |
| 4-11 | MB | 0.04 | 0.07 | 0.12 | 1.65 | 2.82 |
| 4-12 | 5E2N | 0.02 | 0.12 | 0.11 | 7.08 | 6.57 |
| 4-13 | MAK | 0.07 | 0.10 | 0.17 | 1.50 | 2.49 |
| 4-14 | DIBK | 0.02 | 0.03 | 0.12 | 1.60 | 5.96 |
| 4-15 | MIPK | 0.34 | 0.41 | 0.50 | 1.21 | 1.49 |
| 4-16 | MIAK | 0.07 | 0.11 | 0.17 | 1.52 | 2.48 |
| 4-17 | TXIB | 0.01 | 0.02 | 0.03 | 1.53 | 2.90 |
| 4-18 | MIBK | 0.10 | 0.15 | 0.23 | 1.45 | 2.21 |
| 4-19 | MTBE | 0.05 | 0.08 | 0.15 | 1.74 | 3.15 |
| 4-20 | DIPE | 0.01 | 0.02 | 0.04 | 1.66 | 3.27 |
| 4-21 | DBE | 0.01 | 0.01 | 0.01 | 1.21 | 2.56 |
| 4-22 | DEGDBE | 0.03 | 0.05 | 0.09 | 1.54 | 2.86 |
| 4-23 | TOL | 0.00 | 0.00 | 0.01 | 0.62 | 1.26 |
| 4-24 | MPK | 0.40 | 0.47 | 0.57 | 1.18 | 1.42 |

Example 5

Water was added to the standard ethylene-glycol rich solution prepared for Example 4, comprising 90 weight percent ethylene glycol (EG), and five weight percent each of 1,2-propanediol (1,2-PDO) and 1,2-butanediol (1,2-BDO). The amount of water on a total solution basis was 10 weight percent (i.e., based on the total weight of diols and water). Five grams of this water-containing solution was added to a separate glass vial along with five grams of each of the nonpolar solvents listed in Table 3. The contents were mixed vigorously and allowed to settle and separate into two clear phases. The phases were analyzed by gas chromatography to determine EG, 1,2-PDO, 1,2-BDO weight percentages. These analytical results were used to calculate partition coefficients and selectivities. All experiments were conducted at room temperature. Results are summarized in Table 3.

TABLE 3

| Ex | Solvent | P(EG) | P(1,2-PDO) | P(1,2-BDO) | S(1,2-PDO/EG) | S(1,2-BDO/EG) |
|---|---|---|---|---|---|---|
| 5-1 | NH | 1.09 | 0.51 | 1.03 | 0.47 | 0.95 |
| 5-2 | 2-EH | 0.37 | 0.51 | 0.79 | 1.39 | 2.15 |
| 5-3 | CH | 0.67 | 0.80 | 1.12 | 1.19 | 1.67 |
| 5-4 | EA | 0.10 | 0.15 | 0.24 | 1.45 | 2.33 |
| 5-5 | NBA | 0.03 | 0.05 | 0.10 | 1.87 | 3.68 |
| 5-6 | IBA | 0.03 | 0.05 | 0.09 | 1.84 | 3.76 |
| 5-7 | IPA | 0.05 | 0.08 | 0.14 | 1.71 | 3.12 |
| 5-8 | NPA | 0.01 | 0.02 | 0.04 | 2.19 | 4.77 |
| 5-9 | IBIB | 0.01 | 0.02 | 0.04 | 2.28 | 5.25 |
| 5-10 | EHA | 0.03 | 0.06 | 0.12 | 1.83 | 3.51 |
| 5-11 | EP | 0.02 | 0.04 | 0.08 | 1.93 | 4.15 |
| 5-12 | MV | 0.02 | 0.04 | 0.08 | 2.01 | 4.08 |
| 5-13 | NPP | 0.07 | 0.10 | 0.18 | 1.58 | 2.77 |
| 5-14 | MP | 0.03 | 0.06 | 0.11 | 1.85 | 3.50 |
| 5-15 | MB | 0.02 | 0.03 | 0.09 | 1.75 | 5.45 |
| 5-16 | 5E2N | 0.04 | 0.07 | 0.15 | 1.68 | 3.33 |
| 5-17 | MAK | 0.02 | 0.03 | 0.12 | 1.66 | 7.39 |
| 5-18 | DIBK | 0.16 | 0.22 | 0.34 | 1.42 | 2.15 |
| 5-19 | MIPK | 0.05 | 0.08 | 0.15 | 1.70 | 3.26 |
| 5-20 | MIAK | 0.01 | 0.02 | 0.03 | 1.52 | 3.41 |
| 5-21 | TXIB | 0.06 | 0.11 | 0.19 | 1.64 | 2.95 |
| 5-22 | MIBK | 0.23 | 0.33 | 0.55 | 1.42 | 2.37 |
| 5-23 | IPH | 0.04 | 0.07 | 0.14 | 1.80 | 3.63 |
| 5-24 | MTBE | 0.01 | 0.02 | 0.04 | 1.56 | 3.43 |

TABLE 3-continued

| Ex | Solvent | P(EG) | P(1,2-PDO) | P(1,2-BDO) | S(1,2-PDO/EG) | S(1,2-BDO/EG) |
|---|---|---|---|---|---|---|
| 5-25 | DIPE | 0.01 | 0.01 | 0.02 | 0.95 | 2.51 |
| 5-26 | DBE | 0.03 | 0.04 | 0.09 | 1.61 | 3.38 |
| 5-27 | DEGDBE | 0.00 | 0.00 | 0.01 | 0.58 | 1.56 |
| 5-28 | TOL | 0.00 | 0.00 | 0.01 | 0.57 | 1.46 |
| 5-29 | PC | 3.02 | 2.74 | 2.24 | 0.91 | 0.74 |
| 5-30 | MPK | 0.18 | 0.25 | 0.38 | 1.39 | 2.09 |

Example 6

This example illustrates the effect of increased water content on the partition coefficients and selectivities of diols. A standard ethylene-glycol rich solution was prepared comprising 74.8 weight percent ethylene glycol (EG), 15 weight percent water, and 1.7 weight percent each of 1,2-propanediol (1,2-PDO), 1,2-butanediol (1,2-BDO), 1,3-propanediol (1,3-PDO), 2,3-butanediol (2,3-BDO), 1,3-butanediol (1,3-BDO), and 1,4-butanediol (1,4-BDO). Ten grams of this standard solution were added to a separate glass vial along with ten grams of each of the hydrophobic solvent mixtures listed in Table 4a. The contents were mixed vigorously and allowed to settle and separate into two clear phases and analyzed by gas chromatography to determine weight percentages of each of the diols. These analytical results were used to calculate partition coefficients (Table 4b) and selectivities (Table 4c). All experiments were conducted at 60 degrees Celsius.

TABLE 4a

| Ex | Hydrophobic Solvent 1 | Hydrophobic Solvent 2 | Wt % Solvent 1 | Wt % Solvent 2 |
|---|---|---|---|---|
| 6-1 | EA | — | 100% | 0% |
| 6-2 | DIBK | — | 100% | 0% |
| 6-3 | MIBK | — | 100% | 0% |
| 6-4 | 2-EH | — | 100% | 0% |
| 6-5 | 2-EH | HEP | 90% | 10% |
| 6-6 | 2-EH | HEP | 80% | 20% |
| 6-7 | ND | — | 100% | 0% |
| 6-8 | ND | HEP | 90% | 10% |
| 6-9 | ND | HEP | 80% | 20% |

TABLE 4b

| Ex | P(EG) | P(1,2-PDO) | P(2,3-BDO) | P(1,3-PDO) | P(1,2-BDO) | P(1,3-BDO) | P(1,4-BDO) |
|---|---|---|---|---|---|---|---|
| 6-1 | 0.18 | 0.27 | 0.44 | 0.19 | 0.41 | 0.30 | 0.23 |
| 6-2 | 0.13 | 0.23 | 0.40 | 0.15 | 0.38 | 0.26 | 0.19 |
| 6-3 | 0.02 | 0.04 | 0.29 | 0.03 | 0.19 | 0.06 | 0.04 |
| 6-4 | 0.02 | 0.03 | 0.31 | 0.03 | 0.22 | 0.05 | 0.04 |
| 6-5 | 0.11 | 0.18 | 0.34 | 0.13 | 0.31 | 0.22 | 0.16 |
| 6-6 | 0.07 | 0.13 | 0.28 | 0.09 | 0.28 | 0.17 | 0.12 |
| 6-7 | 0.37 | 0.53 | 0.76 | 0.47 | 0.79 | 0.62 | 0.52 |
| 6-8 | 0.18 | 0.34 | 0.62 | 0.31 | 0.66 | 0.44 | 0.34 |
| 6-9 | 0.25 | 0.39 | 0.67 | 0.34 | 0.66 | 0.47 | 0.37 |

TABLE 4c

| Ex | S(1,2-PDO/EG) | S(2,3-BDO/EG) | S(1,3-PDO/EG) | S(1,2-BDO/EG) | S(1,3-BDO/EG) | S(1,4-BDO/EG) |
|---|---|---|---|---|---|---|
| 6-1 | 1.51 | 2.42 | 1.07 | 2.25 | 1.65 | 1.25 |
| 6-2 | 1.73 | 3.06 | 1.15 | 2.94 | 1.95 | 1.45 |
| 6-3 | 1.70 | 12.15 | 1.27 | 7.99 | 2.56 | 1.78 |
| 6-4 | 1.85 | 16.84 | 1.45 | 11.75 | 2.92 | 2.30 |
| 6-5 | 1.70 | 3.15 | 1.18 | 2.90 | 2.06 | 1.44 |
| 6-6 | 2.00 | 4.21 | 1.31 | 4.16 | 2.59 | 1.83 |
| 6-7 | 1.45 | 2.07 | 1.29 | 2.16 | 1.68 | 1.42 |
| 6-8 | 1.86 | 3.41 | 1.73 | 3.67 | 2.42 | 1.88 |
| 6-9 | 1.60 | 2.71 | 1.39 | 2.66 | 1.92 | 1.52 |

Example 7

This example illustrates the effect of increased water content on the partition coefficients and selectivities of diols. A standard ethylene-glycol rich solution was prepared comprising 61.6 weight percent ethylene glycol (EG), 30 weight percent water, and 1.4 weight percent each of 1,2-propanediol (1,2-PDO), 1,2-butanediol (1,2-BDO), 1,3-propanediol (1,3-PDO), 2,3-butanediol (2,3-BDO), 1,3-butanediol (1,3-BDO), and 1,4-butanediol (1,4-BDO). Ten grams of this standard solution were added to a separate glass vial along with ten grams of each of the hydrophobic solvent mixtures listed in Table 5a. The contents were mixed vigorously and allowed to settle and separate into two clear phases and analyzed by gas chromatography to determine weight percentages of each of the diols. These analytical results were used to calculate partition coefficients (Table 5b) and selectivities (Table 5c). All experiments were conducted at 60 degrees Celsius.

TABLE 5a

| Ex | Hydrophobic Solvent 1 | Hydrophobic Solvent 2 | Wt % Solvent 1 | Wt % Solvent 2 |
|---|---|---|---|---|
| 7-1 | EA | — | 100% | 0% |
| 7-2 | DIBK | — | 100% | 0% |
| 7-3 | MIBK | — | 100% | 0% |
| 7-4 | 2-EH | — | 100% | 0% |
| 7-5 | 2-EH | HEP | 90% | 10% |
| 7-6 | 2-EH | HEP | 80% | 20% |
| 7-7 | ND | — | 100% | 0% |
| 7-8 | ND | HEP | 90% | 10% |
| 7-9 | ND | HEP | 80% | 20% |

TABLE 5b

| Ex | P(EG) | P(1,2-PDO) | P(2,3-BDO) | P(1,3-PDO) | P(1,2-BDO) | P(1,3-BDO) | P(1,4-BDO) |
|---|---|---|---|---|---|---|---|
| 7-1 | 0.14 | 0.27 | 0.51 | 0.25 | 0.55 | 0.35 | 0.70 |
| 7-2 | 0.18 | 0.30 | 0.54 | 0.25 | 0.52 | 0.36 | 0.27 |
| 7-3 | 0.11 | 0.21 | 0.43 | 0.20 | 0.46 | 0.28 | 0.20 |
| 7-4 | 0.28 | 0.42 | 0.65 | 0.31 | 0.68 | 0.48 | 0.38 |
| 7-5 | 0.15 | 0.26 | 0.50 | 0.18 | 0.55 | 0.34 | 0.26 |
| 7-6 | 0.20 | 0.32 | 0.55 | 0.22 | 0.55 | 0.37 | 0.29 |
| 7-7 | 0.12 | 0.23 | 0.45 | 0.15 | 0.48 | 0.29 | 0.22 |
| 7-8 | 0.15 | 0.26 | 0.47 | 0.17 | 0.47 | 0.31 | 0.23 |
| 7-9 | 0.10 | 0.18 | 0.38 | 0.12 | 0.41 | 0.24 | 0.17 |

TABLE 5c

| Ex | S(1,2-PDO/EG) | S(2,3-BDO/EG) | S(1,3-PDO/EG) | S(1,2-BDO/EG) | S(1,3-BDO/EG) | S(1,4-BDO/EG) |
|---|---|---|---|---|---|---|
| 7-1 | 1.92 | 3.69 | 1.80 | 3.97 | 2.51 | 5.02 |
| 7-2 | 1.69 | 3.07 | 1.44 | 2.95 | 2.03 | 1.53 |
| 7-3 | 2.00 | 3.98 | 1.87 | 4.25 | 2.58 | 1.89 |
| 7-4 | 1.51 | 2.34 | 1.11 | 2.46 | 1.74 | 1.38 |
| 7-5 | 1.77 | 3.32 | 1.22 | 3.65 | 2.27 | 1.73 |
| 7-6 | 1.59 | 2.79 | 1.12 | 2.78 | 1.88 | 1.44 |
| 7-7 | 1.83 | 3.59 | 1.22 | 3.90 | 2.36 | 1.81 |
| 7-8 | 1.67 | 3.06 | 1.12 | 3.05 | 1.98 | 1.46 |
| 7-9 | 1.91 | 3.92 | 1.22 | 4.24 | 2.48 | 1.80 |

Example 8

This example illustrates the back extraction of three-carbon diols and four-carbon diols from a hydrophobic solvent mixture using water. Hydrophobic solvent and diol mixtures were prepared from 2-EH, HEP, EG, 1,2-PDO, 1,2-BDO, 1,3-PDO, 2,3-BDO, 1,3-BDO, and 1,4-BDO. Ten grams of water were added to a separate glass vial along with fifteen grams of each of the hydrophobic solvent mixture as listed in Table 6a. The contents were mixed vigorously and allowed to settle and separate into two clear phases and analyzed by gas chromatography to determine weight percentages of each of the diols. These analytical results were used to calculate partition coefficients (Table 6b) and selectivities (Table 6c). All experiments were conducted at 60 degrees Celsius.

TABLE 6a

| Ex | 2-EH, wt % | HEP, wt % | 1,2-PDO, wt % | 1,2-BDO, wt % | 1,3-PDO, wt % | 1,3-BDO, wt % | 1,4-BDO, wt % | 2,3-BDO, wt % | EG, wt % |
|---|---|---|---|---|---|---|---|---|---|
| 8-1 | 84.6% | 9.4% | 2.0% | 2.0% | 0.0% | 0.0% | 0.0% | 0.0% | 2.0% |
| 8-2 | 75.2% | 18.8% | 2.0% | 2.0% | 0.0% | 0.0% | 0.0% | 0.0% | 2.0% |
| 8-3 | 65.8% | 28.2% | 2.0% | 2.0% | 0.0% | 0.0% | 0.0% | 0.0% | 2.0% |
| 8-4 | 56.4% | 37.6% | 2.0% | 2.0% | 0.0% | 0.0% | 0.0% | 0.0% | 2.0% |
| 8-5 | 77.4% | 8.6% | 2.0% | 2.0% | 2.0% | 2.0% | 2.0% | 2.0% | 2.0% |
| 8-6 | 68.8% | 17.2% | 2.0% | 2.0% | 2.0% | 2.0% | 2.0% | 2.0% | 2.0% |
| 8-7 | 60.2% | 25.8% | 2.0% | 2.0% | 2.0% | 2.0% | 2.0% | 2.0% | 2.0% |
| 8-8 | 51.6% | 34.4% | 2.0% | 2.0% | 2.0% | 2.0% | 2.0% | 2.0% | 2.0% |

TABLE 6b

| Ex | P(1,2-PDO) | P(1,2-BDO) | P(1,3-PDO) | P(1,3-BDO) | P(1,4-BDO) | P(2,3-BDO) | P(EG) |
|---|---|---|---|---|---|---|---|
| 8-1 | 0.087 | 0.28 | N/A | N/A | N/A | N/A | 0.035 |
| 8-2 | 0.075 | 0.24 | N/A | N/A | N/A | N/A | 0.030 |
| 8-3 | 0.061 | 0.20 | N/A | N/A | N/A | N/A | 0.025 |
| 8-4 | 0.050 | 0.17 | N/A | N/A | N/A | N/A | 0.020 |
| 8-5 | 0.101 | 0.31 | 0.11 | 0.17 | 0.13 | 0.19 | 0.043 |
| 8-6 | 0.082 | 0.26 | 0.09 | 0.13 | 0.10 | 0.16 | 0.034 |
| 8-7 | 0.069 | 0.22 | 0.08 | 0.11 | 0.08 | 0.13 | 0.028 |
| 8-8 | 0.056 | 0.18 | 0.06 | 0.09 | 0.06 | 0.11 | 0.022 |

TABLE 6c

| Ex | S(1,2-PDO/EG) | S(1,2-BDO/EG) | S(1,3-PDO/EG) | S(1,3-BDO/EG) | S(1,4-BDO/EG) | S(2,3-BDO/EG) |
|---|---|---|---|---|---|---|
| 8-1 | 2.47 | 8.00 | N/A | N/A | N/A | N/A |
| 8-2 | 2.50 | 8.11 | N/A | N/A | N/A | N/A |
| 8-3 | 2.49 | 8.15 | N/A | N/A | N/A | N/A |
| 8-4 | 2.57 | 8.55 | N/A | N/A | N/A | N/A |
| 8-5 | 2.34 | 7.09 | 2.63 | 3.85 | 3.01 | 4.34 |
| 8-6 | 2.43 | 7.57 | 2.72 | 3.91 | 2.98 | 4.58 |
| 8-7 | 2.48 | 7.84 | 2.76 | 3.89 | 2.87 | 4.73 |
| 8-8 | 2.51 | 7.89 | 2.71 | 3.80 | 2.72 | 4.79 |

Example 9

This example illustrates a second back extraction of diols from a hydrophobic solvent mixture using water. The hydrophobic top phases from examples 8-1 through 8-8 were further contacted with a second aliquot of water. Ten grams of water were added to a separate glass vial along with each of the hydrophobic top phases from examples 8-1 to 8-8 (typically about 13 grams). The contents were mixed vigorously and allowed to settle and separate into two clear phases and analyzed by gas chromatography to determine weight percentages of each of the diols. These analytical results were used to calculate partition coefficients (Table 7a) and selectivities (Table 7b). In examples 9-3 through 9-8, no EG was remaining in the top layers from the first extractions of examples 8-3 through 8-8, so EG-based selectivities could not be calculated. All experiments were conducted at 60 degrees Celsius.

TABLE 7a

| Ex | P(1,2-PDO) | P(1,2-BDO) | P(1,3-PDO) | P(1,3-BDO) | P(1,4-BDO) | P(2,3-BDO) | P(EG) |
|---|---|---|---|---|---|---|---|
| 9-1 | 0.149 | 0.39 | N/A | N/A | N/A | N/A | 0.051 |
| 9-2 | 0.120 | 0.31 | N/A | N/A | N/A | N/A | 0.038 |
| 9-3 | 0.115 | 0.27 | N/A | N/A | N/A | N/A | Not detect |
| 9-4 | 0.099 | 0.22 | N/A | N/A | N/A | N/A | Not detect |
| 9-5 | 0.157 | 0.40 | 0.56 | 0.21 | 0.17 | 0.26 | Not detect |
| 9-6 | 0.136 | 0.33 | 0.59 | 0.17 | 0.13 | 0.21 | Not detect |
| 8-7 | 0.116 | 0.27 | 0.62 | 0.14 | 0.11 | 0.18 | Not detect |
| 9-8 | 0.105 | 0.22 | 0.64 | 0.11 | 0.09 | 0.14 | Not detect |

TABLE 7b

| Ex | S(1,2-PDO/EG) | S(1,2-BDO/EG) | S(1,3-PDO/EG) | S(1,3-BDO/EG) | S(1,4-BDO/EG) | S(2,3-BDO/EG) |
|---|---|---|---|---|---|---|
| 9-1 | 2.90 | 7.52 | N/A | N/A | N/A | N/A |
| 9-2 | 3.18 | 8.19 | N/A | N/A | N/A | N/A |
| 9-3 | N/A | N/A | N/A | N/A | N/A | N/A |
| 9-4 | N/A | N/A | N/A | N/A | N/A | N/A |
| 9-5 | N/A | N/A | N/A | N/A | N/A | N/A |
| 9-6 | N/A | N/A | N/A | N/A | N/A | N/A |
| 8-7 | N/A | N/A | N/A | N/A | N/A | N/A |
| 9-8 | N/A | N/A | N/A | N/A | N/A | N/A |

Example 10

A mixed diol solution was prepared by mixing 1.5 weight percent each of 1,2-propanediol (1,2-PDO) and 1,2-butanediol (1,2-BDO), with the remainder ethylene glycol (EG). Three standard water-diol solutions were prepared by mixing 0 weight percent, 10 weight percent, or 20 weight percent water with the above mixed diol solution, based on the total weight of diol and water. Four standard non-polar solutions were prepared comprising either 1 weight percent, 10 weight percent, 30 weight percent, or 50 weight percent Cyanex® 923 solvent (C923), with the remainder heptane. Another four standard non-polar solutions were prepared comprising either 1 weight percent, 10 weight percent, 30 weight percent, or 50 weight percent C923 solvent, with the remainder toluene. Ten grams of each of the standard ethylene glycol rich solutions were contacted with ten grams of each of the eight Cyanex standard solutions in separate glass vials. The contents were mixed vigorously and allowed to settle and separate into two clear phases. The phases were analyzed by gas chromatography to determine weight percentages of each of the diols in each phase. These analytical results were used to calculate partition coefficients for EG, 1,2-PDO, and 1,2-BDO as shown in Tables 8a, 8b, and 8c respectively. Selectivities over EG are given in Table 8d and Table 8e for 1,2-PDO and 1,2-BDO, respectively. All experiments were conducted at room temperature.

TABLE 8a

| Ex | Cosolvent | wt % C923 in solvent mixture | P(EG) w/0% H2O in Diol Mixture | P(EG) w/10% H2O in Diol Mixture | P(EG) w/20% H2O in Diol Mixture |
|---|---|---|---|---|---|
| 10-1 | Heptane | 1.0% | 0.0016 | 0.0016 | 0.0013 |
| 10-2 | Heptane | 10.0% | 0.0182 | 0.0169 | 0.0157 |
| 10-3 | Heptane | 30.0% | 0.0667 | 0.0614 | 0.0554 |
| 10-4 | Heptane | 50.0% | 0.1268 | 0.1138 | 0.1016 |
| 10-5 | Toluene | 1.0% | 0.0046 | 0.0036 | 0.0033 |
| 10-6 | Toluene | 10.0% | 0.0342 | 0.0229 | 0.0205 |
| 10-7 | Toluene | 30.0% | 0.0917 | 0.0757 | 0.0662 |
| 10-8 | Toluene | 50.0% | 0.1575 | 0.1282 | 0.1177 |

TABLE 8b

| Ex | Cosolvent | wt % C923 in solvent mixture | P(1,2-PDO) w/0% H2O in Diol Mixture | P(1,2-PDO) w/10% H2O in Diol Mixture | P(1,2-PDO) w/20% H2O in Diol Mixture |
|---|---|---|---|---|---|
| 10-1 | Heptane | 1.0% | 0.0034 | 0.0032 | 0.0070 |
| 10-2 | Heptane | 10.0% | 0.0400 | 0.0402 | 0.0351 |
| 10-3 | Heptane | 30.0% | 0.1275 | 0.1282 | 0.1235 |
| 10-4 | Heptane | 50.0% | 0.2241 | 0.2207 | 0.2118 |
| 10-5 | Toluene | 1.0% | 0.0100 | 0.0080 | 0.0088 |
| 10-6 | Toluene | 10.0% | 0.0632 | 0.0486 | 0.0440 |
| 10-7 | Toluene | 30.0% | 0.1581 | 0.1452 | 0.1367 |
| 10-8 | Toluene | 50.0% | 0.2550 | 0.2298 | 0.2286 |

TABLE 8c

| Ex | Cosolvent | wt % C923 in solvent mixture | P(1,2-BDO) w/0% H2O in Diol Mixture | P(1,2-BDO) w/10% H2O in Diol Mixture | P(1,2-BDO) w/20% H2O in Diol Mixture |
|---|---|---|---|---|---|
| 10-1 | Heptane | 1.0% | 0.0134 | 0.0101 | 0.0211 |
| 10-2 | Heptane | 10.0% | 0.0879 | 0.0986 | 0.1054 |
| 10-3 | Heptane | 30.0% | 0.2601 | 0.2966 | 0.3235 |
| 10-4 | Heptane | 50.0% | 0.4432 | 0.4955 | 0.5301 |
| 10-5 | Toluene | 1.0% | 0.0208 | 0.0203 | 0.0000 |
| 10-6 | Toluene | 10.0% | 0.1218 | 0.1117 | 0.1194 |
| 10-7 | Toluene | 30.0% | 0.2989 | 0.3130 | 0.3341 |
| 10-8 | Toluene | 50.0% | 0.4659 | 0.4812 | 0.5448 |

TABLE 8d

| Ex | Cosolvent | wt % C923 in solvent mixture | S(1,2-PDO/EG) w/0% H2O in Diol Mixture | S(1,2-PDO/EG) w/10% H2O in Diol Mixture | S(1,2-PDO/EG) w/20% H2O in Diol Mixture |
|---|---|---|---|---|---|
| 10-1 | Heptane | 1.0% | 2.09 | 2.06 | 5.27 |
| 10-2 | Heptane | 10.0% | 2.20 | 2.37 | 2.24 |
| 10-3 | Heptane | 30.0% | 1.91 | 2.09 | 2.23 |
| 10-4 | Heptane | 50.0% | 1.77 | 1.94 | 2.08 |
| 10-5 | Toluene | 1.0% | 2.18 | 2.23 | 3.03 |
| 10-6 | Toluene | 10.0% | 1.84 | 2.12 | 2.63 |
| 10-7 | Toluene | 30.0% | 1.72 | 1.92 | 2.06 |
| 10-8 | Toluene | 50.0% | 1.62 | 1.79 | 1.94 |

TABLE 8e

| Ex | Cosolvent | wt % C923 in solvent mixture | S(1,2-BDO/EG) w/0% H2O in Diol Mixture | S(1,2-BDO/EG) w/10% H2O in Diol Mixture | S(1,2-BDO/EG) w/20% H2O in Diol Mixture |
|---|---|---|---|---|---|
| 10-1 | Heptane | 1.0% | 8.15 | 6.45 | 15.83 |
| 10-2 | Heptane | 10.0% | 4.83 | 5.82 | 6.73 |
| 10-3 | Heptane | 30.0% | 3.90 | 4.83 | 5.84 |
| 10-4 | Heptane | 50.0% | 3.49 | 4.35 | 5.22 |
| 10-5 | Toluene | 1.0% | 4.53 | 5.66 | 7.13 |
| 10-6 | Toluene | 10.0% | 3.56 | 4.87 | 5.83 |
| 10-7 | Toluene | 30.0% | 3.26 | 4.13 | 5.05 |
| 10-8 | Toluene | 50.0% | 2.96 | 3.75 | 4.63 |

Example 11

An ethylene glycol-rich solution was prepared by mixing 95 weight percent ethylene glycol, and 2.5 weight percent each of 1,2-propanediol and 1,2-butanediol. The resulting mixed diol feed was subjected to a cascaded series of twenty-four cross-flow batch extractions to simulate a six-stage continuous counter-current fractional extraction process, with the mixed diol feed introduced on stage four (from the bottom), the hydrophobic solvent, 2-ethylhexanol (2-EH), introduced on stage one (from bottom), and the water wash on stage six (top of extractor). The multi-cycle, cascaded pattern of 24 extractions in which one mixed diol feed charge is added into the center of the first cycle of the cascade, and multiple hydrophobic solvent and water wash charges are introduced at separate ends of each cycle of the cascade, and with raffinate and extract compositions introduced to the next cycle of the cascade, results in a set of conditions on the final cycle which have been shown to closely approach the equilibrium composition profile of a continuous, staged, counter-current fractional extractor. For this work, three cycles were found to be sufficient to asymptotically approach continuous extraction equilibrium conditions. The simulated counter-current extraction technique used herein is well-known to those skilled in the art and is laid out in detail in Treybal ("Liquid Extraction," 2nd Ed., McGraw-Hill Book Company, New York, N.Y., 1963, pp. 349-366). The water to mixed diol feed weight ratio was 0.4:1.0, and the 2-EH to mixed diol feed ratio was 1.5:1.0. The experiment was conducted at room temperature. The final simulated extract (top product) and raffinate (bottom product) streams were subjected to gas chromatography to determine the compositions of the products. Results are given in Table 9. The percent recovery to the extract is based on the amount of each component in all inputs to the extractor. The solvent free raffinate composition (in weight percent) is calculated based on the total weight of EG, 1,2-PDO, and 1,4-BDO in the raffinate.

TABLE 9

| | Feed | Extract | | Raffinate | |
|---|---|---|---|---|---|
| | Composition of Feed, Wt % | Composition of Extract, Wt % | % Recovery to Extract | Composition of Raffinate, Wt % | Solvent Free Composition, Wt % |
| EG | 95.0% | 0.26% | 0.4% | 69.56% | 97.0% |
| 1,2-BDO | 2.5% | 1.04% | 64.0% | 0.66% | 0.9% |
| 1,2-PDO | 2.5% | 0.32% | 20.0% | 1.47% | 2.1% |
| Water | | 2.73% | 10.0% | 26.32% | |
| 2-EH | | 95.65% | 98.2% | 1.99% | |

Example 12

This example illustrates a computer-generated material balance for a fractional extraction of a mixed diol feed comprising 95 weight percent EG, 2.5 weight percent 1,2-PDO, and 2.5 weight percent 1,2-BDO. The extractant for the fractional extraction contains 99.1 weight percent 2-ethylhexanol and 0.9 weight percent water. The column comprises fifteen theoretical stages. The mixed diol feed is fed on stage ten (from the bottom), the extractant, is introduced on stage one (from bottom), and the water wash on stage 15. The water to mixed diol feed weight ratio is 0.53:1.0, and the extractant to mixed diol feed ratio is 4.5:1.0. The system was modeled using the Kremser method, as described in Treybal, *Liquid Extraction*, $2^{nd}$ Ed., McGraw Hill Book Company, 1963, pp. 248-252, with partition coefficients correlated from the data of Examples 3 and 6. Material balance (all values in kg/hr) data are given in Table 10. Recovery of 1,2-BDO to the extract product is 98.0 weight percent. Recovery of EG to the raffinate is 99.95 weight percent.

TABLE 10

| Stream ID | EG | 1,2-PDO | 1,2-BDO | Water | 2-EH | Total |
|---|---|---|---|---|---|---|
| Mixed Diol Feed | 95 | 2.5 | 2.5 | | | 100.0 |
| Extractant | | | | 5.0 | 450.0 | 455.0 |
| Water Wash | | | | 53.0 | | 53.0 |
| TOTAL IN | 95 | 2.5 | 2.5 | 58.0 | 450.0 | 608.0 |
| Extract | 0.04 | 0.33 | 2.45 | 6.0 | 447.4 | 456.22 |
| Raffinate | 94.96 | 2.17 | 0.05 | 52.0 | 2.6 | 151.78 |
| TOTAL OUT | 95 | 2.5 | 2.5 | 58.0 | 450.0 | 608.0 |

Example 13

This example illustrates a computer-generated material balance for a fractional extraction of a mixed diol feed comprising 95 weight percent EG, 2.5 weight percent 1,2-PDO, and 2.5 weight percent 1,2-BDO. The extractant for the fractional extraction contains 80 weight percent Cyanex® 923 and 20 weight percent heptane. The column comprises fifteen theoretical stages. The mixed diol feed is fed on stage ten (from the bottom), the extractant is introduced on stage one (from bottom), and the water wash on stage 15. The water to mixed diol feed weight ratio is 0.57:1.0, and the extractant to mixed diol feed ratio is 2.0:1.0. The system was modeled using the Kremser method, as described in Treybal, *Liquid Extraction*, $2^{nd}$ Ed., McGraw Hill Book Company, 1963, pp. 248-252, with partition coefficients correlated from the data of Example 10. Material balance (all values in kg/hr) data are given in Table 11. Recovery of 1,2-BDO to the extract product is 99.7 weight percent. Recovery of EG to the raffinate is 99.95 weight percent.

TABLE 11

| Stream ID | EG | 1,2-PDO | 1,2-BDO | Water | C923 | HEP | Total |
|---|---|---|---|---|---|---|---|
| Mixed Diol Feed | 95 | 2.5 | 2.5 | | | | 100.0 |
| Extractant | | | | | 160.0 | 40.0 | 200.0 |
| Water Wash | | | | 57.0 | | | 57.0 |
| TOTAL IN | 95 | 2.5 | 2.5 | 57.0 | 160.0 | 40.0 | 357.0 |
| Extract | 0.05 | 0.12 | 2.49 | 17.8 | 159.99 | 40.0 | 220.45 |
| Raffinate | 94.95 | 2.38 | 0.01 | 39.2 | 0.01 | 0.0 | 136.55 |
| TOTAL OUT | 95 | 2.5 | 2.5 | 57.0 | 160.0 | 40.0 | 357.0 |

Example 14

This example illustrates a computer-generated material balance for the fractional distillation of a mixed diol feed comprising 99.785 weight percent EG, 0.097 weight percent 1,2-PDO (970 ppm by weight), and 0.118 weight percent 1,2-BDO (1180 ppm by weight), derived for example, from the hydrogenation of glycolic acid species. One hundred kg/hr of a mixed diol feed is fed to the eighteenth stage of a distillation column comprising thirty-six theoretical stages (numbered from the top down), a reboiler, and a condenser. The column is operated at 0.2 bar absolute and the reflux ratio and reboiler heat duty is varied to achieve 80 ppm by mass of 1,2-PDO and 1,2-BDO combined in the EG underflow product. Results are given in Table 12.

TABLE 12

| Example | Reflux Ratio | Heat Duty, MJ/hr | | EG | 1,2-PDO | 1,2-BDO |
|---|---|---|---|---|---|---|
| 14-1 | 204.3 | 352.1 | F, Kg/hr | 99.785 | 0.097 | 0.118 |
| | | | D, Kg/hr | 1.701 | 0.095 | 0.112 |
| | | | B, Kg/hr | 98.084 | 0.002 | 0.006 |
| | | | B Purity | 99.992% | 16 ppm | 64 ppm |
| 14-2 | 480.7 | 403.4 | D, Kg/hr | 0.75 | 0.096 | 0.111 |
| | | | B, Kg/hr | 99.035 | 0.001 | 0.007 |
| | | | B Purity | 99.992% | 13 ppm | 67 ppm |
| 14-3 | 5432.11 | 1686.5 | D, Kg/hr | 0.179 | 0.097 | 0.11 |
| | | | B, Kg/hr | 99.606 | 0 | 0.008 |
| | | | B Purity | 99.992% | 5 ppm | 75 ppm |

Example 15

This example illustrates a computer-generated material balance for the pre-distillation of a mixed diol feed comprising 99.785 weight percent EG, 0.097 weight percent 1,2-PDO (970 ppm by weight), and 0.118 weight percent 1,2-BDO (1180 ppm by weight), derived for example, from the hydrogenation of glycolic acid species. One hundred kg/hr of a mixed diol feed is fed to the eighteenth stage of a distillation column comprising thirty-six theoretical stages (numbered from the top down), a reboiler, and a condenser. The column is operated at 0.2 bar absolute in the distillate at a mass reflux ratio of 1086:1. Heat duty in the reboiler is calculated as 329 MJ/hr. Material balance (all values in kg/hr) data are given in Table 13. Recovery of 1,2-BDO and 1,2-PDO to the distillate product are 70 weight percent and 95 weight percent, respectively. Recovery of EG to the bottoms product is 99.8 weight percent. The purified EG bottoms product consists of 49 ppm by weight 1,2-PDO, 347 ppm by weight of 1,2-BDO, and the remainder EG.

TABLE 13

|         | Bottoms | Distillate | Feed   |
|---------|---------|------------|--------|
| EG      | 99.592  | 0.193      | 99.785 |
| 1,2-PDO | 0.005   | 0.092      | 0.097  |
| 1,2-BDO | 0.035   | 0.083      | 0.118  |

Example 16

This example illustrates a computer-generated material balance for a fractional extraction of a mixed diol feed comprising 99.96 weight percent EG, 49 ppm by weight 1,2-PDO, and 347 ppm by weight 1,2-BDO. This composition is the same as the bottoms product of the distillation step described in Example 15. The extractant for the fractional extraction contains 99.1 weight percent 2-ethylhexanol and 0.9 weight percent water. The column comprises fifteen theoretical stages. The mixed diol feed is fed on stage ten (from the bottom), the extractant is introduced on stage one (from bottom), and the water wash on stage 15. The water wash to mixed diol feed weight ratio is 0.16:1.0, and the extractant to mixed diol feed ratio is 2.5:1.0. The system was modeled using the Kremser method, as described in Treybal, *Liquid Extraction*, $2^{nd}$ Ed., McGraw Hill Book Company, 1963, pp. 248-252, with partition coefficients correlated from the data of Examples 3 and 6. Material balance (all values in kg/hr) data are given in Table 14. Recovery of 1,2-BDO to the extract product is 89.6 weight percent. Recovery of EG to the raffinate is 99.99 weight percent. The EG product on a solvent-free and water-free basis comprises 36 ppm by weight 1,2-BDO, 42 ppm by weight of 1,2-PDO, and the remainder EG.

TABLE 14

| Stream ID        | EG      | 1,2-PDO | 1,2-BDO | Water | 2-EH   | Total  |
|------------------|---------|---------|---------|-------|--------|--------|
| Mixed Diol Feed  | 99.59   | 0.00500 | 0.03500 |       |        | 99.632 |
| Extractant       |         |         |         | 2.29  | 249.08 | 251.38 |
| Water Wash       |         |         |         | 15.76 |        | 15.76  |
| TOTAL IN         | 99.59   | 0.01    | 0.04    | 18.05 | 249.08 | 366.77 |
| Extract          | 0.0163  | 0.00078 | 0.03139 | 1.00  | 235.09 | 236.15 |
| Raffinate        | 99.58   | 0.00422 | 0.00363 | 17.05 | 13.99  | 130.62 |
| TOTAL OUT        | 99.59   | 0.00    | 0.04    | 18.05 | 249.08 | 366.77 |

Example 17

This example illustrates a computer-generated material balance for a fractional extraction of a mixed diol feed comprising 99.96 weight percent EG, 49 ppm by weight 1,2-PDO, and 347 ppm by weight 1,2-BDO. This composition is the same as the bottoms product of the distillation step described in Example 15. The extractant for the fractional extraction contains 80 weight percent Cyanex® 923 and 20 weight percent decane. The column comprises fifteen theoretical stages. The mixed diol feed is fed on stage ten (from the bottom), the extractant, is introduced on stage one (from bottom), and the water wash on stage 15. The water wash to mixed diol feed weight ratio is 0.36:1.0, and the extractant to mixed diol feed ratio is 1.35:1.0. The system was modeled using the Kremser method, as described in Treybal, *Liquid Extraction*, $2^{nd}$ Ed., McGraw Hill Book Company, 1963, pp. 248-252, with partition coefficients correlated from the data of Example 10 (i.e., the partition coefficients calculated from the 80 weight percent Cyanex® 923 and 20 weight percent heptane extractant are used). Material balance (all values in kg/hr) data are given in Table 15. Recovery of 1,2-BDO to the extract product is 90.4 weight percent. Recovery of EG to the raffinate is 99.72 weight percent. The EG product on a solvent-free and water-free basis comprises 34 ppm by weight 1,2-BDO, 48 ppm by weight of 1,2-PDO, and the remainder EG.

TABLE 15

| Stream ID        | EG     | 1,2-PDO | 1,2-BDO | Water | C923   | Decane | Total  |
|------------------|--------|---------|---------|-------|--------|--------|--------|
| Mixed Diol Feed  | 99.59  | 0.00500 | 0.03500 |       |        |        | 99.632 |
| Extractant       |        |         |         |       | 107.60 | 26.90  | 134.50 |
| Water Wash       |        |         |         | 40.82 |        |        | 37.17  |
| TOTAL IN         | 99.59  | 0.01    | 0.04    | 40.82 | 107.60 | 26.90  | 274.96 |
| Extract          | 0.2746 | 0.00018 | 0.03163 | 11.96 | 107.59 | 26.90  | 146.76 |
| Raffinate        | 99.32  | 0.00482 | 0.00336 | 28.86 | 0.01   | 0.00   | 128.20 |
| TOTAL OUT        | 99.59  | 0.00    | 0.03    | 40.82 | 107.60 | 26.90  | 274.96 |

Example 18

This example illustrates a computer-generated model for the recovery of the extracted diols from the extractant solvent mixture by back extraction with water. The extract phase from Example 16, is fed to the bottom stage of an extraction column comprising twelve theoretical stages. The water back extractant is introduced on stage twelve (from bottom). The water to feed weight ratio is 0.6:1.0. The system was modeled using the Kremser method, as described in Treybal, *Liquid Extraction*, $2^{nd}$ Ed., McGraw Hill Book Company, 1963, pp. 248-252, with partition coefficients correlated from the data of Example 3 and 6. Material balance (all values in kg/hr) data are given in Table 16. Recovery of 1,2-BDO to the water extract product is 99.93 weight percent.

TABLE 16

| Stream ID | EG | 1,2-PDO | 1,2-BDO | Water | 2-EH | Total |
|---|---|---|---|---|---|---|
| Extract Phase, Example 16 | 0.0163 | 0.0008 | 0.0314 | 1.00 | 235.09 | 236.14 |
| Extractant | | | | 141.69 | 0.00 | 141.69 |
| TOTAL IN | 0.0163 | 0.00 | 0.03 | 142.69 | 235.09 | 377.83 |
| Extract | 0.0163 | 0.00078 | 0.03137 | 140.39 | 0.05 | 140.49 |
| Raffinate | 0.00 | 0.00000 | 0.00002 | 2.29 | 235.04 | 237.33 |
| TOTAL OUT | 0.02 | 0.00 | 0.03 | 142.69 | 235.09 | 377.83 |

Example 19

This example illustrates a computer-generated model for the recovery of the extracted diols from the extractant solvent mixture by distillation. The extract phase from Example 17, is fed to the eighth stage of a fifteen theoretical stage distillation column operated at 150 torr, and a reflux ratio of 2:1. Heterogeneous azeotropes of water, 1,2-PDO, 1,2-BDO, and EG with decane (the hydrocarbon component of the extractant,) are distilled as overhead product, allowed to decant into two phases, and the hydrocarbon-rich phase is refluxed back to the column. The water layer of the decanter comprising essentially all of the EG, 1,2-PDO, 1,2-BDO, and water is continuously removed from the column/decanter. In this fashion, the decane/C923 bottoms product is purified for recycle to the extraction step of Example 17.

Example 20

This example illustrates a computer-generated model for a single feed distillation of an EG/1,2-BDO mixed diol feed comprising 80 weight percent EG and 20 weight percent 1,2-BDO. One hundred kg/hr of the aforementioned mixed diol feed is fed to eighteenth stage of a distillation column comprising thirty-six theoretical stages (numbered from the top down), a reboiler, and a condenser. The column is operated at 0.2 bar absolute in the distillate at a mass reflux ratio of 2.82:1. Heat duty in the reboiler is calculated as 260.4 MJ/hr. Material balance (all values in kg/hr) data are given in Table 17. Recovery of EG to the bottoms product is only 25 weight percent, as the EG/1,2-BDO azeotrope severely limits the practical separation of EG and 1,2-BDO. The purified EG bottoms product consists of 2000 ppm by weight 1,2-BDO and 99.8 weight percent EG.

TABLE 17

| | Bottoms | Distillate | Feed |
|---|---|---|---|
| EG | 19.958 | 60.042 | 80.0 |
| 1,2-BDO | 0.04 | 19.960 | 20.0 |

Example 21

This example illustrates a computer-generated material balance for a fractional extraction of a mixed diol feed comprising 80 weight percent EG and 20 weight percent 1,2-BDO. The extractant for the fractional extraction contains 99.1 weight percent 2-ethylhexanol and 0.9 weight percent water. The column comprises fifteen theoretical stages. The mixed diol feed is fed on stage ten (from the bottom), the extractant is introduced on stage one (from bottom), and the water wash on stage 15. The water wash to mixed diol feed weight ratio is 0.16:1.0, and the extractant to mixed diol feed ratio is 4.3:1.0. The system was modeled using the Kremser method, as described in Treybal, *Liquid Extraction*, $2^{nd}$ Ed., McGraw Hill Book Company, 1963, pp. 248-252, with partition coefficients correlated from the data of Examples 3 and 6. Material balance (all values in kg/hr) data are given in Table 18. Recovery of 1,2-BDO to the extract is 99.3 weight percent. Recovery of EG to the raffinate is 99.81 weight percent. The raffinate comprises 0.2 weight percent 1,2-BDO and 99.8 weight percent EG on a solvent-free and water-free basis.

TABLE 18

| Stream ID | EG | 1,2-BDO | Water | 2-EH | Total |
|---|---|---|---|---|---|
| Mixed Diol Feed | 80.00 | 20.00 | | | 100.00 |
| Extractant | | | 4.30 | 430.00 | 434.30 |
| Water Wash | | | 16.10 | | 16.10 |
| TOTAL IN | 80.00 | 20.00 | 20.40 | 430.00 | 550.40 |
| Extract | 0.15 | 19.87 | 1.65 | 420.93 | 442.60 |
| Raffinate | 79.85 | 0.15 | 18.75 | 9.07 | 107.80 |
| TOTAL OUT | 80.0 | 20.0 | 20.40 | 430.00 | 550.40 |

Example 22

This example illustrates a computer-generated material balance for a fractional extraction of a mixed diol feed comprising 80 weight percent 1,2-PDO, 20 weight percent 1,2-BDO. The extractant for the fractional extraction contains 87.5 weight percent Cyanex® 923, 9.72 weight percent heptane, and 2.78 weight percent water. The column comprises fifteen theoretical stages. The mixed diol feed is fed on stage ten (from the bottom), the extractant is introduced on stage one (from bottom), and the water wash on stage 15. The water wash to mixed diol feed weight ratio is 0.795:1.0, and the extractant to mixed diol feed ratio is 1.8:1.0. The system was modeled using the Kremser method, as described in Treybal, *Liquid Extraction*, $2^{nd}$ Ed., McGraw Hill Book Company, 1963, pp. 248-252, with partition coefficients correlated from the data of Example 10. Material balance (all values in kg/hr) data are given in Table 19. Recovery of 1,2-BDO to the extract product is 99.87 weight percent. Recovery of 1,2-PDO to the raffinate is 98.98 weight percent. The raffinate comprises 333 ppm by weight 1,2-BDO and 99.967 1,2-PDO on a solvent-free and water-free basis.

TABLE 19

| Stream ID | 1,2-PDO | 1,2-BDO | Water | C923 | HEPT | Total |
|---|---|---|---|---|---|---|
| Mixed Diol Feed | 80.00 | 20.00 | | | | 100.00 |
| Extractant | | | 5.01 | 157.50 | 17.50 | 180.01 |
| Water Wash | | | 79.47 | | | 79.47 |
| TOTAL IN | 80.00 | 20.00 | 84.47 | 157.50 | 17.50 | 359.47 |
| Extract | 0.82 | 19.97 | 14.75 | 157.48 | 17.50 | 210.53 |
| Raffinate | 79.18 | 0.026 | 69.72 | 0.02 | 0.00 | 148.94 |

Example 23

This example illustrates the separation of diols from a glycerol-containing aqueous mixture. A standard diol/glycerol solution was prepared comprising an aqueous solution of 84 weight percent water, 10 weight percent glycerol (GLY), 2 weight percent each of ethylene glycol (EG), 1,2-propanediol (1,2-PDO), and 1,2-butanediol (1,2-BDO). Fifteen grams of this standard solution was added to a separate glass vial along with fifteen grams of each of the nonpolar solvents listed in Table 20. The contents were mixed vigorously and allowed to settle and separate into two clear phases. The phases were analyzed by gas chromatography to determine glycerol, EG, 1,2-PDO, 1,2-BDO weight percentages. These analytical results were used to calculate partition coefficients and selectivities. All experiments were conducted at room temperature. Results are summarized in Table 20.

TABLE 20

| Ex | Solvent | P(EG) | P(1,2-PDO) | P(1,2-BDO) | P(GLY) | S(EG/GLY) | S(1,2-PDO/GLY) | S(1,2-BDO/GLY) |
|---|---|---|---|---|---|---|---|---|
| 23-1 | n-pentanol | 0.19 | 0.40 | 1.11 | 0.07 | 2.54 | 5.44 | 15.05 |
| 23-2 | 2-EH | 0.05 | 0.13 | 0.42 | 0.01 | 4.99 | 12.23 | 38.53 |
| 23-3 | EA | 0.04 | 0.10 | 0.29 | 0.01 | 5.31 | 11.57 | 34.70 |
| 23-4 | MIBK | 0.02 | 0.06 | 0.20 | 0.00 | 7.56 | 18.10 | 64.73 |
| 23-5 | 50 wt % Heptane/ 50 wt % C923 | 0.07 | 0.19 | 0.74 | 0.02 | 3.01 | 7.68 | 29.85 |

Example 24

This example illustrates the separation of diols from a glycerol-rich aqueous mixture. A standard diol/glycerol solution was prepared comprising 84 weight percent glycerol (GLY), 10 weight percent water, 2 weight percent each of ethylene glycol (EG), 1,2-propanediol (1,2-PDO), and 1,2-butanediol (1,2-BDO). Fifteen grams of this standard solution was added to a separate glass vial along with fifteen grams of each of the nonpolar solvents listed in Table 21. The contents were mixed vigorously and allowed to settle and separate into two clear phases. The phases were analyzed by gas chromatography to determine glycerol, EG, 1,2-PDO, 1,2-BDO weight percentages. These analytical results were used to calculate partition coefficients and selectivities. All experiments were conducted at room temperature. Results are summarized in Table 21.

TABLE 21

| Ex | Solvent | P(EG) | P(1,2-PDO) | P(1,2-BDO) | P(GLY) | S(EG/GLY) | S(1,2-PDO/GLY) | S(1,2-BDO/GLY) |
|---|---|---|---|---|---|---|---|---|
| 24-1 | n-pentanol | 0.57 | 0.97 | 1.66 | 0.32 | 1.76 | 3.01 | 5.14 |
| 24-2 | 2-EH | 0.17 | 0.40 | 0.89 | 0.05 | 3.46 | 7.85 | 17.58 |
| 24-3 | EA | 0.08 | 0.18 | 0.41 | 0.02 | 4.65 | 11.10 | 24.65 |
| 24-4 | MIBK | 0.06 | 0.14 | 0.33 | 0.01 | 5.51 | 13.27 | 32.06 |
| 24-5 | 50 wt % Heptane/ 50 wt % C923 | 0.18 | 0.46 | 1.28 | 0.07 | 2.78 | 6.92 | 19.28 |

Example 25

This example illustrates the separation of diols from glucose (GLU). A standard diol/glucose solution was prepared comprising an aqueous solution of 10 weight percent glucose (GLU), 84 weight percent water, 2 weight percent each of ethylene glycol (EG), 1,2-propanediol (1,2-PDO), and 1,2-butanediol (1,2-BDO). Fifteen grams of this standard solution was added to a separate glass vial along with fifteen grams of each of the nonpolar solvents listed in Table 22. The contents were mixed vigorously and allowed to settle and separate into two clear phases. The phases were analyzed by gas chromatography to determine glycerol, EG, 1,2-PDO, 1,2-BDO weight percentages. These analytical results were used to calculate partition coefficients and selectivities. All experiments were conducted at room temperature. Results are summarized in Table 22.

TABLE 22

| Ex | Solvent | P(EG) | P(1,2-PDO) | P(1,2-BDO) | P(GLU) | S(EG/GLU) | S(1,2-PDO/GLU) | S(1,2-BDO/GLU) |
|---|---|---|---|---|---|---|---|---|
| 25-1 | n-pentanol | 0.20 | 0.43 | 1.21 | 0.01 | 15.02 | 32.38 | 91.20 |
| 25-2 | 2-EH | 0.06 | 0.14 | 0.46 | 0.00 | ∞ | ∞ | ∞ |
| 25-3 | EA | 0.04 | 0.11 | 0.32 | 0.00 | ∞ | ∞ | ∞ |
| 25-4 | MIBK | 0.03 | 0.06 | 0.21 | 0.00 | ∞ | ∞ | ∞ |
| 25-5 | 50 wt % Heptane/ 50 wt % C923 | 0.08 | 0.20 | 0.81 | 0.004 | 20.51 | 53.28 | 213.02 |

What is claimed is:

1. A process for recovering diols from a mixed diol stream, comprising
    (A) extracting said mixed diol stream, comprising
        (i) 0.1 weight percent to 50 weight percent of one or more diols selected from the group consisting of ethylene glycol, 1,2-propanediol, 1,3-propanediol, 1,2-butanediol, 1,3-butanediol, 1,4-butanediol, and 2,3-butanediol;
        (ii) 5 weight percent to 90 weight percent glycerol; and
        (iii) 5 weight percent to 90 weight percent water; each based on the total weight of said mixed diol steam stream, with an extractant, comprising
            (i) a hydrophobic solvent selected from alkanols having from 6 to 20 carbon atoms, ketones having from 5 to 20 carbon atoms, esters having from 5 to 20 carbon atoms, ethers having from 5 to 20 carbon atoms, carboxylic acids having from 5 to 20 carbon atoms, trialkylphosphine oxides having from 18 to 48 carbon atoms, and mixtures thereof; and
            (ii) optionally, a second modifying hydrophobic solvent selected from hydrocarbons having from 5 to 20 carbon atoms; to form a raffinate phase comprising a major amount of said glycerol and a minor amount of said diols contained in said mixed diol stream and an extract phase comprising a major amount of said diols and a minor amount of said glycerol contained in said mixed diol stream; and
    (B) separating said raffinate phase and said extract phase.

2. The process according to claim 1 wherein said hydrophobic solvent is selected from 2-ethylhexanol, cyclohexanol, n-hexanol, methyl isobutyl ketone, methyl isopropyl ketone, methyl propyl ketone, diisobutyl ketone, trioctylphosphine oxide, trihexylphosphine oxide, and mixtures thereof.

3. The process according to claim 2 wherein greater than 99.5 weight percent of said glycerol is recovered in said raffinate phase and greater than 90 weight percent of said diols is recovered in said extract phase; and wherein said extraction occurs in a continuous counter-current extractor, wherein said extractant is fed lower to said extractor than said mixed diol stream, wherein the feed ratio of said extractant to said mixed diol stream ranges from 0.1:1 to 10:1; further comprising feeding a hydrophilic stream to said extractor at a higher level than said mixed diol stream, wherein the feed ratio of said hydrophilic stream to said mixed diol stream ranges from 0.05:1 to 2.0:1, and wherein said hydrophilic stream comprises water.

4. A process for recovering diols from a mixed diol stream, comprising
    (A) extracting said mixed diol stream, comprising
        (i) 0.1 weight percent to 30 weight percent of one or more diols selected from the group consisting of ethylene glycol, 1,2-propanediol, 1,3-propanediol, 1,2-butanediol, 1,3-butanediol, 1,4-butanediol, and 2,3-butanediol;
        (ii) 5 weight percent to 50 weight percent glucose; and
        (iii) 50 weight percent to 90 weight percent water; each based on the total weight of said mixed diol steam stream, with an extractant, comprising
            (i) a hydrophobic solvent selected from alkanols having from 6 to 20 carbon atoms, ketones having from 5 to 20 carbon atoms, esters having from 5 to 20 carbon atoms, ethers having from 5 to 20 carbon atoms, carboxylic acids having from 5 to 20 carbon atoms, trialkylphosphine oxides having from 18 to 48 carbon atoms, and mixtures thereof; and
            (ii) optionally, a second modifying hydrophobic solvent selected from hydrocarbons having from 5 to 20 carbon atoms; to form a raffinate phase comprising a major amount of said glycerol and a minor amount of said diols contained in said mixed diol stream and an extract phase comprising a major amount of said diols and a minor amount of said glycerol contained in said mixed diol stream; and
    (B) separating said raffinate phase and said extract phase.

5. The process according to claim 4 wherein said hydrophobic solvent is selected from 2-ethylhexanol, cyclohexanol, n-hexanol, methyl isobutyl ketone, methyl isopropyl ketone, methyl propyl ketone, diisobutyl ketone, trioctylphosphine oxide, trihexylphosphine oxide, and mixtures thereof.

6. The process according to claim 5 wherein greater than 99.5 weight percent of said glucose is recovered in said raffinate phase and greater than 90 weight percent of diols is recovered in said extract phase; and wherein said extraction occurs in a continuous counter-current extractor, wherein said extractant is fed lower to said extractor than said mixed diol stream, wherein the feed ratio of said extractant to said mixed diol stream ranges from 0.1:1 to 10:1; further comprising feeding a hydrophilic stream to said extractor at a higher level than said mixed diol stream, wherein the feed ratio of said hydrophilic stream to said mixed diol stream ranges from 0.05:1 to 2.0:1, and wherein said hydrophilic stream comprises water.

7. A process for recovering purified three-carbon diols from a mixed diol stream, comprising
    (A) extracting said mixed diol stream, comprising
        (i) 1 weight percent to 99.5 weight of one or more three-carbon diols selected from 1,2-propanediol and 1,3-propanediol;
        (ii) 20 ppm by weight to 99 weight percent of one or more four-carbon diols selected from 1,2-butanediol, 1,3-butanediol, 1,4-butanediol, and 2,3-butanediol; each based on the total weight of said diols, and
        (iii) 0 weight percent to 50 weight percent water, based on the total weight of said diols and said water, with an extractant, comprising (i) a hydrophobic solvent selected from alkanols having from 6 to 20 carbon atoms, ketones having from 5 to 20 carbon atoms, esters having from 5 to 20 carbon atoms, ethers having from 5 to 20 carbon atoms, carboxylic acids having from 5 to 20 carbon atoms, trialkylphosphine oxides having from 18 to 48 carbon atoms, and mixtures thereof; and (ii) optionally, a second modifying hydrophobic solvent selected from hydrocarbons having from 5 to 20 carbon atoms; to form a raffinate phase comprising a major amount of said three-carbon diols and a minor amount of said four-carbon diols contained in said mixed diol stream and an extract phase comprising a major amount of said four-carbon diols and a minor amount of said three-carbon diols contained in said mixed diol stream; and (B) separating said raffinate phase and said extract phase.

8. The process according to claim 7 wherein said hydrophobic solvent is selected from 2-ethylhexanol, cyclohexanol, n-hexanol, methyl isobutyl ketone, methyl isopropyl ketone, methyl propyl ketone, diisobutyl ketone, trioctylphosphine oxide, trihexylphosphine oxide, and mixtures thereof.

9. The process according to claim 8 wherein greater than 99.5 weight percent of said three-carbon diols in said mixed diol stream is recovered in said raffinate phase and greater than 90 weight percent of said four-carbon diols is recovered in said extract phase; and wherein said extraction occurs in a continuous counter-current extractor, wherein said extractant is fed lower to said extractor than said mixed diol stream, wherein the feed ratio of said extractant to said mixed diol stream ranges from 0.1:1 to 10:1; further comprising feeding a hydrophilic stream to said extractor at a higher level than said mixed diol stream, wherein the feed ratio of said hydrophilic stream to said mixed diol stream ranges from 0.05:1 to 1.5:1, and wherein said hydrophilic stream comprises water.

* * * * *